(12) United States Patent
Bucher et al.

(10) Patent No.: US 11,256,995 B1
(45) Date of Patent: Feb. 22, 2022

(54) SYSTEM AND METHOD FOR PREDICTION OF PROTEIN-LIGAND BIOACTIVITY USING POINT-CLOUD MACHINE LEARNING

(71) Applicant: Ro5 Inc., Dallas, TX (US)

(72) Inventors: Alwin Bucher, Cambridge (GB); Alvaro Prat, Barcelona (ES); Orestis Bastas, Vyronas (GR); Aurimas Pabrinkis, London (GB); Gintautas Kamuntavičius, Vilniaus rajonas (LT); Mikhail Demtchenko, London (GB); Sam Christian Macer, Leicestershire (GB); Zeyu Yang, London (GB); Cooper Stergis Jamieson, Venice, CA (US); Žygimantas Jočys, Hove (GB); Roy Tal, Dallas, TX (US); Charles Dazler Knuff, Dallas, TX (US)

(73) Assignee: RO5 INC., Dallas, TX (US)

( * ) Notice: Subject to any disclaimer, the term of this patent is extended or adjusted under 35 U.S.C. 154(b) by 0 days.

(21) Appl. No.: 17/237,458

(22) Filed: Apr. 22, 2021

Related U.S. Application Data

(63) Continuation-in-part of application No. 17/202,722, filed on Mar. 16, 2021, which is a continuation-in-part of application No. 17/174,677, filed on Feb. 12, 2021, which is a continuation of application No. 17/171,494, filed on Feb. 9, 2021, which is a continuation of application No. 17/166,435, filed on Feb. 3, 2021, now Pat. No. 11,080,607.

(60) Provisional application No. 63/126,388, filed on Dec. 16, 2020, provisional application No. 63/126,372, (Continued)

(51) Int. Cl.
*G06N 5/00* (2006.01)
*G06N 5/02* (2006.01)
*G06N 3/08* (2006.01)
*G06K 9/62* (2022.01)
*G06F 16/951* (2019.01)

(52) U.S. Cl.
CPC .......... *G06N 5/022* (2013.01); *G06F 16/951* (2019.01); *G06K 9/6215* (2013.01); *G06N 3/08* (2013.01)

(58) Field of Classification Search
CPC ........ G06N 5/022; G06N 3/08; G06F 16/951; G06K 9/6215
USPC .......................................... 706/45
See application file for complete search history.

(56) References Cited

U.S. PATENT DOCUMENTS

| | | | |
|---|---|---|---|
| 11,069,427 B2 * | 7/2021 | Bremel | G16B 5/00 |
| 2005/0074809 A1 | 4/2005 | Brusic | |
| 2019/0272887 A1 | 9/2019 | Feinberg et al. | |

(Continued)

*Primary Examiner* — Charlotte M Baker
(74) *Attorney, Agent, or Firm* — Galvin Patent Law LLC; Brian R. Galvin

(57) ABSTRACT

A system and method that predicts whether a given protein-ligand pair is active or inactive, the ground-truth protein-ligand complex crystalline-structure similarity, and an associated bioactivity value. The system and method further produce 3-D visualizations of previously unknown protein-ligand pairs that show directly the importance assigned to protein-ligand interactions, the positive/negative-ness of the saliencies, and magnitude. Furthermore, the system and method make enhancements in the art by accurately predicting protein-ligand pair bioactivity from decoupled models, removing the need for docking simulations, as well as restricting attention of the machine learning between protein and ligand atoms only.

20 Claims, 39 Drawing Sheets

Related U.S. Application Data filed on Dec. 16, 2020, provisional application No. 63/126,349, filed on Dec. 16, 2020.

(56) References Cited

U.S. PATENT DOCUMENTS

| | | |
|---|---|---|
| 2019/0303535 A1* | 10/2019 | Fokoue-Nkoutche ........................ G06N 7/005 |
| 2020/0342953 A1 | 10/2020 | Morrone et al. |
| 2021/0280275 A1* | 9/2021 | Akerman ............... G16H 20/30 |

* cited by examiner

Exemplary Point-Cloud Model Pseudocode
3400

```
# Shapes of Inputs
coords: shape(batch_size, 3, max_atoms_per_complex_in_batch)
types: shape(batch_size, num_lig_channels + num_prot_channels, max_atoms_per_complex_in_batch)
is_padding: shape(batch_size, 1, max_atoms_per_complex_in_batch)

# Forward pass of pointwise model (including spatial components)
pointwise_out = pointwise_model(coords, types, is_padding)

# For docking-prediction,
num_pointwise_outputs may be 3, and may be used to compute the loss.

# For bioactivity models, it may be 256, and may be agglomerated to compute a class
pointwise_out: shape(batch_size, num_pointwise_outputs, max_atoms_per_complex_in_batch)

# For regression/classification models, perform agglomeration
global_out = maxpool/averagepool(pointwise_out, dim=2)
global_out: shape(batch_size, num_pointwise_outputs) prediction = classifier/regressor(global_out)
```

Fig. 34

SYSTEM AND METHOD FOR PREDICTION OF PROTEIN-LIGAND BIOACTIVITY USING POINT-CLOUD MACHINE LEARNING

CROSS-REFERENCE TO RELATED APPLICATIONS

Priority is claimed in the application data sheet to the following patents or patent applications, the entire written description of each of which is expressly incorporated herein by reference in its entirety:
Ser. No. 17/202,722
Ser. No. 17/174,677
Ser. No. 17/171,494
Ser. No. 17/166,435
63/126,349
63/126,372
63/126,388

BACKGROUND

Field of the Art

The disclosure relates to the field of medical research, and more particularly to the field of prediction of the bioactivity interactions between molecules and proteins using point-cloud representation and analysis.

Discussion of the State of the Art

Pharmaceutical research is hindered by the complexity of protein-ligand interactions. Proteins are macromolecules involved in a large array of biological functions, comprising long chains of amino acids, each of which is itself an organic molecule. The shape of proteins determines their bioactivity, and the shape of a protein is determined by the way the protein folds based on its molecular structure. The complexity of proteins and their folding patterns makes their final shapes computationally intractable.

Ligands further complicate the issue as each ligand further changes the shape of the protein, which changes its bioactivity. Inferring the interaction between a protein and a ligand alone is a computationally difficult task because proteins are two or three orders of magnitude larger than a typical ligand and the number of possible interaction sites is very large. Further, each ligand further changes the shape of the protein, which changes its bioactivity, and the possible spatial conformations of a protein is several orders of magnitude larger than a ligand.

What is needed is a system and method for computationally tractable prediction of protein-ligand interactions and their bioactivity using a point-cloud machine learning model.

SUMMARY

Accordingly, the inventor has conceived and reduced to practice, a system and method that predicts whether a given protein-ligand pair is active or inactive, the ground-truth protein-ligand complex crystalline-structure similarity, and an associated bioactivity value. The system and method further produce 3-D visualizations of previously unknown protein-ligand pairs that show directly the importance assigned to protein-ligand interactions, the positive/negative-ness of the saliencies, and magnitude. Furthermore, the system and method make enhancements in the art by accurately predicting protein-ligand pair bioactivity from decoupled models, removing the need for docking simulations, as well as restricting attention of the machine learning between protein and ligand atoms only. The ground-truth protein-ligand complex crystalline-structure similarity refers to crystal structures of a ligand bound to a protein.

According to a first preferred embodiment, a system for prediction of protein-ligand bioactivity comprising: a computing device comprising a memory and a processor; a point-cloud based bioactivity module comprising a first plurality of programming instructions stored in the memory and operating on the processor, wherein the first plurality of programming instructions causes the computing device to: receive a molecular structure file, wherein the molecular structure file comprises molecular and structural information about at least one protein and one ligand; generate a graph-based neural network of the protein, wherein edges of the graph-based neural network of the protein are determined using the molecular structure file; generate a graph-based neural network of the ligand, wherein edges of the graph-based neural network of the ligand are determined using the molecular structure file; concatenate a set of vectors from both the graph-based neural network of the protein and the graph-based neural network of the ligand; perform restricted-cross-attention learning on the concatenated vectors; generate a single feature vector from the restricted-cross-attention learning; use the single feature vector in a feed-forward neural network to produce one or more outputs selected from the group consisting of active or inactive classification, crystalline-structure similarity, and regression analysis; and use the one or more outputs to produce one or more bioactivity predictions about one or more protein-ligand pairs.

According to a second preferred embodiment, a method for prediction of protein-ligand bioactivity comprising the steps of: receiving a molecular structure file, wherein the molecular structure file comprises molecular and structural information about at least one protein and one ligand; generating a graph-based neural network of the protein, wherein edges of the graph-based neural network of the protein are determined using the molecular structure file; generating a graph-based neural network of the ligand, wherein edges of the graph-based neural network of the ligand are determined using the molecular structure file; concatenating a set of vectors from both the graph-based neural network of the protein and the graph-based neural network of the ligand; performing restricted-cross-attention learning on the concatenated vectors; generating a single feature vector from the restricted-cross-attention learning; using the single feature vector in a feed-forward neural network to produce one or more outputs selected from the group consisting of active or inactive classification, crystalline-structure similarity, and regression analysis; and using the one or more outputs to produce one or more bioactivity predictions about one or more protein-ligand pairs.

According to various aspects of the invention; wherein docking simulations are performed on the protein and the ligand from the molecular structure file if the protein and the ligand are coupled; wherein the vector from the graph-based neural network of the protein comprises atoms within 4 angstroms of the ligand if the protein and the ligand are coupled; wherein the vector from the graph-based neural network of the protein comprises atoms of a binding pocket if the protein and the ligand are decoupled; wherein the crystalline-structure similarity prediction is used to determine the legitimacy of the one or more bioactivity predictions; wherein the graph-based neural network of the protein and the graph-based neural network of the ligand are based on one or more transformer convolution classifiers; wherein the one or more outputs are used with a loss function to produce a trained model for bioactivity prediction; wherein the machine learning model is a transformer convolution classifier; further comprising an output of a three-dimensional visualization of the one or more protein-ligand pairs; wherein the three-dimensional visualization comprises features of molecular interaction properties.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

FIG. 34 is a diagram of exemplary pseudocode for implementing a point-cloud based machine learning architecture.

DETAILED DESCRIPTION

Figure 1:
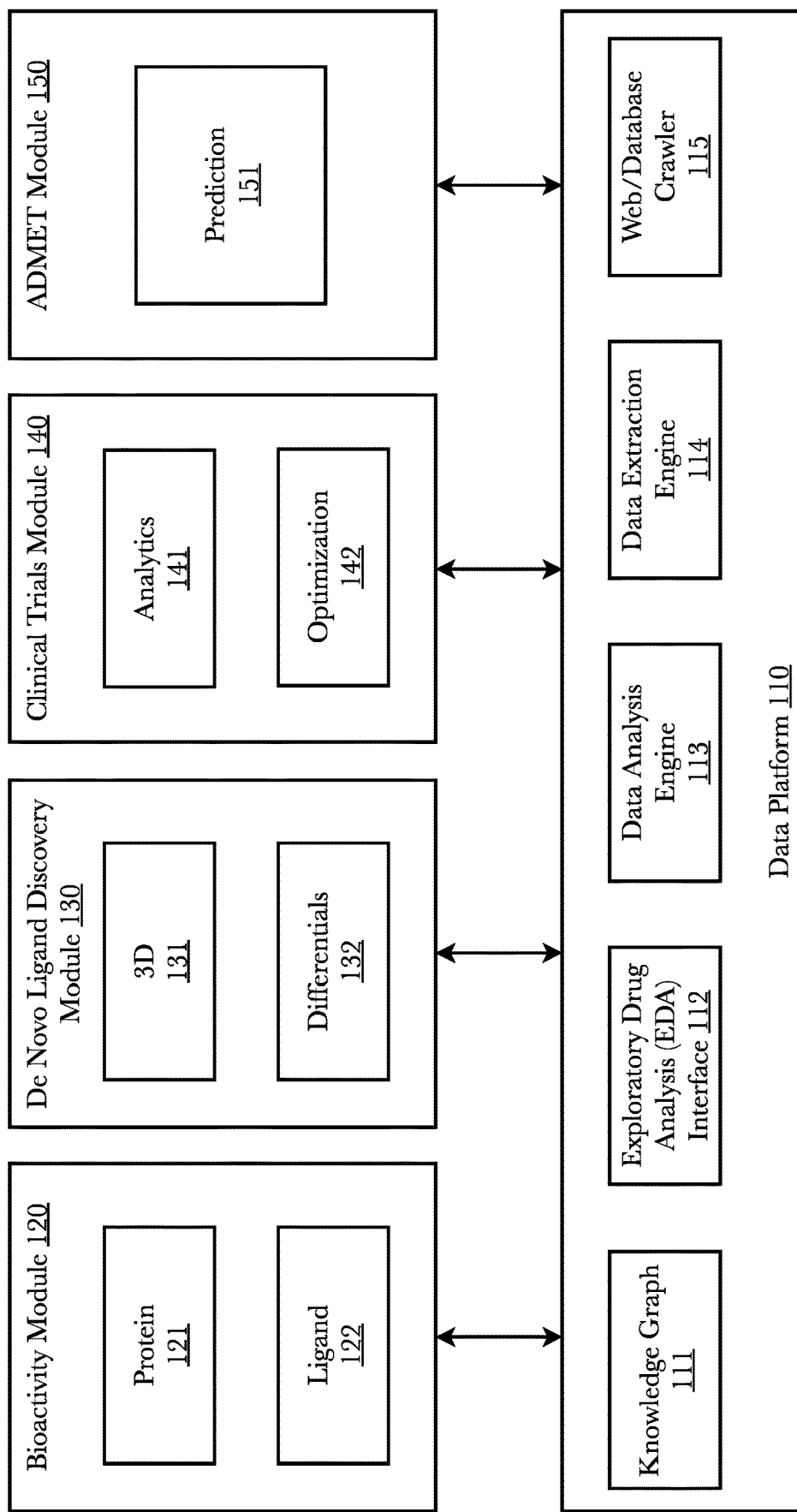
FIG. 1 is a block diagram illustrating an exemplary overall system architecture for a pharmaceutical research system.

Accordingly, the inventor has conceived and reduced to practice, a system and method that predicts whether a given protein-ligand pair is active or inactive, the ground-truth protein-ligand pair crystalline structure similarity, and an associated bioactivity value. The system and method further produce 3-D visualizations of previously unknown protein-ligand pairs that show directly the importance assigned to protein-ligand interactions, the positive/negative-ness of the saliencies, and magnitude. Furthermore, the system and method make enhancements in the art by accurately predicting protein-ligand pair bioactivity from decoupled models, removing the need for docking simulations, as well as restricting attention of the machine learning between protein and ligand atoms only.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

"Bioactivity" as used herein means the physiological effects of a molecule on an organism (i.e., living organism, biological matter).

"Docking" as used herein means a method which predicts the orientation of one molecule to a second when bound to each other to form a stable complex. Knowledge of the preferred orientation in turn may be used to predict the strength of association or binding affinity between two molecules.

"Edges" as used herein means connections between nodes or vertices in a data structure. In graphs, an arbitrary number of edges may be assigned to any node or vertex, each edge representing a relationship to itself or any other node or vertex. Edges may also comprise value, conditions, or other information, such as edge weights or probabilities.

"FASTA" as used herein means any version of the FASTA family (e.g., FASTA, FASTP, FASTA, etc.) of chemical notations for describing nucleotide sequences or amino acid (protein) sequences using text (e.g., ASCII) strings.

"Force field" as used herein means a collection of equations and associated constants designed to reproduce molecular geometry and selected properties of tested structures. In molecular dynamics a molecule is described as a series of charged points (atoms) linked by springs (bonds).

"Ligand" as used herein means a substance that forms a complex with a biomolecule to serve a biological purpose. In protein-ligand binding, the ligand is usually a molecule which produces a signal by binding to a site on a target protein. Ligand binding to a receptor protein alters the conformation by affecting the three-dimensional shape orientation. The conformation of a receptor protein composes the functional state. Ligands comprise substrates, inhibitors, activators, signaling lipids, and neurotransmitters.

"Nodes" and "Vertices" are used herein interchangeably to mean a unit of a data structure comprising a value, condition, or other information. Nodes and vertices may be arranged in lists, trees, graphs, and other forms of data structures. In graphs, nodes and vertices may be connected to an arbitrary number of edges, which represent relationships between the nodes or vertices. As the context requires, the term "node" may also refer to a node of a neural network (also referred to as a neuron) which is analogous to a graph node in that it is a point of information connected to other points of information through edges.

"Pocket" or "Protein binding pocket" as used herein means a cavity (i.e., receptor, binding site) on the surface or in the interior of a protein that possesses suitable properties for binding a ligand. The set of amino acid residues around a binding pocket determines its physicochemical characteristics and, together with its shape and location in a protein, defines its functionality.

"Pose" as used herein means a molecule within a protein binding site arranged in a certain conformation.

"Proteins" as used herein means large biomolecules, or macromolecules, consisting of one or more long chains of amino acid residues. Proteins perform a vast array of functions within organisms, including catalyzing metabolic reactions, DNA replication, responding to stimuli, providing structure to cells and organisms, and transporting molecules from one location to another. Proteins differ from one another primarily in their sequence of amino acids, which is dictated by the nucleotide sequence of their genes, and which usually results in protein folding into a specific 3D structure that determines its activity.

"SMILES" as used herein means any version of the "simplified molecular-input line-entry system," which is form of chemical notation for describing the structure of molecules using short text (e.g., ASCII) strings.

Conceptual Architecture

FIG. 1 is a block diagram illustrating an exemplary overall system architecture for a pharmaceutical research system. The exemplary architecture comprises a data platform 110 which provides the core functionality of the system, plus one or more modules that utilize the data platform 110 to provide functionality in specific areas of research, in this case a bioactivity module 120, a de novo ligand discovery module 130, a clinical trials module 140, and an absorption, distribution, metabolism, excretion, and toxicity (ADMET) module 150.

The data platform 110 in this embodiment comprises a knowledge graph 111, an exploratory drug analysis (EDA) interface 112, a data analysis engine 113, a data extraction engine 114, and web crawler/database crawler 115. The crawler 115 searches for and retrieves medical information such as published medical literature, clinical trials, dissertations, conference papers, and databases of known pharmaceuticals and their effects. The crawler 115 feeds the medical information to a data extraction engine 114, which uses natural language processing techniques to extract and classify information contained in the medical literature such as indications of which molecules interact with which proteins and what physiological effects have been observed. Using the data extracted by the data extraction engine 114, a knowledge graph 111 is constructed comprising vertices (also called nodes) representing pieces of knowledge gleaned from the data and edges representing relationships between those pieces of knowledge. As a very brief example, it may be that one journal article suggests that a particular molecule is useful in treating a given disease, and another journal article suggests that a different molecule is useful for treating the same disease. The two molecules and the disease may be represented as vertices in the graph, and the relationships among them may be represented as edges between the vertices. The EDA interface 112 is a user interface through which pharmaceutical research may be performed by making queries and receiving responses. The queries are sent to a data analysis engine 113 which uses the knowledge graph 111 to determine a response, which is then provided to the user through the EDA interface 112. In some embodiments, the data analysis engine 113 comprises one or more graph-based neural networks (graph neural networks, or GNNs) to process the information contained in the knowledge graph 111 to determine a response to the user's query. As an example, the user may submit a query for identification of molecules likely to have similar bioactivity to a molecule with known bioactivity. The data analysis engine 113 may process the knowledge graph 111 through a GNN to identify such molecules based on the information and relationships in the knowledge graph 111.

The bioactivity module 120 utilizes the data platform 110 to analyze and predict the bioactivity of molecules based on protein 121 and ligand 122 similarities and known or suspected protein 121 and ligand 122 compatibilities. The module utilizes the knowledge graph 111 and data analysis engine 113 capabilities of the data platform 110, and in one embodiment is configured to predict the bioactivity of a molecule based on and their known or suspected compatibilities with certain combinations of proteins 121 and ligands 122. Thus, using the bioactivity module 120, users can research molecules by entering queries through the EDA interface 112, and obtaining using predictions of bioactivity based on known or suspected bioactivity of similar molecules and their compatibilities with certain protein 121 and ligand 122 combinations.

The de novo ligand discovery module 130 utilizes the data platform 110 to identify ligands and their properties through data enrichment and interpolation/perturbation. The module utilizes the knowledge graph 111 and data analysis engine 113 capabilities of the data platform 110, and in one embodiment is configured to identify ligands with certain properties based on three dimensional (3D) models 131 of known ligands and differentials of atom positions 132 in the latent space of the models after encoding by a 3D convolutional neural network (3D CNN), which is part of the data analysis engine 113. In one embodiment, the 3D model comprises a voxel image (volumetric, three dimensional pixel image) of the ligand. In cases where enrichment data is available, ligands may be identified by enriching the SMILES string for a ligand with information about possible atom configurations of the ligand and converting the enriched information into a plurality of 3D models of the atom. In cases where insufficient enrichment information is available, one possible configuration of the atoms of the ligand may be selected, and other configurations may be generated by interpolation or perturbation of the original configuration in the latent space after processing the 3D model through the CNN. In either case, the 3D models of the ligands are processed through a CNN, and a gradient descent is applied to changes in atom configuration in the latent space to identify new ligands with properties similar to the modeled ligands. Thus, using the de novo ligand discovery module 130, users can identify new ligands with properties similar to those of modeled ligands by entering queries through the EDA interface 112.

The clinical trials module 140 utilizes the data platform 110 to analyze 141 and optimize 142 the knowledge contained in or derived from clinical trials. The module utilizes the knowledge graph 111 and data analysis engine 113 capabilities of the data platform 110, and in one embodiment is configured to return clinical trials similar to a specified clinical trial in one or more aspects (e.g., proteins and ligands studied, methodology, results, etc.) based on semantic clustering within the knowledge graph 111. Thus, using the clinical trials module 140, users can research a large database of clinical trials based on aspects of interest by entering queries through the EDA interface 112.

The ADMET module 150 utilizes the data platform 110 to predict 151 absorption, distribution, metabolism, excretion, and toxicity characteristics of ligands based on ADMET databases. The module utilizes the knowledge graph 111 and data analysis engine 113 capabilities of the data platform 110, and in one embodiment is configured to return ligands with characteristics similar to, or dissimilar to, a specified ligand in one or more respects (e.g., a ligand with similar absorption and metabolism characteristics, but dissimilar toxicity characteristics) based on semantic clustering within the knowledge graph 111. Thus, using the ADMET module 150, users can research a large ADMET database based on aspects of interest by entering queries through the EDA interface 112.

Figure 2:
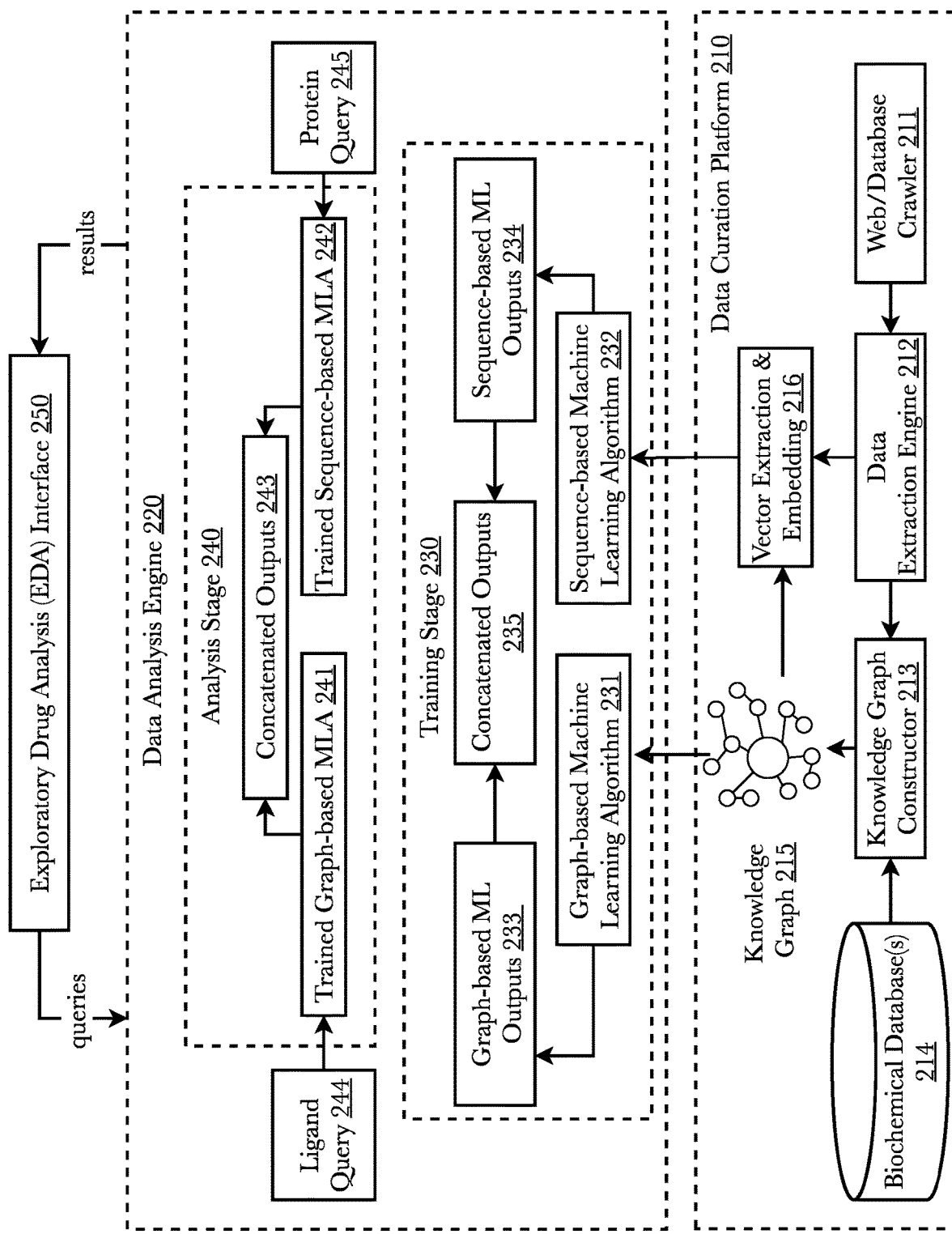
FIG. 2 is a block diagram illustrating an exemplary system architecture for an embodiment of a pharmaceutical research system utilizing combined graph-based and sequence-based prediction of molecule bioactivity.

FIG. 2 is a block diagram illustrating an exemplary system architecture for an embodiment of a pharmaceutical research system utilizing combined graph-based and sequence-based prediction of molecule bioactivity. In this embodiment, the system comprises a data curation platform 210, a data analysis engine 220 comprising a training stage 230 and an analysis stage 240, and an exploratory drug analysis interface 250. The knowledge graph 215 does not refer to a graph representation of the inputs to the model, but to a relational structure of the data in the database itself. The knowledge graph 215 itself is not used as input.

In the data curation platform 210, a web crawler/database crawler 211 is configured to search for and download medical information materials including, but not limited to, archives of published medical literature such as MEDLINE and PubMed, archives of clinical trial databases such as the U.S. National Library of Medicine's ClinicalTrials.gov database and the World Health Organization International Clinical Trials Registry Platform (ICTRP), archives of published dissertations and theses such as the Networked Digital Library of These and Dissertations (NDLTD), archives of grey literature such as the Grey Literature Report, and news reports, conference papers, and individual journals. As the medical information is downloaded, it is fed to a data extraction engine 212 which may perform a series of operations to extract data from the medical information materials. For example, the data extraction engine 212 may first determine a format of each of the materials received (e.g., text, PDFs, images), and perform conversions of materials not in a machine-readable or extractable format (e.g., performing optical character recognition (OCR) on PDFs and images to extract any text contained therein). Once the text has been extracted from the materials, natural language processing (NLP) techniques may be used to extract useful information from the materials for use in analysis by machine learning algorithms. For example, semantic analysis may be performed on the text to determine a context of each piece of medical information material such as the field of research, the particular pharmaceuticals studied, results of the study, etc. Of particular importance is recognition of standardized biochemistry naming conventions including, but not limited to, stock nomenclature, International Union of Pure and Applied Chemistry (IUPAC) conventions, and simplified molecular-input line-entry system (SMILES) and FASTA text-based molecule representations. The data extraction engine 212 feeds the extracted data to a knowledge graph constructor 213, which constructs a knowledge graph 215 based on the information in the data, representing informational entities (e.g., proteins, molecules, diseases, study results, people) as vertices of a graph and relationships between the entities as edges of the graph. Biochemical databases 214 or similar sources of information may be used to supplement the graph with known properties of proteins, molecules, physiological effects, etc. Separately from the knowledge graph 215, vector representations of proteins, molecules, interactions, and other information may be represented as vectors 216, which may either be extracted from the knowledge graph 215 or may be created directly from data received from the data extraction engine 212. The link between the knowledge graph 215 and the data analysis engine 220 is merely an exemplary abstraction. The knowledge graph 215 does not feed into the models directly but rather the data contained in a knowledge graph structured database is used to train the models. The same exemplary abstraction applies between the vector extraction and embedding 216 and the data analysis engine 220.

The data analysis engine 220 utilizes the information gathered, organized, and stored in the data curation platform 210 to train machine learning algorithms at a training stage 230 and conduct analyses in response to queries and return results based on the analyses at an analysis stage 240. The training stage 230 and analysis stage 240 are identical, whereas the analysis stage 240 has already completed training. In this embodiment, the data analysis engine 220 comprises a dual analysis system which combines the outputs of a trained graph-based machine learning algorithm 241 with the outputs of a trained sequence-based machine learning algorithm 242. The trained graph-based machine learning algorithm 241 may be any type of algorithm configured to analyze graph-based data, such as graph traversal algorithms, clustering algorithms, or graph neural networks.

At the training stage 230, information from the knowledge graph 215 is extracted to provide training data in the form of graph-based representations of molecules and the known or suspected bioactivity of those molecules with certain proteins. The graph-based representations, or 3D representations in the 3D case, of the molecules and proteins and their associated bioactivities are used as training input data to a graph-based machine learning algorithm 231, resulting in a graph-based machine learning output 233 comprising vector representations of the characteristics of molecules and their bioactivities with certain proteins. Simultaneously, a sequence-based machine learning algorithm is likewise trained, but using information extracted 216 from the knowledge graph 215 in the form of vector representations of protein segments and the known or suspected bioactivity of those protein segments with certain molecules. The vector representations of the protein segments and their associated bioactivities are used to train the concatenated outputs 235, as well as the machine learning algorithms 231, 232, 233, 234. In this embodiment, the graph-based machine learning outputs 233 and the sequence-based machine learning outputs 234 are concatenated to produce a concatenated output 235, which serves to strengthen the learning information from each of the separate machine learning algorithms. In this and other embodiments, the concatenated output may be used to re-train both machine learning algorithms 233, 234 to further refine the predictive abilities of the algorithms.

At the analysis stage, a query in the form of a target ligand 244 and a target protein 245 are entered using an exploratory drug analysis (EDA) interface 250. The target ligand 244 is processed through the trained graph-based machine learning algorithm 241 which, based on its training, produces an output comprising a vector representation of the likelihood of interaction of the target ligand 244 with certain proteins and the likelihood of the bioactivity resulting from the interactions. Similarly, the target protein 245 is processed through the trained sequence-based machine learning algorithm 242 which, based on its training, produces an output comprising a vector representation of the likelihood of interaction of the target protein 245 with certain ligands and the likelihood of the bioactivity resulting from the interactions. The results may be concatenated 243 to strengthen the likelihood information from each of the separate trained machine learning algorithms 241, 242.

Figure 3:
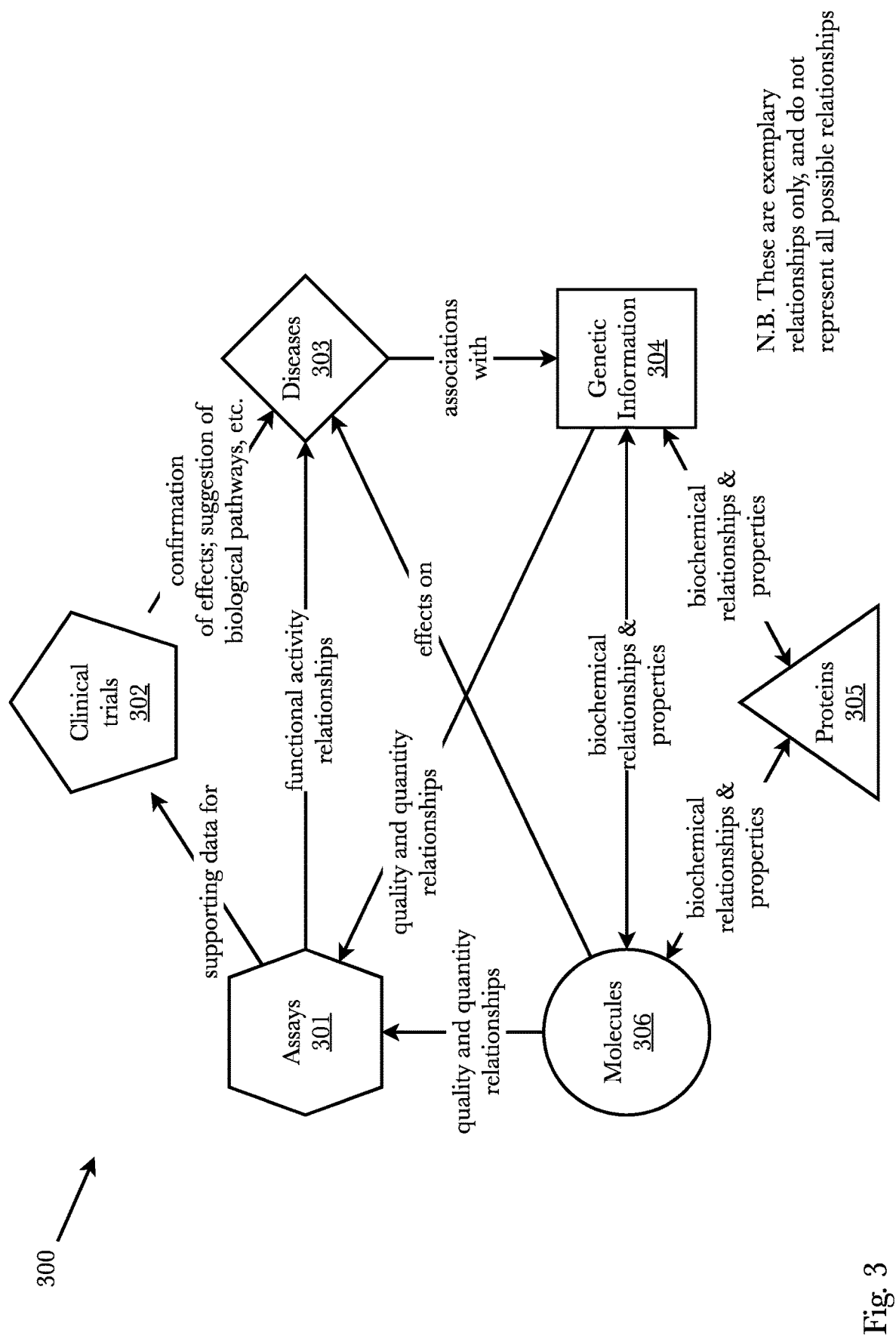
FIG. 3 is a relational diagram illustrating several types of information that may be included in a knowledge graph for a pharmaceutical research system and exemplary relations between those types of information.

FIG. 3 is a relational diagram 300 illustrating several types of information that may be included in a knowledge graph for a pharmaceutical research system and exemplary relations between those types of information. In this example, six types of information are shown with indications of certain relevant relationships and interactions that may be represented in a knowledge graph containing these types of information. The six types of information in this example are chosen to be of particular relevance to pharmaceutical research, and in particular to the analysis of, and prediction of, biochemical properties of proteins and ligands as they relate to disease. Proteins 305 and molecules (ligands) 306 are the primary types of information, as their biochemical relationships and properties determine effects on diseases 303. Genetic information 304 will have an influence on the production of specific proteins 305 and the association with certain diseases 303. Assays 301 will provide information about the quality and quantity relationships of proteins 350 and molecules 306, which provides supporting data for clinical trials 302 and for functional activity relationships with certain diseases 303. Clinical trials 302 provide confirmation of physiological effects and suggestion of biological pathways related to diseases. While this simplified diagram does not purport to show all types of data that may be included or all relationships that may be relevant, it does show certain important types of data and major relevancies that may be included in a knowledge graph to be used for a pharmaceutical research system.

Figure 4:
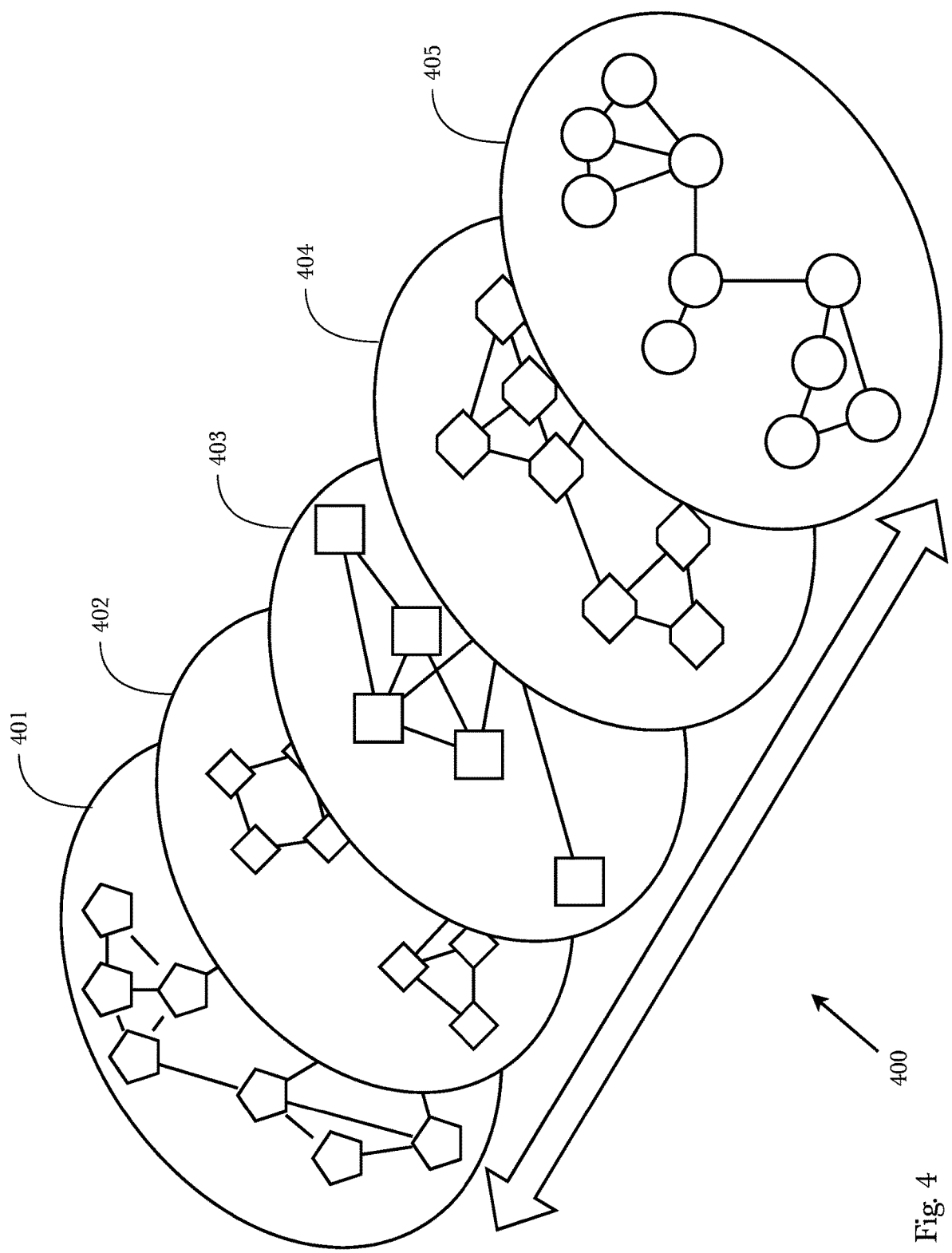
FIG. 4 is a diagram illustrating the conceptual layering of different types of information in a knowledge graph.

FIG. 4 is a diagram illustrating the conceptual layering 400 of different types of information in a knowledge graph. While knowledge graphs are not necessarily constructed in layers, each type of information included in a knowledge graph may be conceived as a layer of information in the knowledge graph and each layer may be analyzed to determine clustering and other relationships within the layer. For example, proceeding with the types of information shown in FIG. 3, the knowledge graph can be conceived of as having layers for clinical trials 401, diseases 402, genetic information 403, assays 404, molecules 405, etc. Relationships such as clustering can be seen at each layer, and can be analyzed separately, if necessary. However, in a knowledge graph, connections between the information at each layer are made and relationships between the information at each layer can be analyzed.

Figure 5:
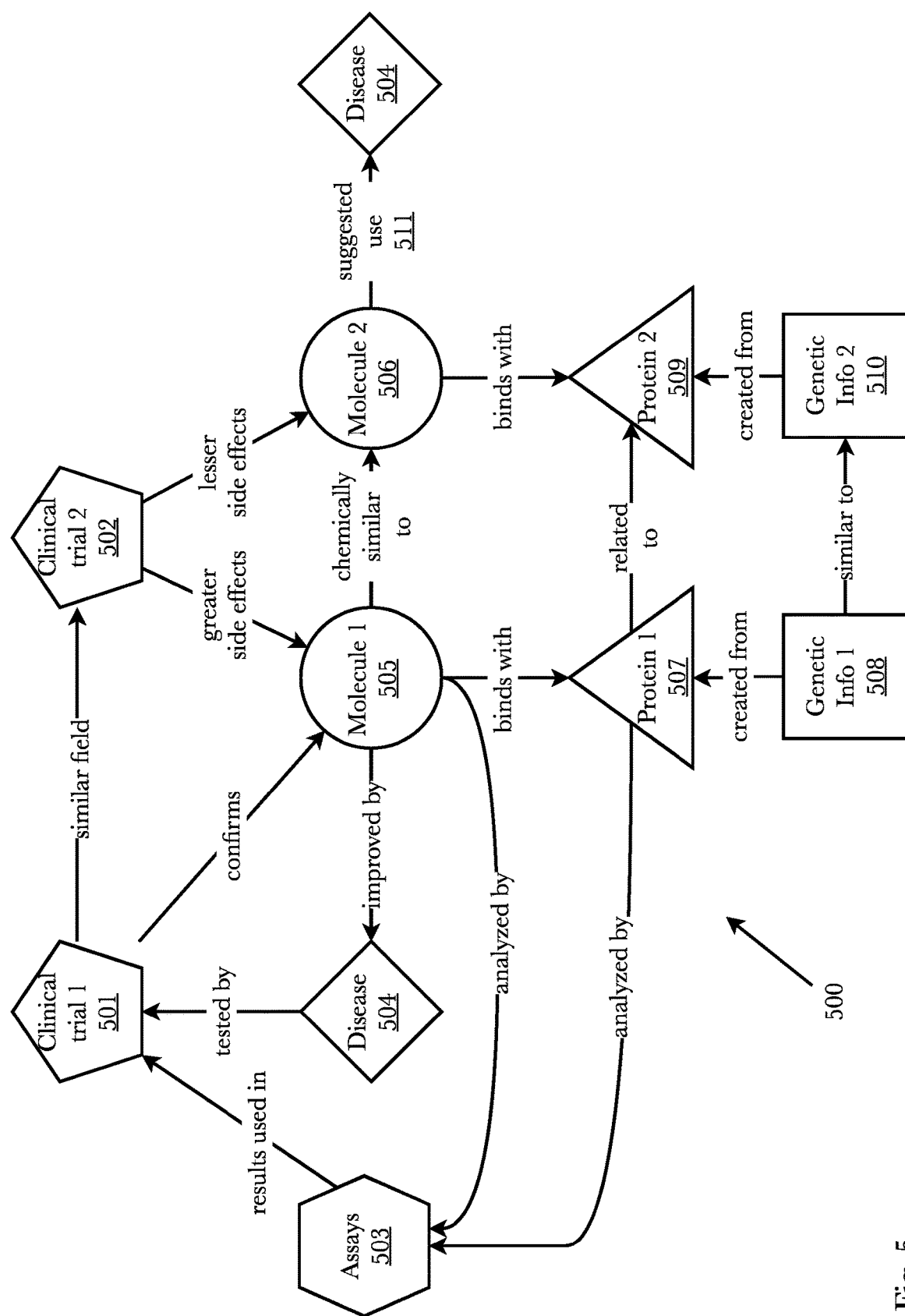
FIG. 5 is a relational diagram illustrating the use of a knowledge graph to predict usefulness of a molecule in treating a disease.

FIG. 5 is a relational diagram illustrating the use of a knowledge graph to predict usefulness of a molecule in treating a disease 500. In this example, a first molecule 505 is known to bind with a first protein 507 which is produced from a first set of genetic information 508. A clinical trial 501 confirmed that the first molecule 505 is effective in treating a disease 504. The clinical trial 501 used information from assays 503 that were performed on the first molecule 505 and the first protein 507. A query has been submitted to the system to identify a second molecule 506 that may also be effective in treating 511 the same disease 504, but with fewer side effects. Using a knowledge graph containing the types of information shown in FIG. 3, and a graph-based machine learning algorithm, the system identifies a second molecule 506 that binds with a second protein 509 which is produced from a second set of genetic information 510. The system determines a number of similarities and relationships between the first molecule 505 and the second molecule 506, including that the first molecule 505 is chemically similar to the second molecule 506, the protein 507 with which the first molecule 505 binds is related to the second protein 509 with which the second molecule 506 binds, and the genetic information (DNA strands) 508 that produces the first protein 507 are similar to the genetic information 510 that produces the second protein 509. Thus, the system determines that the second molecule 506 is likely to have a similar effect on the disease 504 as the first molecule 505. Further, the system identifies a second clinical trial 502 that suggests that the second molecule 506 has lesser side effects than the first molecule 505. As the second molecule 506 meets the query criteria, it is returned as a response to the query.

Figure 6:
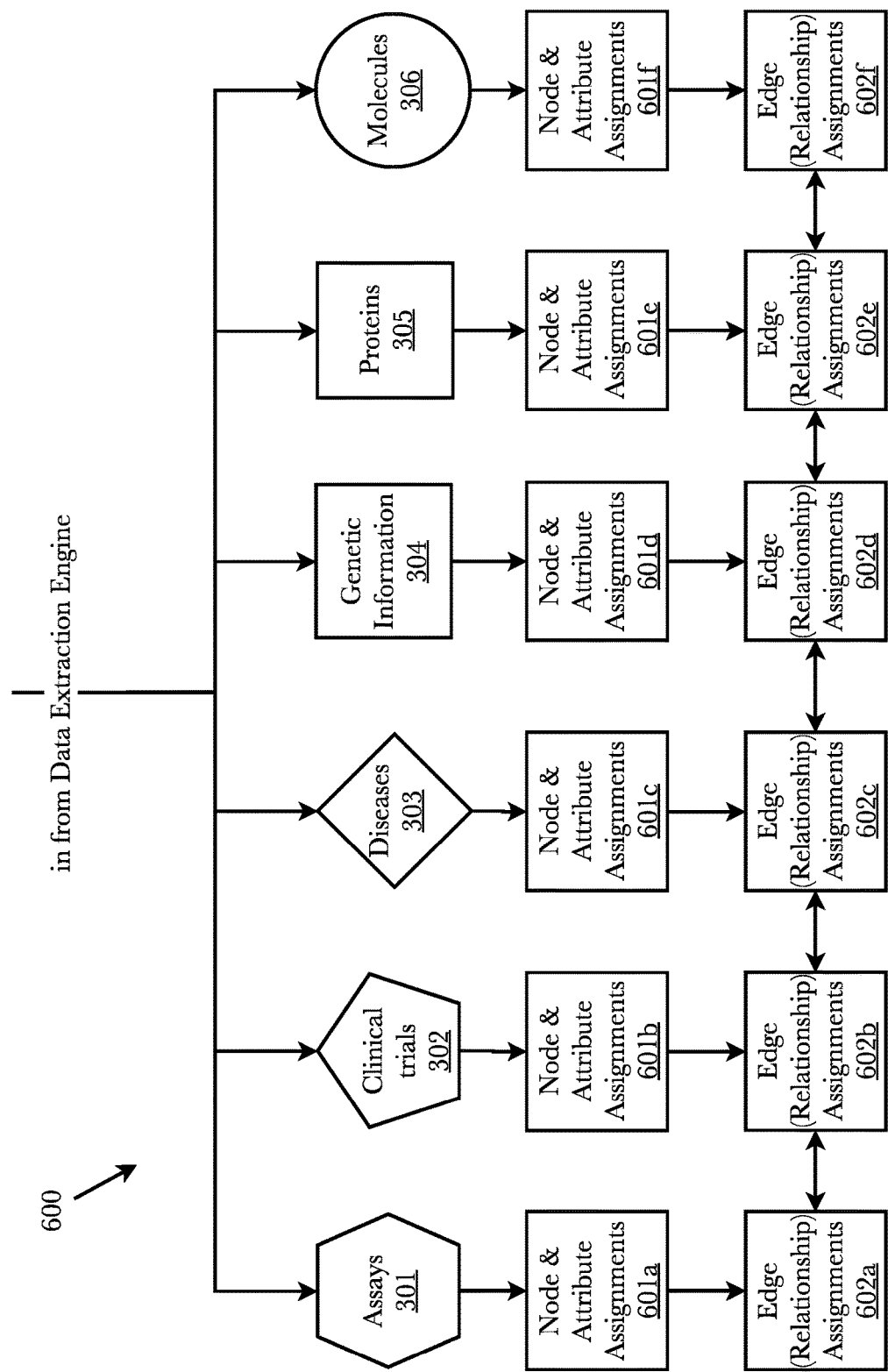
FIG. 6 is a diagram illustrating an exemplary process for combining various types of information into a knowledge graph suitable for a pharmaceutical research system.

FIG. 6 is a diagram illustrating an exemplary process 600 for combining various types of information into a knowledge graph suitable for a pharmaceutical research system. As data is received from a data extraction engine in each of several categories of data (in this example, six categories: assays 301, clinical trials 302, diseases 303, genetic information 304, proteins 305, and molecules 306) nodes are assigned to each entity identified in each category and attributes of the entity are assigned to the node 601a-f. Attributes of the nodes/entity are information describing the characteristics of the nodes/entity. For example, in some embodiments, attributes of nodes related to molecules are in the form of an adjacency matrix which represents the molecule as relationships between the atoms of the molecule. After nodes have been assigned to all identified entities 601a-f, the relationships between entities are assigned, both within the category of knowledge and between all other categories of knowledge 602a-f. As a simple example of the process, assume that a certain molecule 306 is identified during data extraction. A node is created for the molecule and attributes are assigned to the molecule/node in the form of an adjacency matrix representing the molecule as a series of relationships between the atoms of the molecule. Through a series of assays 301 and clinical studies 302, it is known that the molecule binds with a particular protein 305, and is effective in treating a certain disease 303, to which individuals with certain genetic information 304 are susceptible. Nodes are assigned to each of the assays 301, clinical trials 302, diseases 303, proteins 305, and genetic information 304 identified as being associated with the molecule, and edges are established between the nodes reflecting the relevant relationships such as: the molecule binds with the protein, the genetic information is associated with the disease, the clinical trials indicate that the disease is treatable by the molecule, and so on.

Figure 7:
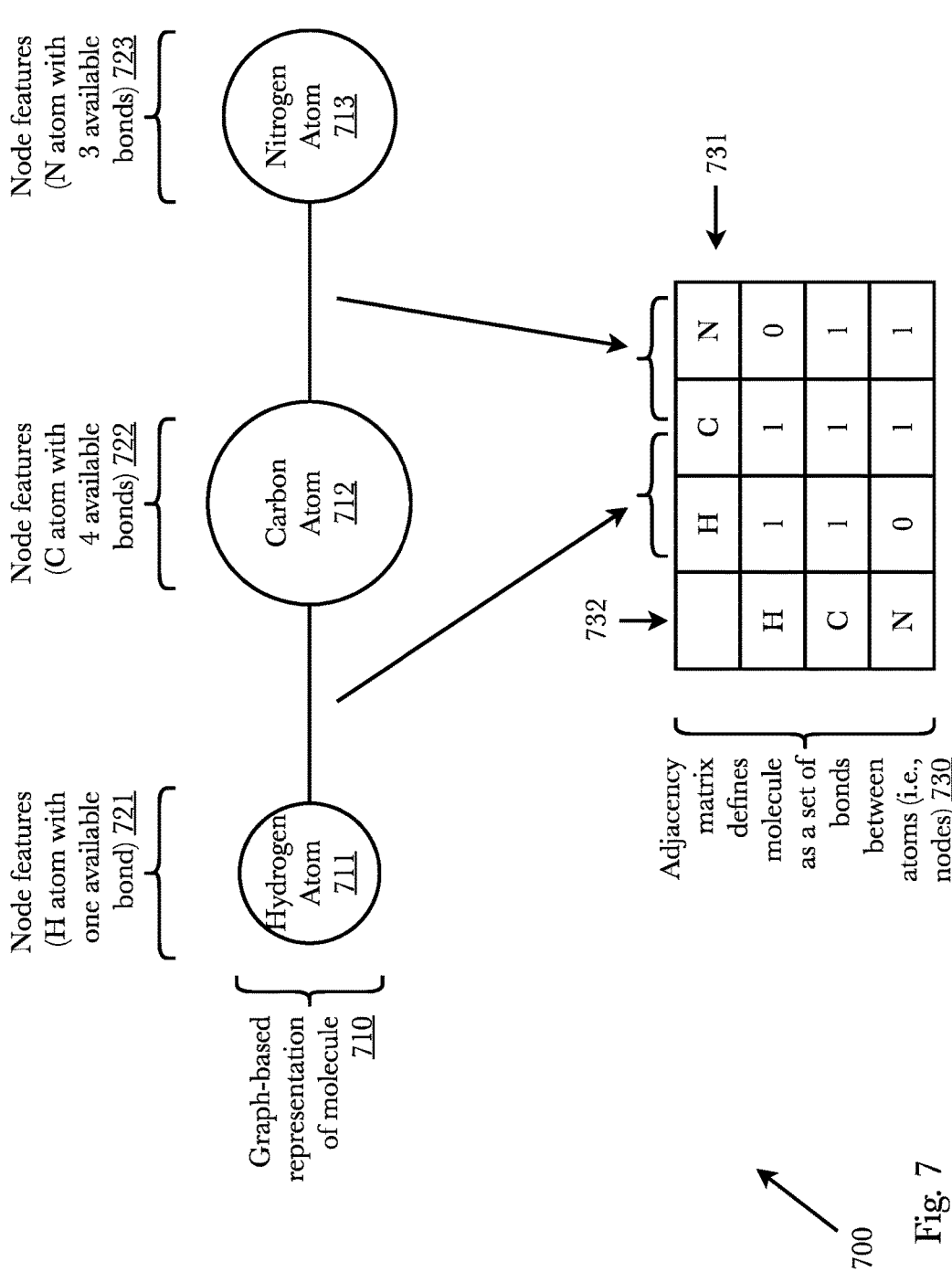
FIG. 7 is a diagram illustrating an exemplary graph-based representation of molecules as simple relationships between atoms using a matrix of adjacencies.

FIG. 7 is a diagram illustrating an exemplary graph-based representation of molecules as simple relationships between atoms using a matrix of adjacencies 700, wherein atoms are represented as nodes and bonds between the atoms are represented as edges. Representation of molecules as a graph is useful because it provides a molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule. Each molecule represented in the matrix comprises a dimensionality and features that describe the type of bond between the atoms. According to one embodiment, all bonds within the graph hold the same value, e.g., 1. However, in other embodiments, bonds may be differentiated such as hydrogen bonds having a value of 3, or by having the bond feature dimension exist in each cell.

In this example, a simple hydrogen cyanide molecule is shown as a graph-based representation 710. A hydrogen cyanide molecule consists of three atoms, a hydrogen atom 711, a carbon atom 712, and a nitrogen atom 713. Its standard chemical formula is HCN. Each atom in the molecule is shown as a node of a graph. The hydrogen atom 711 is represented as a node with node features 721 comprising the atom type (hydrogen) and the number of bonds available (one). The carbon atom 712 is represented as a node with node features 722 comprising the atom type (carbon) and the number of bonds available (four). The nitrogen atom 713 is represented as a node with node features 723 comprising the atom type (nitrogen) and the number of bonds available (three). The node features 721, 722, 723 may each be stated in the form of a matrix.

The relationships between the atoms in the molecule are defined by the adjacency matrix 730. The top row of the adjacency matrix 731 shows all of the atoms in the molecule, and the left column of the matrix 732 shows a list of all possible atoms that can be represented by the matrix for a given set of molecules. In this example, the top row 731 and left column 732 contain the same list of atoms, but in cases where multiple molecules are being represented in the system, the left column may contain other atoms not contained in the particular molecule being represented. The matrix shows, for example, that the hydrogen atom 711 is connected to the carbon atom 712 (a "1" at the intersection of the rows and columns for H and C) and that the carbon atom 712 is connected to the nitrogen atom 713 (a "1" at the intersection of the rows and columns for C and N). In this example, each atom is also self-referenced (a "1" at the intersection of the rows and columns for H and H, C and C, and N and N), but in some embodiments, the self-referencing may be eliminated. In some embodiments, the rows and columns may be transposed (not relevant where the matrix is symmetrical, but relevant where it is not).

Figure 8:
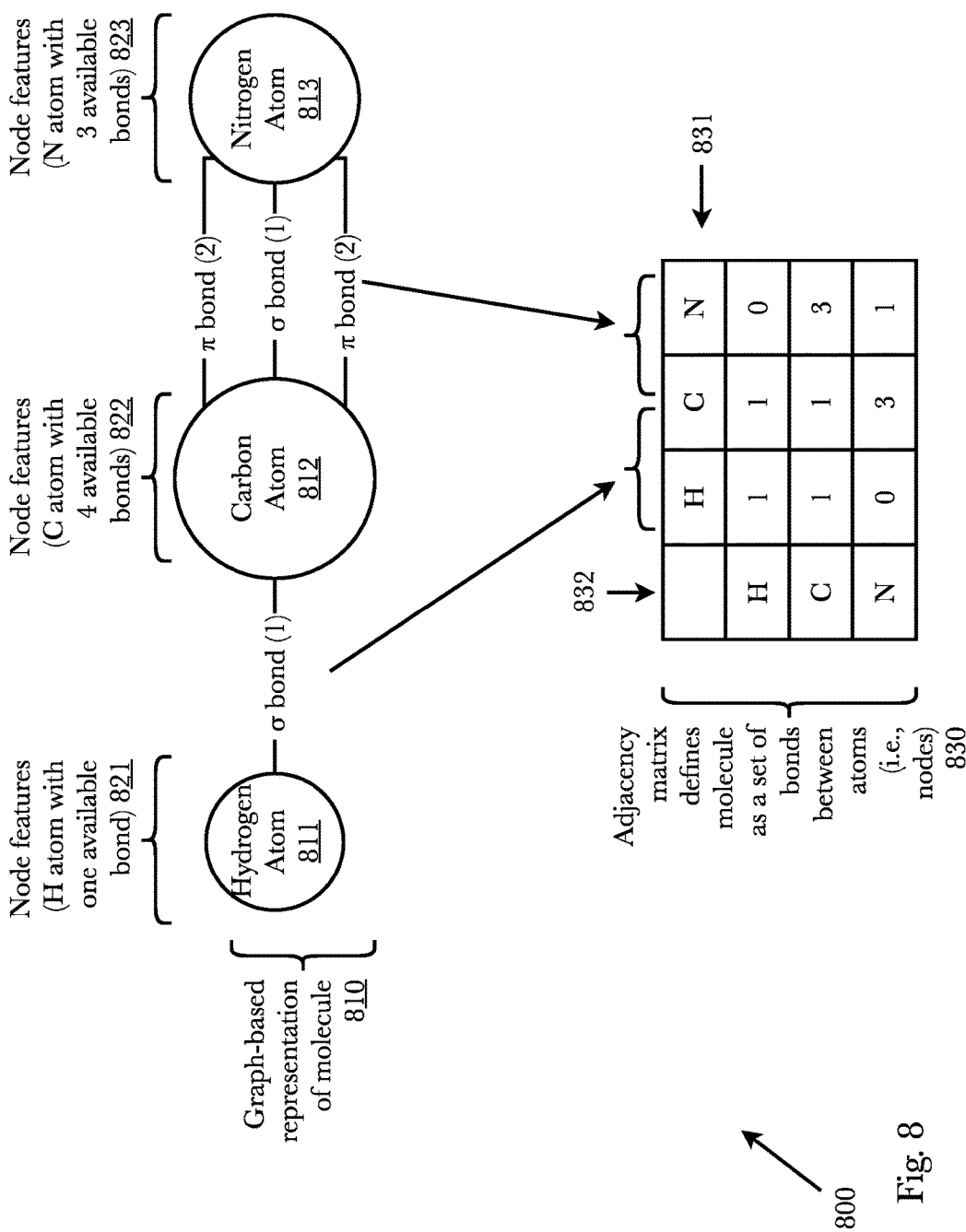
FIG. 8 is a diagram illustrating an exemplary graph-based representation of molecules as relationships between atoms using a matrix of adjacencies wherein the type bonds are distinguished.

FIG. 8 is a diagram illustrating an exemplary graph-based representation of molecules as relationships between atoms using a matrix of adjacencies 800, wherein atoms are represented as nodes and bonds between the atoms are represented as edges, and wherein the type and number of bonds are distinguished. Representation of molecules as a graph is useful because it provides a molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule.

In this example, a simple hydrogen cyanide molecule is shown as a graph-based representation 810. A hydrogen cyanide molecule consists of three atoms, a hydrogen atom 811, a carbon atom 812, and a nitrogen atom 813. Its standard chemical formula is HCN. Each atom in the molecule is shown as a node of a graph. The hydrogen atom 811 is represented as a node with node features 821 comprising the atom type (hydrogen) and the number of bonds available (one). The carbon atom 812 is represented as a node with node features 822 comprising the atom type (carbon) and the number of bonds available (four). The nitrogen atom 813 is represented as a node with node features 823 comprising the atom type (nitrogen) and the number of bonds available (three). The node features 821, 822, 823 may each be stated in the form of a matrix.

The relationships between the atoms in the molecule are defined by the adjacency matrix 830. The top row of the adjacency matrix 831 shows all of the atoms in the molecule, and the left column of the matrix 832 shows a list of all possible atoms that can be represented by the matrix for a given set of molecules. In this example, the top row 831 and left column 832 contain the same list of atoms, but in cases where multiple molecules are being represented in the system, the left column may contain other atoms not contained in the particular molecule being represented. The matrix shows, for example, that the hydrogen atom 811 is connected to the carbon atom 812 (a "1" at the intersection of the rows and columns for H and C) and that the carbon atom 812 is connected to the nitrogen atom 813 (a "3" at the intersection of the rows and columns for C and N). In this example, the number of bonds between atoms is represented by the digit in the cell of the matrix. For example, a 1 represents a single bond, whereas a 3 represents a triple bond. In this example, each atom is also self-referenced (a "1" at the intersection of the rows and columns for H and H, C and C, and N and N), but in some embodiments, the self-referencing may be eliminated. In some embodiments, the rows and columns may be transposed (not relevant where the matrix is symmetrical, but relevant where it is not).

Figure 9:
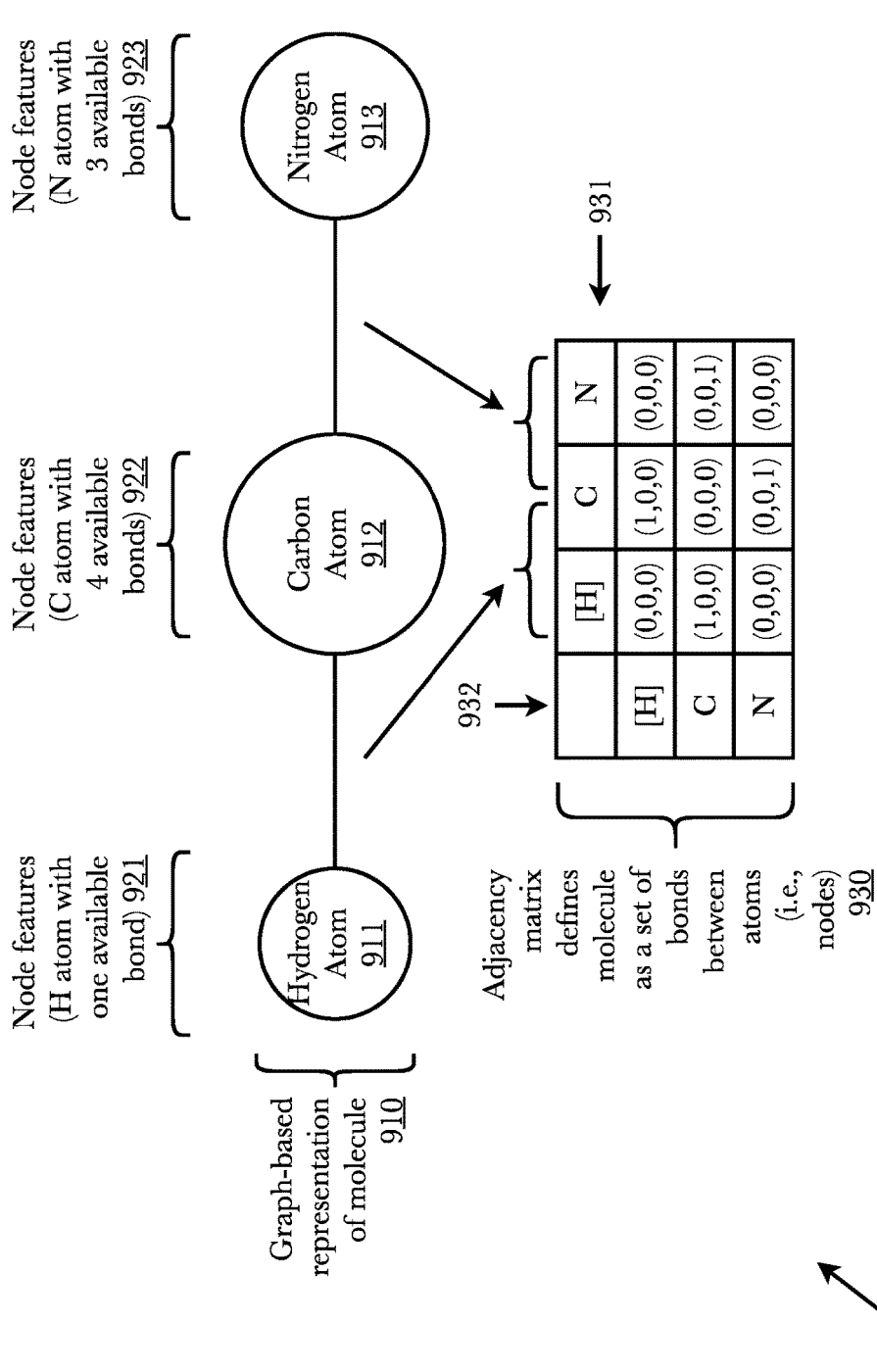
FIG. 9 is a diagram illustrating an exemplary graph-based representation of molecules as relationships between atoms using a matrix of adjacencies using SMILES string encoding and one-hot vectors indicating the types of bonds between atoms.

FIG. 9 is a diagram illustrating an exemplary graph-based representation of molecules as relationships between atoms using a matrix of adjacencies 900, wherein atoms are represented as nodes and bonds between the atoms are represented as edges, and wherein the matrix of adjacencies uses a SMILES string encoding of the molecule and one-hot vector representations of the type of bonds between atoms in the molecule. Representation of molecules as a graph is useful because it provides a molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule.

In this example, a simple hydrogen cyanide molecule is shown as a graph-based representation 910. A hydrogen cyanide molecule consists of three atoms, a hydrogen atom 911, a carbon atom 912, and a nitrogen atom 913. Its SMILES representation text string is [H]C#N, with the brackets around the H indicating an element other than an organic element, and the # representing a triple bond between the C and N. Each atom in the molecule is shown as a node of a graph. The hydrogen atom 911 is represented as a node with node features 921 comprising the atom type (hydrogen) and the number of bonds available (one). The carbon atom 912 is represented as a node with node features 922 comprising the atom type (carbon) and the number of bonds available (four). The nitrogen atom 913 is represented as a node with node features 923 comprising the atom type (nitrogen) and the number of bonds available (three). The node features 921, 922, 923 may each be stated in the form of a matrix 930.

In this example, the top row 931 and left column 932 contain the same list of atoms, but in cases where multiple molecules are being represented in the system, the left column may contain other atoms not contained in the particular molecule being represented. The matrix shows, for example, that the hydrogen atom 811 is connected to the carbon atom 812 with a single bond (the one-hot vector "(1,0,0)" at the intersection of the rows and columns for H and C) and that the carbon atom 812 is connected to the nitrogen atom 813 with a triple bond (the one-hot vector "(0,0,1)" at the intersection of the rows and columns for C and N). In this example, the number of bonds between atoms is represented by a one-hot vector in the cell of the matrix. For example, a 1 in the first dimension of the vector (1,0,0) represents a single bond, whereas a 1 in the third dimension of the vector (0,0,1) represents a triple bond. In this example, self-referencing of atoms is eliminated, but self-referencing may be implemented in other embodiments, or may be handled by assigning self-referencing at the attention assignment stage. In some embodiments, the rows and columns may be transposed (not relevant where the matrix is symmetrical, but relevant where it is not).

Figure 14:
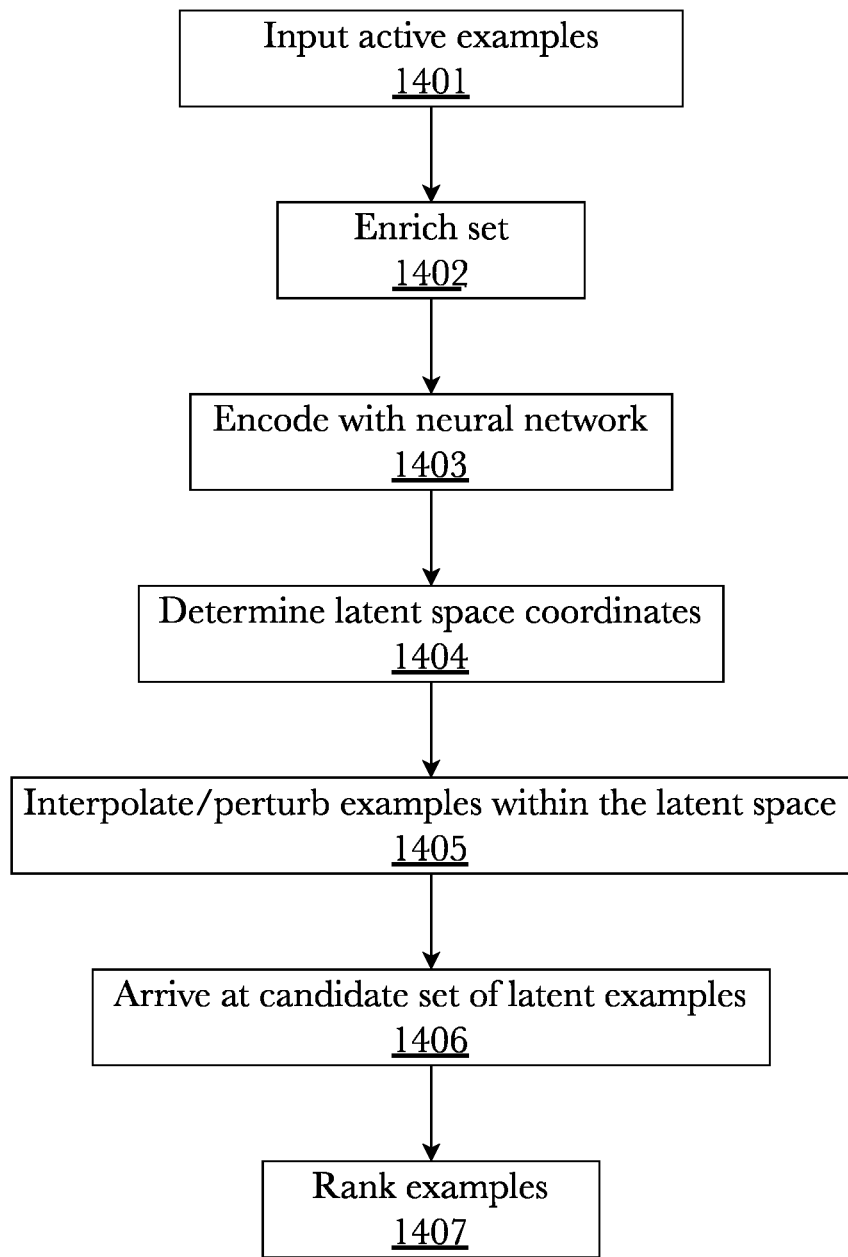
FIG. 14 is a flow diagram illustrating an exemplary method for active example generation.

FIG. 14 is a flow diagram illustrating an exemplary method for active example generation. According to a general methodology description, generating active examples (i.e., chemically valid ligand-receptor pairs) is performed by the first step of gathering known active examples from databases, web-crawlers, and other sources previously described in past figures 1401. Active examples may then be enriched to fill in missing data, supplement, append or otherwise enhance the training data 1402. A specific example of enrichment may be finding similar compounds with the same properties as a target molecule or that responds to known ligands in the same fashion. With the enhanced training data (i.e., enriched active examples) gathered, it is fed into a neural network (NN) 1403. A consideration must be noted that many machine learning algorithms exist, and that this method may work with many NN models or other machine learning algorithms and is not limited to the ones disclosed herein.

The neural networks build a model from the training data. In the case of using an autoencoder (or a variational autoencoder), the encoder portion of the neural network reduces the dimensionality of the input molecules, learning a model from which the decoder portion recreates the input molecule. The significance of outputting the same molecule as the input is that the decoder may then be used as a generative function for new molecules. One aspect of a generative decoder module is that the learned model (i.e., protein-ligand atom-features according to one embodiment) lies in a latent space 1404. Sampled areas of the latent space are then interpolated and perturbed 1405 to alter the model such that new and unique latent examples 1406 may be discovered. Other ways to navigate the latent space exist, Gaussian randomization as one example, that may be used in other embodiments of the invention. Furthermore, libraries, other trained models, and processes exist that may assist in the validation of chemically viable latent examples within the whole of the latent space; processing the candidate set of latent examples through a bioactivity model, as one example 1407.

Regarding retrosynthesis for de novo drug design, two approaches are described below. A first approach begins with preprocessing all the SMILES representations for reactants and products to convert to canonical form (SMILES to Mol & Mol to SMILES through a cheminformatics toolkit), remove duplicates & clean the data, augmenting SMILE equivalents via enumeration. Then, transformer models are used with multiple attention heads and a k-beam search is set up. Further, the models are conformed by optimizing on producing long-term reactants, ensuring the models are robust to different representations of a molecule, providing intrinsic recursion (using performers), and including further reagents such as catalysts and solvents.

A second approach begins with augmenting the transformer model with a hyper-graph approach. Starting with an initial node of the graph as the query molecule and recursively: the molecule with highest upper-bound confidence (UCB) score is selected (specifically, the UCB is adapted to trees generation UCT), the node is expanded (if this node is not terminal), and expansions from that node are simulated to recover a reward. Rewards are backpropagated along the deque of selected nodes, and the process is repeated until convergence. Here UCB is used as a form of balancing exploration-exploitation, where X is the reward, n is the number of times the parent node has been visited, j denotes the child node index, and $C_p$ (>0) is an exploration constant. In one embodiment, the model may be constrained to a rewarding a node when its children are accessible, wherein other embodiments may use rewards such as molecular synthesis score, Log P, synthesis cost, or others known in the art.

$$UCT = \overline{X}_j + 2C_p \sqrt{\frac{2\ln n}{n_j}}$$

According to one aspect of the second approach, transformer models are optimized so that they produce a molecule that can be formed with another molecule. However, these models should be optimized with the aim of producing reactants which are going to recursively deconstruct into accessible molecules. Hence, adding reinforcement learning finetuning to force the transformer model to not only produce reactants which are plausible but to produce reactants which lead to favorable retrosynthetic routes.

Figure 15:
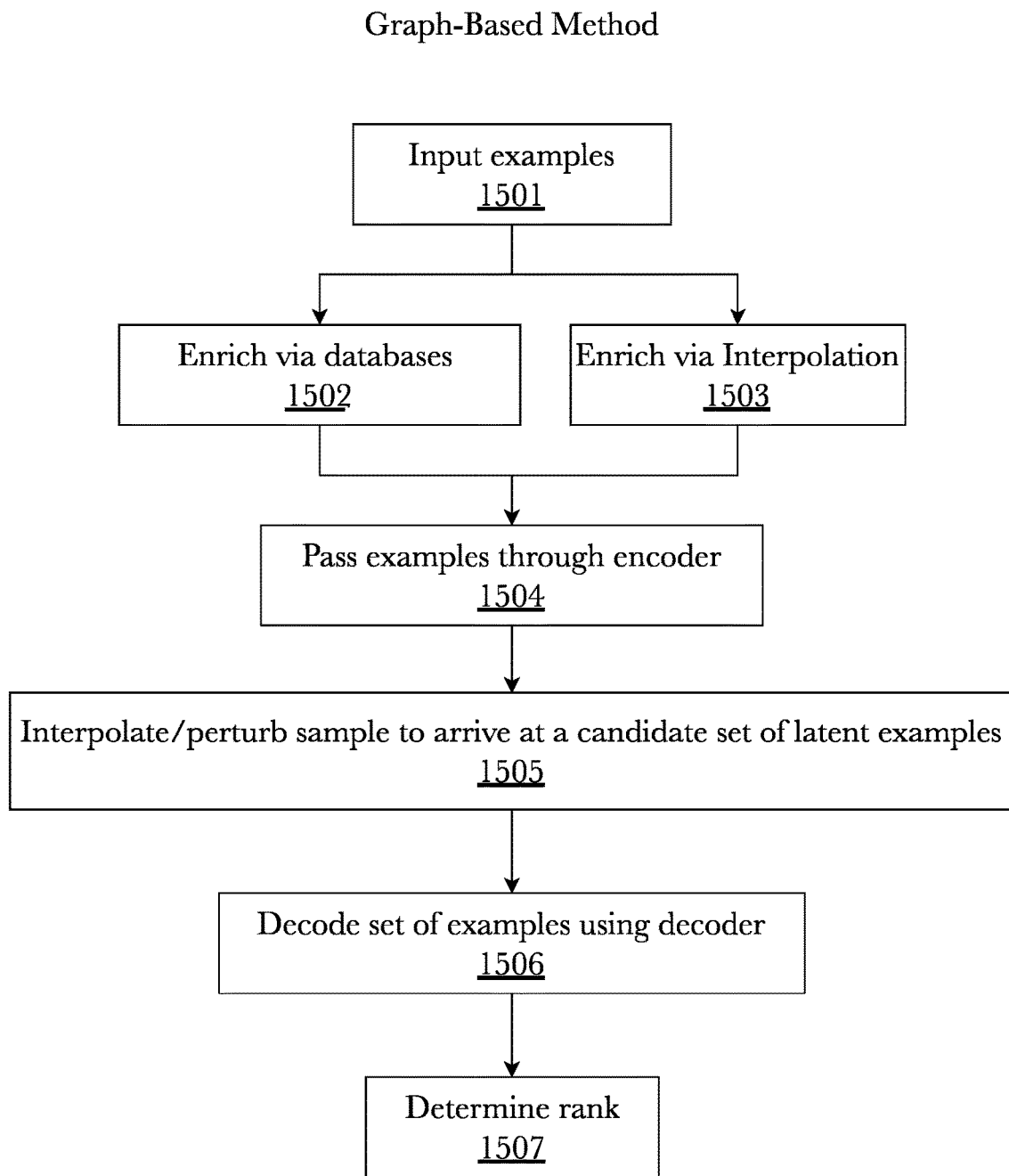
FIG. 15 is a flow diagram illustrating an exemplary method for active example generation using a graph-based approach.

FIG. 15 is a flow diagram illustrating an exemplary method for active example generation using a graph-based approach. According to a first preferred embodiment of active example generation, where a graph-based method is used, active molecules are input (via a WebApp according to one aspect) as SMILES representations 1501. This involves training an autoencoder to obtain a fixed-dimensional representation of SMILES and may further be reused for the bioactivity model. Additionally, standard SMILES encoding fails to capture all pertinent information relating to the atoms (e.g., bond length). Consequently, enumeration may be used to improve the standard SMILES model where enumeration is an equivalent to data augmentation via rotation, therefore by having different SMILES representations of the same molecule from different orientations the missing information is captured. Other enumeration methods may be used where data is necessary but missing. The enumerated SMILES encoding used may comprise one-hot encodings of atom type, atom degree, valence, hybridization, and chirality as well as formal charge and number of radical electrons. Bond types (single, double, triple, and aromatic), bond length, and bond conjugation with ring and stereo features are also captured.

Enrichment of the input data may be performed by searching through data sets for similar compounds through specific tags (e.g., anti-viral) 1502. Additionally, the enrichment process may be used if the training data lacks any descriptive parameters, whereby databases, web-crawlers, and such may fill in the missing parameters 1502. Enrichment may also occur where data is sparse by interpolating between known molecules 1503. This enriched training data is then captured in node and edge feature matrices. Some embodiments may use matrices comprising a node feature matrix, N, of shape (No_Atoms, No_Features_Atom) and edge feature (adjacency) tensor, A, of shape (No_Atoms, No_Atoms, No_Features_Bond). A reminder to the reader that a tensor's rank is its matrix dimensionality.

Figure 20:
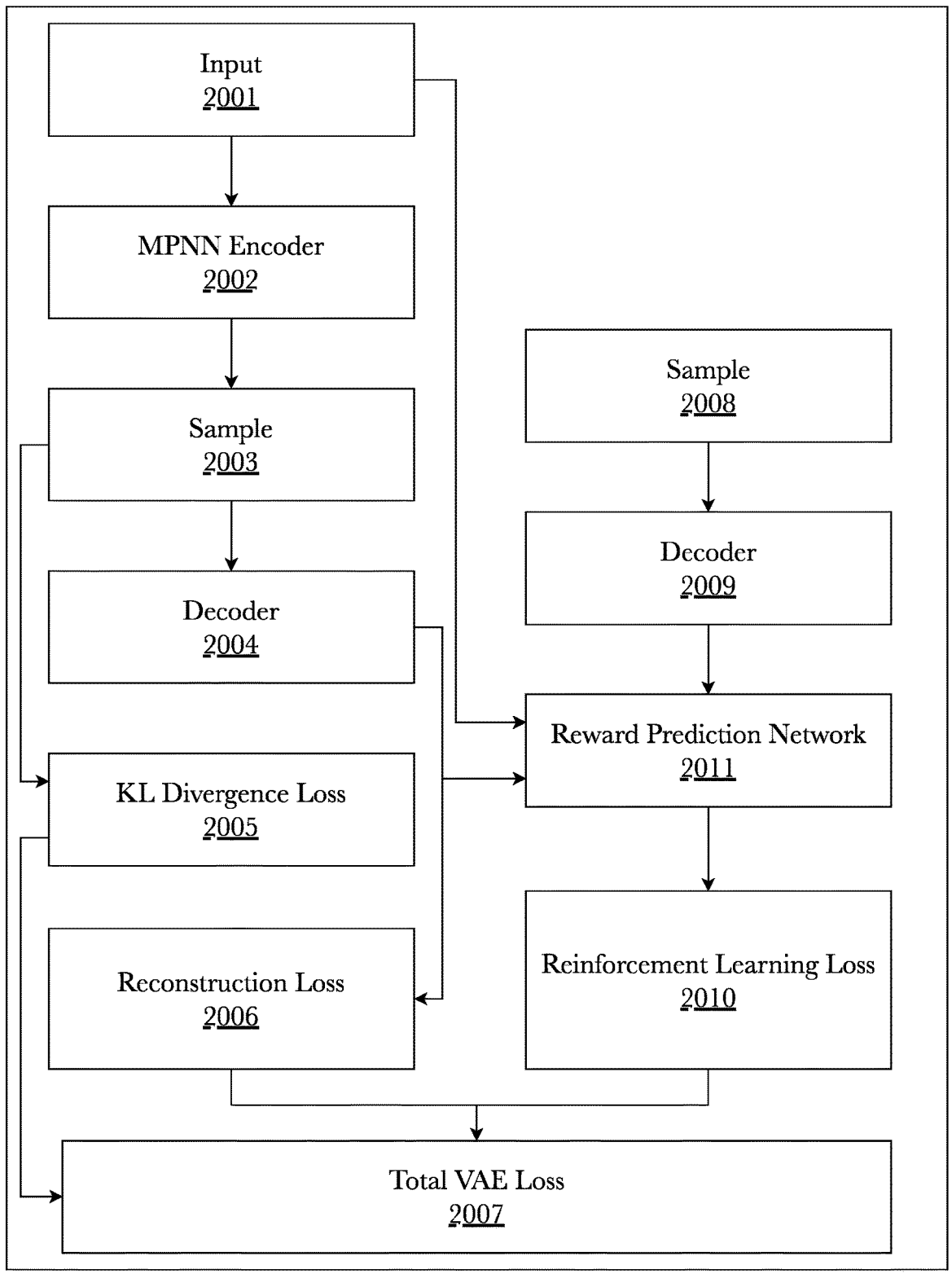
FIG. 20 is a block diagram of an overall model architecture of a system for de novo drug discovery according to one embodiment.

The next step is to pass examples through a variational autoencoder (VAE) together with a reinforcement learning component to build the full model 1504 (See FIG. 20). The encoder of this embodiment consists of a message passing neural network, which given node and edge features is designed to learn a hidden representation of a molecule (i.e., a readout vector). This is done by continuously aggregating neighboring node and edge information through a process called message passing. The readout vector is subsequently split into the mean and variance vectors which serve and as the parameters of the posterior distribution from the sampling. The model may learn a latent distribution that governs molecular properties and provide a decoder which can construct chemically valid molecules from samples of the prior 1505. Latent samples are passed through a sequence of dense layers, after which the two different matrices (node feature matrix, N and edge feature tensor) are used to reconstruct the node feature and edge feature matrices. Keeping with the example described in the paragraph above, these two matrices must have the shapes of (No Atoms, No Node Features) and (No Atoms, No Atoms, No Edge Features) respectively. This may be enforced by using a maximum number of allowed atoms to reconstruct. Further, an additional entry for each of the encoded feature distributions may be allowed, which represents the possibility of No Atom/No Feature. The node and edge feature matrices are compared using an approximate graph matching procedure which looks at atom types, bond types, atom-bond-atom types.

Reinforcement learning may be used in parallel to provide an additional gradient signal, checking that decoded molecules are chemically valid using cheminformatics toolkits. In particular, samples from the prior distribution (N (0,1)) as well as posterior distribution (N (mean, std)) are decoded 1506 and their validity is evaluated 1507. If the cheminformatics toolkit is non-differentiable, then a reward prediction network (a separate MPNN encoder) that is trained to predict the validity of an input graph may be used. Together, these components provide an end to end, fully differentiable framework for training. Other choices for data can be QM9, or any other database that is considered valid.

According to one aspect, in order to make use of more molecules, alternative reconstructability criteria may be used to ensure a chemical similarity threshold instead of perfect reconstruction. For example, encoding and decoding several times and using a molecule if its reconstruction has a chemical similarity above a certain threshold may result in a greater number of reconstructable molecules.

New molecules may also be generated via perturbation, wherein the encodings of the active molecules (i.e., the mean and log(sigma$^2$) values) are taken and Gaussian noise is added to them. A sample from the new (mean, log(sigma$^2$)) values are taken and decoded to derive novel molecules. An important hyperparameter is the magnitude of the Gaussian noise that is added to latent vectors. It is also possible to dynamically adjust the perturbation coefficient, for example, increasing it if the proportion of new molecules is low and decreasing it otherwise.

New molecules may also be generated via interpolation. To generate via interpolation, two random reconstructable molecules are taken, computed together for an interpolation of their latent (mean, log(sigma$^2$)) representations with a random interpolation coefficient, and then decoded to get a new molecule. Generative Adversarial Networks (GANs) excel at interpolation of high dimensional inputs (e.g., images). According to one aspect, the dimension of p(z) corresponds to the dimensionality of the manifold. A method for latent space shaping is as follows: Converge a simple autoencoder on a large z, find the Principal Component Analysis (PCA) which corresponds to the 95th percentile of the "explained variance", and choose a z within that spectrum (i.e., if the first 17 components of the latent space to represent 95% of the data, choosing z of 24 is a good choice). Now, for high dimensional latent spaces with a Gaussian prior, most points lie within a hyper spherical shell. This is typically the case in multi-dimensional gaussians. To that end, slerp (spherical linear interpolation) interpolation may be used between vectors v1 and v2. Therefore, interpolation is a direct way to explore the space between active molecules.

Figure 16:
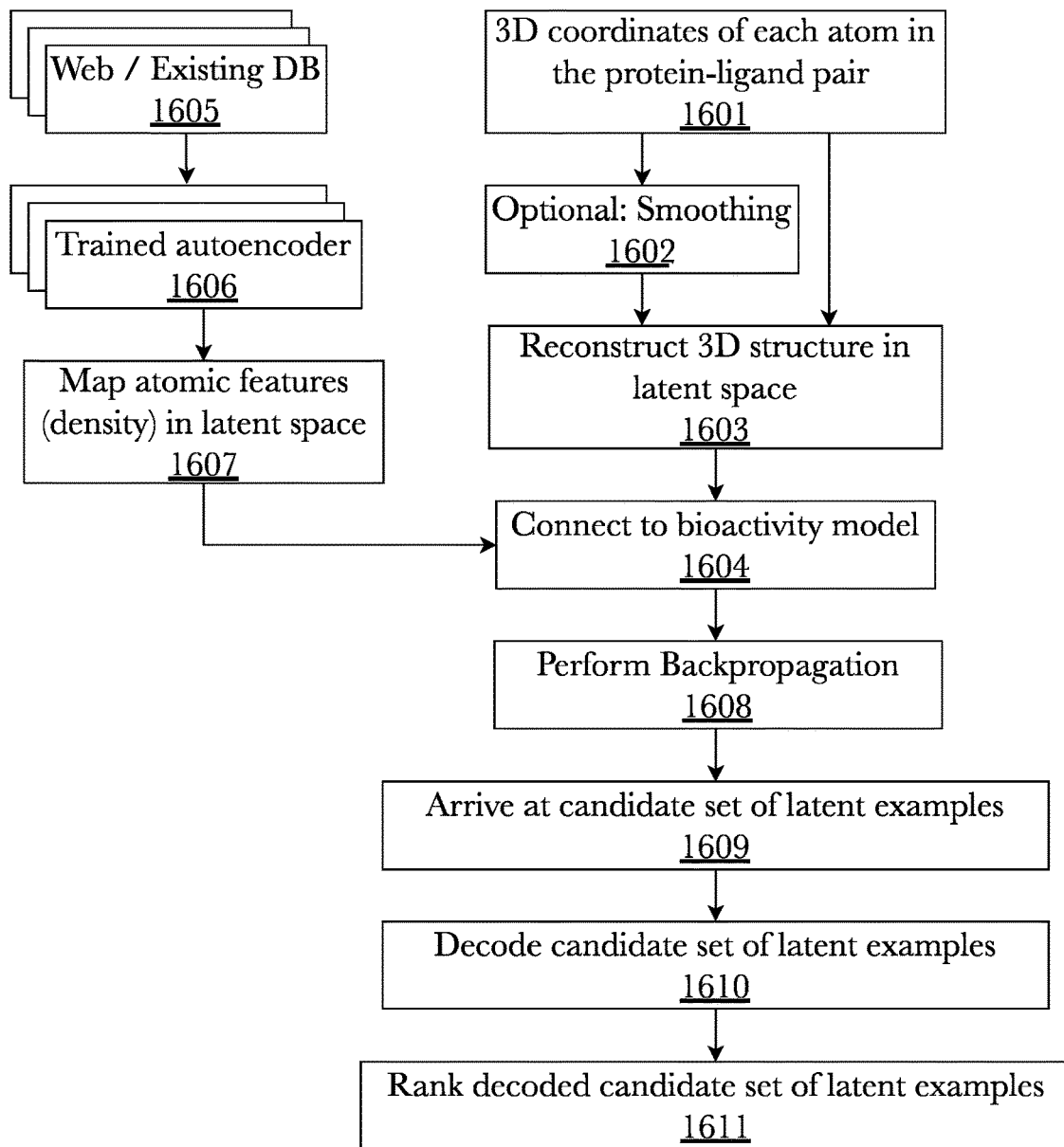
FIG. 16 is a flow diagram illustrating an exemplary method for active example generation using a 3D CNN approach.

FIG. 16 is a flow diagram illustrating an exemplary method for active example generation using a 3D CNN approach. According to an embodiment of active example generation, a 3-dimensional convolutional neural network (3D CNN) is used in which atom-type densities are reconstructed using a sequence of 3D convolutional layers and dense layers. Since the output atom densities are fully differentiable with respect to the latent space, a trained variational autoencoder (VAE) 1606 may connect to a bio-activity-prediction module 1604 comprising a trained 3D-CNN model with the same kind of atom densities (as output by the autoencoder) as the features, and then optimize the latent space with respect to the bioactivity predictions against one or more receptors. After that, the optimal point in the latent space can be decoded into a molecule with the desired properties.

Three-dimensional coordinates of potential molecules 1601 are used as inputs to a neural network for 3D reconstruction in latent space 1603 (the 3D models of molecules using volumetric pixels called voxels). Underfitting due to data sparsity may be prevented by optional smoothing 1602 depending on the machine learning algorithm used. Existing molecule examples 1605 are used to train one or more autoencoders 1606 whereby the output of the decoder is used to map atomic features such as atom density in latent space 1607 in the bioactivity model 1604, wherein the bioactivity model consists of a sequence of convolutional and fully connected layers. Backpropagation 1608 (or other gradient-aided search) is performed by searching the latent space for regions that optimize the bioactivities of choice thus arriving at a set of latent examples 1609. Decoding 1610 and ranking 1611 each candidate latent example produces the most viable and best-fit to the initial desired parameters.

As an example, a VAE is trained on an enriched molecule data set until optimal reconstruction is achieved. The decoder of the VAE is used as an input to a bioactivity model, wherein the VAE input is a small molecule and the bioactivity module houses a large molecule, i.e., a protein. The behavior and interactions between the molecules are output from the bioactivity model to inform the latent space of the VAE.

Figure 17:
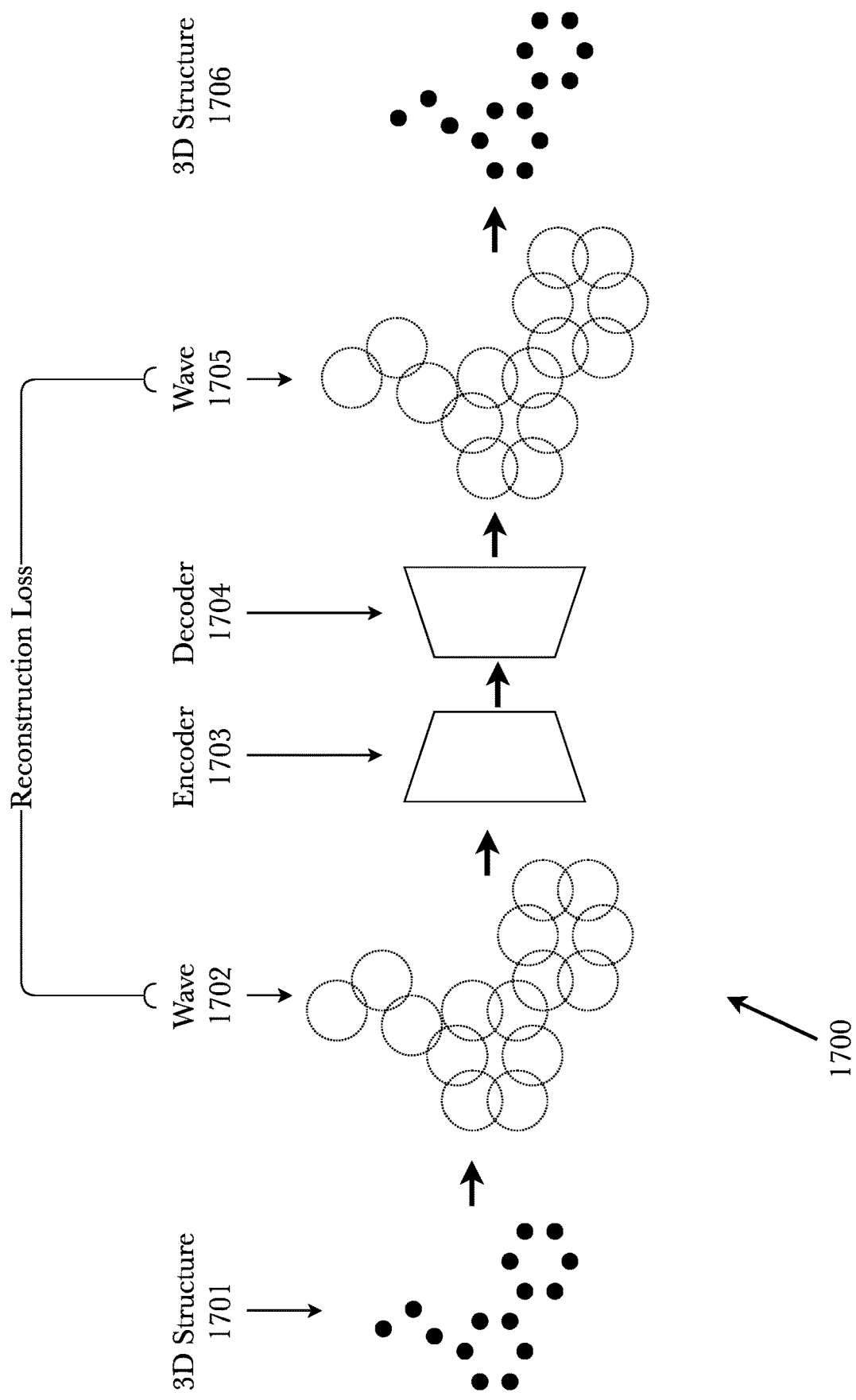
FIG. 17 is a diagram illustrating the training of an autoencoder of a 3D CNN for active example generation.

FIG. 17 is a diagram illustrating the training of an autoencoder 1700 of a 3D CNN for active example generation. In a second preferred embodiment, 3D coordinates of the atomic positions of molecules are reconstructed as smoothed (Gaussian blurring as one method) 3D models 1702, 1705 alleviating the underfitting of encoder 1703 and 3D CNN decoder 1704 models due to high data disparity. Wave representations 1702, 1705 allow voxels to convey the same information as the 3D structures 1701, 1706. One exemplary embodiment uses PyTorch, an open-source machine learning library used for applications such as computer vision and natural language processing, and is used to initially train an autoencoder.

Autoencoders 1700 may also be implemented by other programming languages and forks other than PyTorch. Additional embodiments may comprise a complex pipeline involving Generative Adversarial Networks (GANs) and a hybrid between localized non-maximal suppression (NMS) and negative Gaussian sampling (NGS) may be used to perform the mapping of smoothed atom densities to formats used to reconstruct the molecular graph. Furthermore, training autoencoders 1700 on generating active examples by deconvolution is improved by using a GPU (Graphical Processing Unit) rather than a CPU (Central Processing Unit). Using the embodiments as described above, grants input atom densities to generate detailed deconvolutions by varying noise power spectral density and signal-to-noise ratios.

As a detailed example, the generation may be done in the following steps, using any number of programming languages but is described here using the structure of Python, and by creating various functions (where functions are subsets of code that may be called upon to perform an action). The model is initialized with a trained autoencoder and a dataset of active molecules. The latent representations of the active dataset (or their distributions, in the case a variational autoencoder is used) are computed, by learning the latent space, which may comprise one function. This function may also store the statistics of the active dataset reconstructions, to compare with the statistics of the generated data later. A function which generates a set number of datapoints using the chosen generation method is also employed using a flag method within the class instance may control the generation method (e.g. "perturb", "interp"). Additional parameters for the methods, e.g. the perturbation strength, may be also controlled using instance variables. Another function may be programmed that decodes the generated latent vectors and computes statistics of the generated datasets. These statistics include the validity (percentage of the samples which are valid molecules), novelty (percentage of molecules distinct from the active dataset), and uniqueness (percentage of distinct molecules) of the dataset, as well as the molecular properties, specified in a separate function that computes the properties. Molecular properties may be added or removed to this function at will, without any changes to the rest of the code: summarized statistics and plots are inferred from the molecular properties dictionary. Results may then be summarized in two ways: by printing out the summary of the distributions and generating plots comparing the molecular properties as defined in the computer properties function of the active and generated distributions.

All variables, functions, and preferences are only presented as exemplary and are not to be considered limiting to the invention in any way. Many avenues of training autoencoders or variational autoencoders are known to those in the art by which any number of programming languages, data structures, classes, and functions may be alternatively switched out depending on implementation and desired use.

Figure 18:
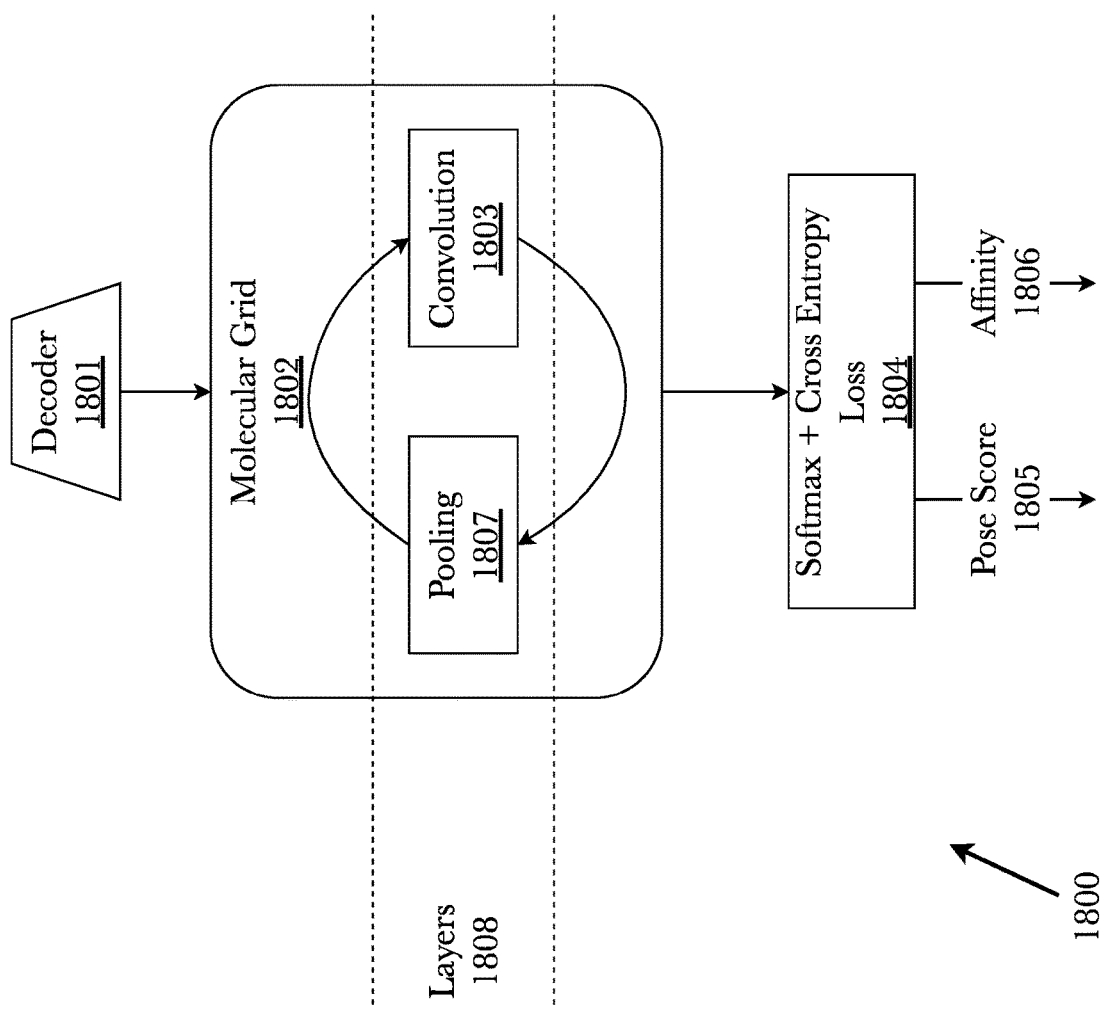
FIG. 18 is a diagram illustrating the interfacing of the decoder to the 3D-CNN bioactivity prediction model.

FIG. 18 is a diagram illustrating the interfacing of the decoder to the 3D-CNN bioactivity prediction model 1800. During training of the neural network machine learning model with inputs of a 3D grid 1802 of Gaussian-like atom type densities, the weights are iteratively modified in order to minimize the losses 1804, which is some measure of the goodness of fit of the model outputs to the training data. In an embodiment, the procedure is performed using some variation of gradient descent, where the changes applied to each weight during the update step are proportional in some way to the gradient of the loss with respect to the weight in question. The calculation of these gradients is often referred to as backpropagation, as the gradients of the loss with respect to a weight (n+1) layers removed from the model output depend, as per the chain rule, only on the gradients of the weights in the layers (0, . . . , n) 1808 away from the model output 1805, 1806, and they are therefore calculated first in the layer closest to the model output and loss, the results of which are used both to update the weights and to calculate the gradients of the loss 1804 with respect to weights further back in the model.

Layers 1808 may perform a function with some parameters and some inputs, as long as the computation performed by a layer 1807/1803 has an analytic derivative of the output with respect to the layer parameters (the faster to compute, the better) These parameters may then be learned with backpropagation. The significance of using voxelated atom-features as inputs to a bioactivity model (as in the case of a 3D CNN) is that the loss can be differentiated not only with respect to the layer weights, but also with respect to the input atom features.

According to one aspect, various cheminformatics libraries may be used as a learned force-field for docking simulations, which perform gradient descent of the ligand atomic coordinates with respect to the binding affinity 1806 and pose score 1805 (the model outputs). This requires the task of optimizing the model loss with respect to the input features, subject to the constraints imposed upon the molecule by physics (i.e., the conventional intramolecular forces caused for example by bond stretches still apply and constrain the molecule to remain the same molecule). Attempting to minimize the loss 1804 directly with respect to the input features without such constraints may end up with atom densities that do not correspond to realistic molecules. To avoid this, one embodiment uses an autoencoder that encodes/decodes from/to the input representation of the bioactivity model, as the compression of chemical structures to a smaller latent space, which produces only valid molecules for any reasonable point in the latent space. Therefore, the optimization is performed with respect to the values of the latent vector, then the optima reached corresponds to real molecules.

Application of this comprises replacing the input of a trained bioactivity model with a decoder 1801 portion of a trained 3D CNN autoencoder, which effectively 'lengthens' the network by however many layers 1808 are contained within this decoder. In the case of a 3D CNN bioactivity model, the 3D CNN autoencoder would thus form the input of the combined trained models. This embodiment allows both differentiable representations which also have an easily decodable many-to-one mapping to real molecules since the latent space encodes the 3D structure of a particular rotation and translation of a particular conformation of a certain molecule, therefore many latent points can decode to the same molecule but with different arrangements in space. The derivative of the loss with respect to the atom density in a voxel allows for backpropagation of the gradients all the way through to the latent space, where optimization may be performed on the model output(s) 1805, 1806 with respect to, not the weights, but the latent vector values.

Following this optimization, the obtained minima can be decoded back into a real molecule by taking the decoder output and transforming the atom-densities into the best-matching molecular structure. During optimization of the latent space, it is likely that some constraints must be applied to the latent space to avoid ending up in areas that decode to nonsensical atom densities.

FIG. 20 is a block diagram of an overall model architecture of a system for de novo drug discovery according to one embodiment. The exemplary model described herein is a variational autoencoder (VAE) 2001-2007 together with a reinforcement learning (RL) component 2008-2010 for a graph-based approach. The aim of said model is to learn a latent distribution that governs molecular properties and provide a decoder 2004, 2009 which can construct chemically valid molecules from samples of the prior. With reinforcement learning 2008-2010 to provide an additional gradient signal, decoded molecules may be checked for chemical validity. Samples from the prior distribution as well as posterior distribution are decoded, and their validity is evaluated. As most cheminformatics toolkits chemical validity checking process is not differentiable, a reward prediction network (a separate MPNN encoder 2011) must be used which is trained to predict the validity of input graph 2001. Together, these components provide an end to end, fully differentiable framework for training.

Figure 21:
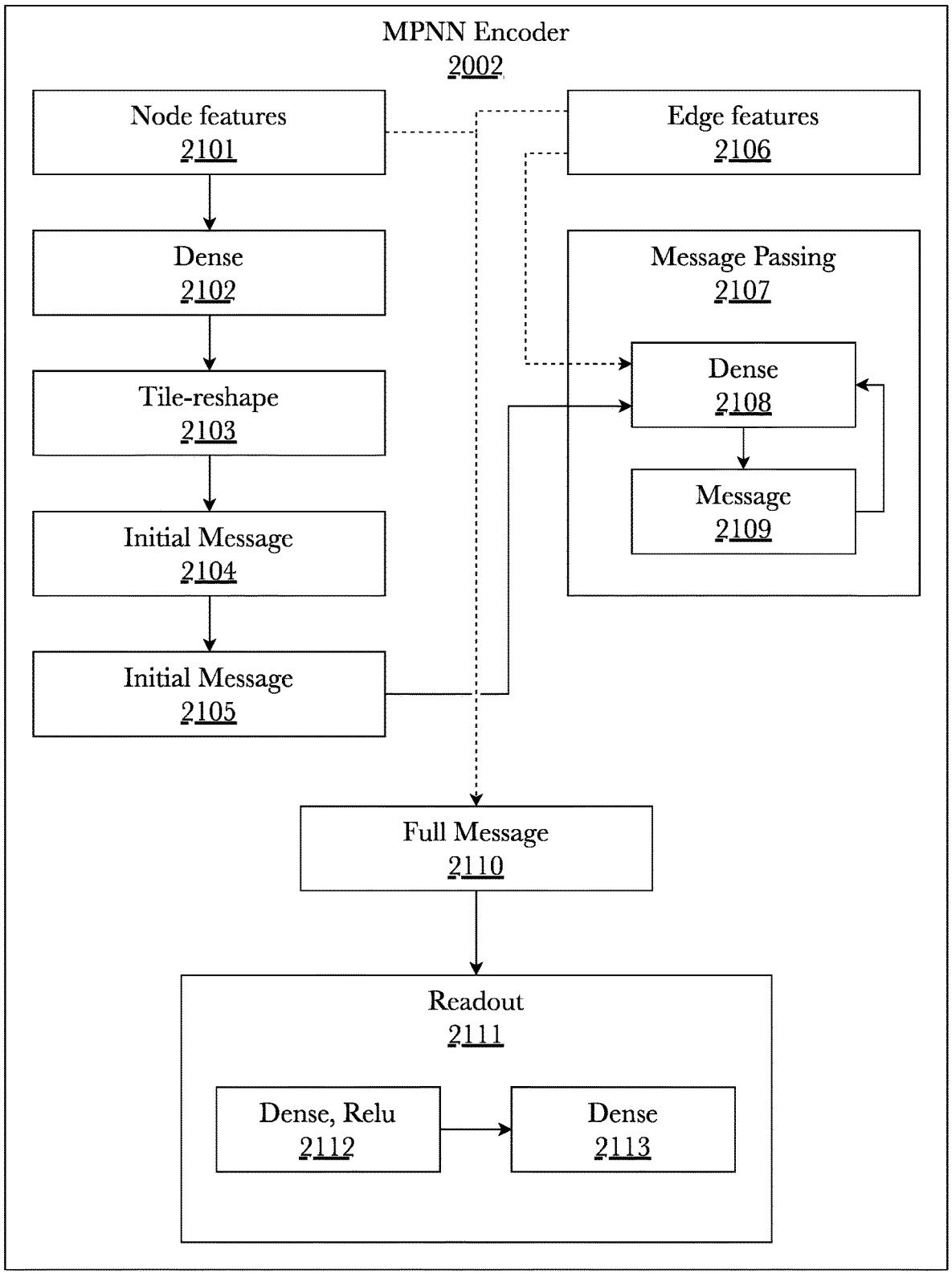
FIG. 21 is a block diagram of a model architecture of a MPNN encoder for de novo drug discovery according to one embodiment.

FIG. 21 is a block diagram of a model architecture of a MPNN encoder 2002 for de novo drug discovery according to one embodiment. MPNN Encoder 2002 consists of given node 2101 and edge features 2106 that are input to dense layers 2102, reshaped 2103, summed 2104, concatenated 2105, and circulated within a message passing neural network 2107-2110, which learns a hidden representation of a molecule (Readout vector 2111). This is done by continuously aggregating neighboring node 2101 and edge 2106 information through a process called message passing 2107. Readout vector is subsequently split in to the mean and variance vectors 2112, 2113 which serve and as the parameters of the posterior distribution from which the latent samples 2302 are sampled.

Figure 22:
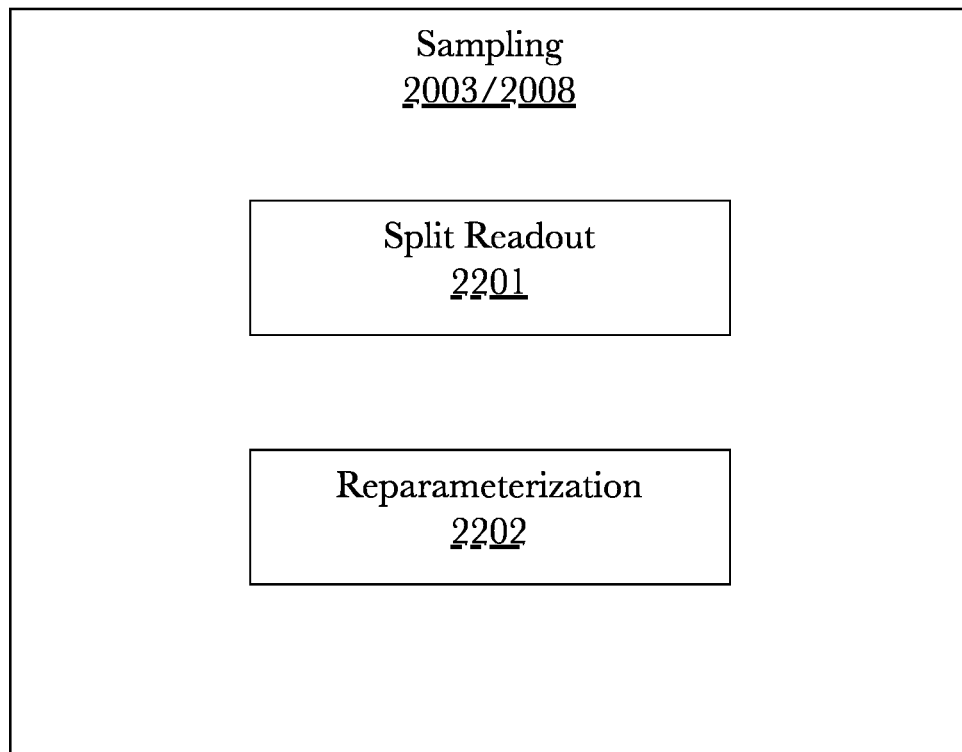
FIG. 22 is a block diagram of a model architecture of a Sampling module for de novo drug discovery according to one embodiment.

FIG. 22 is a block diagram of a model architecture of a Sampling module 2003/2008 for de novo drug discovery according to one embodiment. The sampling module comprises a split readout function 2201 that produces the mean and log(sigma$^2$) of the batch. A reparameterization function 2202 is used to get a differentiable sampling procedure and a sample of N (mean, std) using a known property of the Gaussian distribution. N (mean, std) is equal to N (0, 1) times sigma plus the mean.

Figure 23:
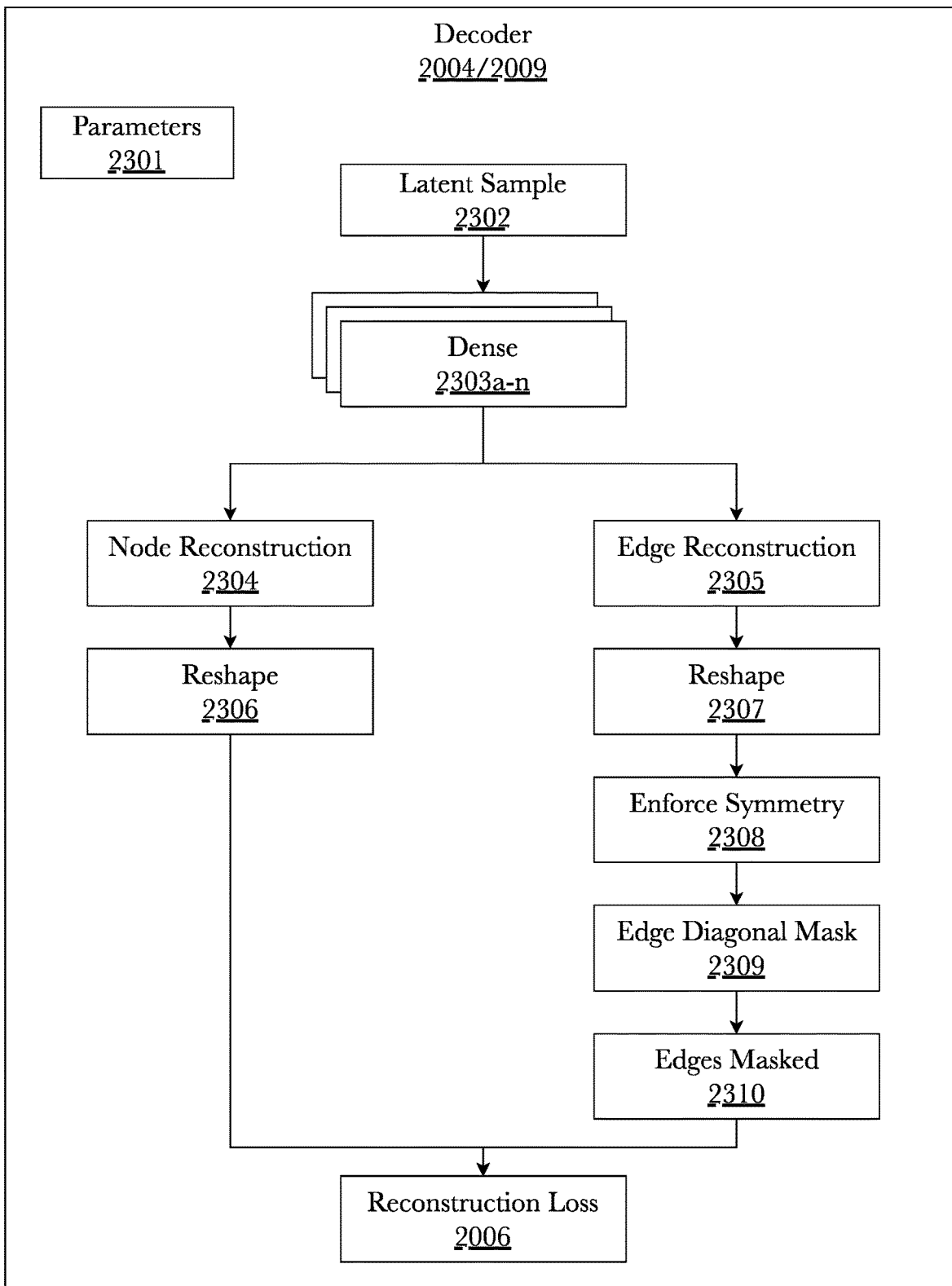
FIG. 23 is a block diagram of a model architecture of a decoder for de novo drug discovery according to one embodiment.

FIG. 23 is a block diagram of a model architecture of a decoder 2004/2009 for de novo drug discovery according to one embodiment. A decoder 2004/2009 with parameters 2301 for the maximum number of atoms to generate along with node and edge size is used to formulate the reconstruction loss 2006. Latent samples 2302 are passed through a sequence of dense layers 2303a-n and subsequently processed via two different matrices to reconstruct node feature 2304 and edge feature 2305 matrices. Shape functions 2306, 2307 ensure the shapes of (No Atoms, No Node Features) and (No Atoms, No Atoms, No Edge Features) respectively. Currently this is enforced by using a maximum number of allowed atoms to reconstruct. Further, an additional entry for each of the encoded feature distributions is performed, which represents the possibility of No Atom/No Feature 2308-2310. Finally, the node and edge feature matrices are compared using an approximate graph matching procedure 2006 which looks at atom types, bond types, atom-bond-atom types.

Figure 24:
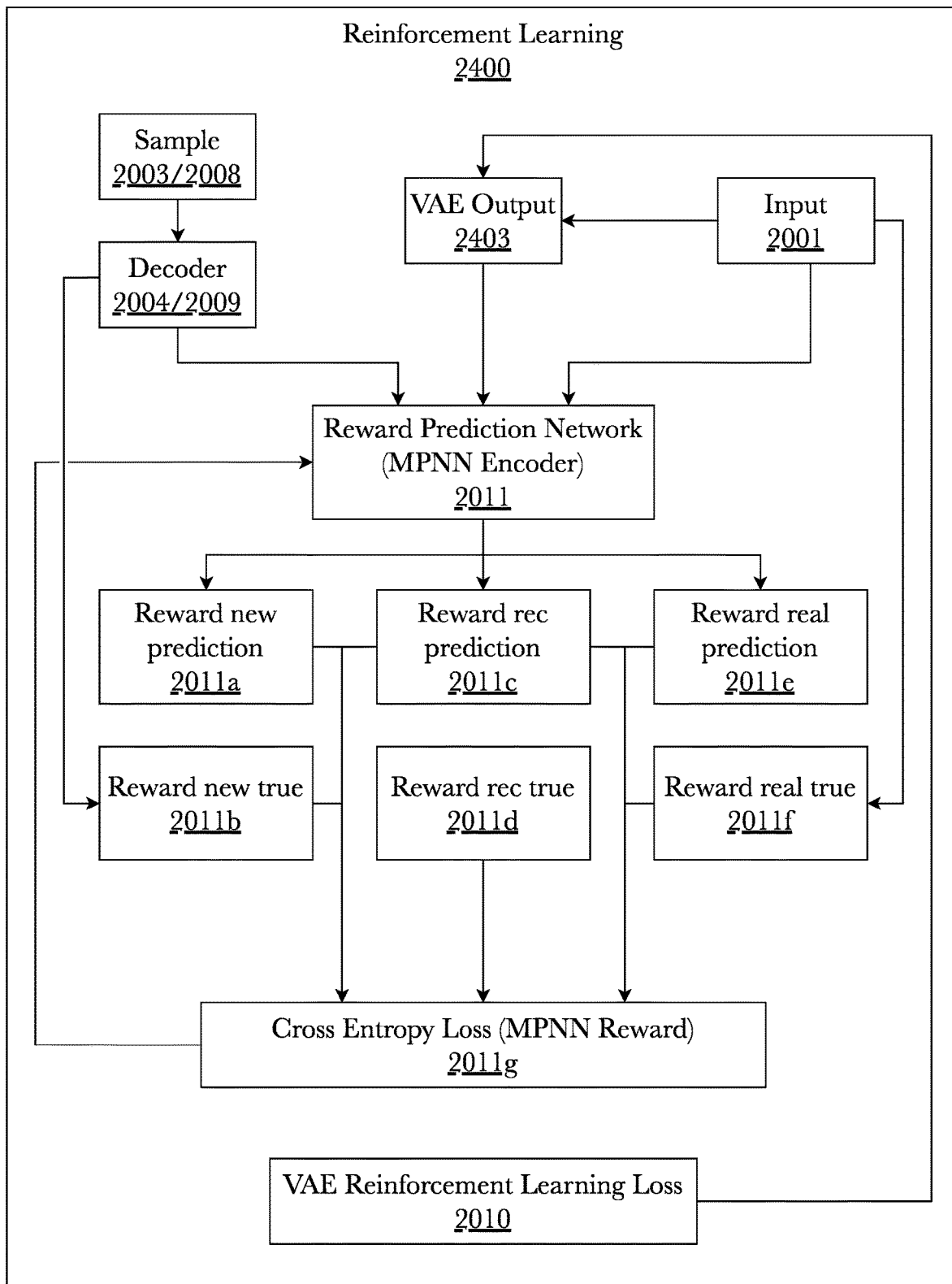
FIG. 24 is a block diagram of a model architecture for reinforcement learning for de novo drug discovery according to one embodiment.

FIG. 24 is a block diagram of a model architecture for reinforcement learning 2400 for de novo drug discovery according to one embodiment. The reinforcement learning 2400 as also shown in FIG. 20, comprises samples 2003/2008 and nodes and edges that inform a reward prediction network 2011. The reward prediction network 2011 receives a batch of latent examples from the decoders 2004/2009, nodes and edges from the VAE output 2403 and the input 2001, where the output of the VAE 2403 is made up of reconstructions of received nodes and edges from the input 2001. The MPNN encoder 2011 is trained to predict rewards 2011a-f given the nodes and edges. Cross entropy loss 2011g is the sum of each of the individual reward combinations 2011a-f and is backpropagated through the reward prediction network 2011, while the VAE RL loss 2010 is fed back into the VAE output 2403.

Figure 25:
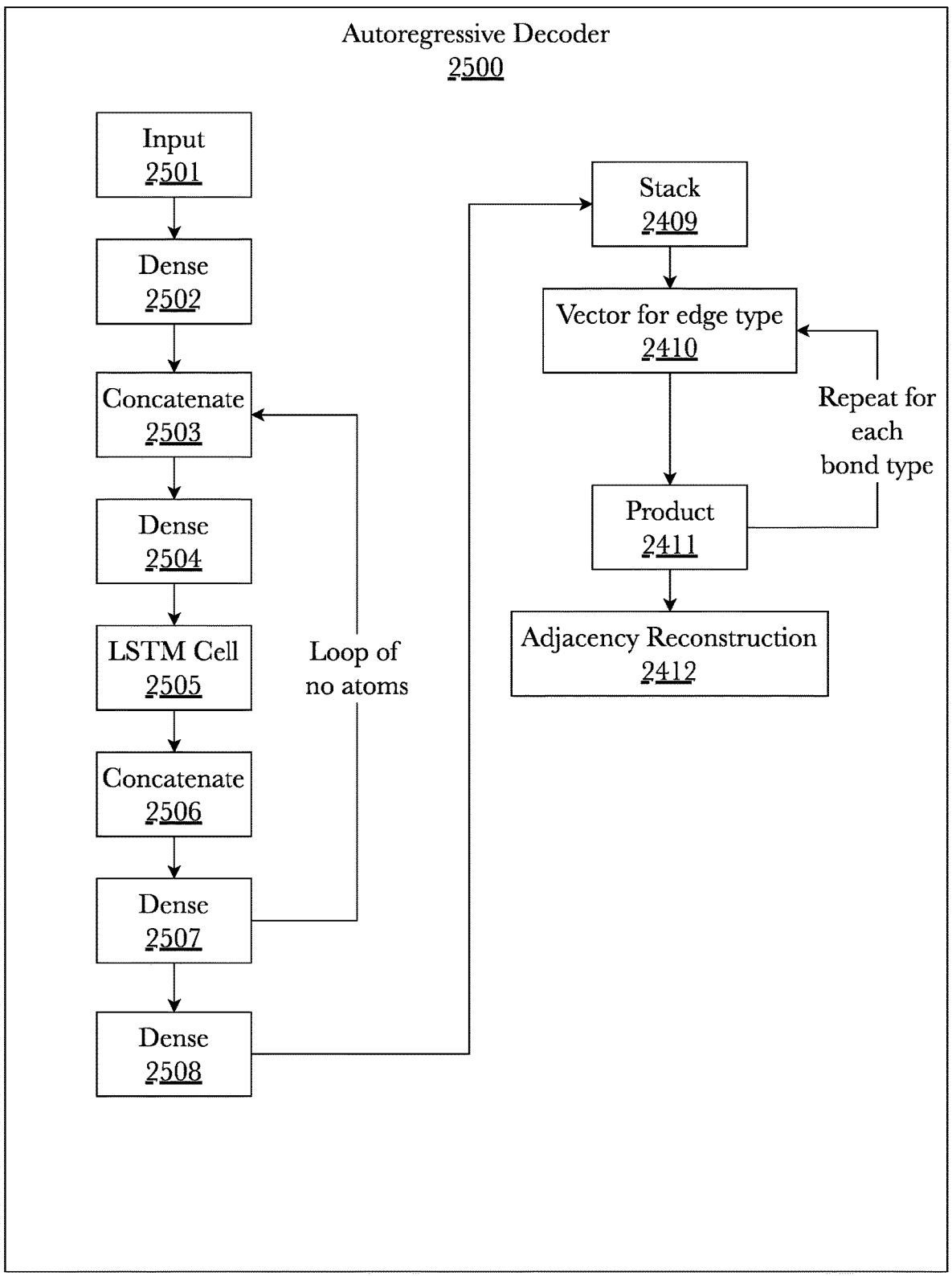
FIG. 25 is a block diagram of a model architecture of an autoregressive decoder for de novo drug discovery according to one embodiment.

FIG. 25 is a block diagram of a model architecture of an autoregressive decoder 2500 for de novo drug discovery according to one embodiment. Latent vectors of size dimension z are inputs 2501 to the autoregression decoder 2500 and subsequently calculated into dense layers 2502 where their dimensions may be expanded. A concatenation function 2503 precedes a second dense layer 2504 where pre-LSTM feature extraction occurs. After the LSTM cell function 2505, which corresponds to the LSTM recurrence operation, another concatenation occurs 2506 before a third dense layer 2507 extracts nonlinear features. The loop between the third dense layer 2507 and the first concatenation has no atoms. The fourth dense layer 2508 processes atom node features for the stack 2409 to begin node reconstruction. For each bond type a vector for the edge type is created 2410 where the product 2411 outputs probable bond types between nodes. Lastly, adjacency reconstruction 2412 is modeled by a set of edge-specific factors, (e.g., logistic sigmoid function, the corresponding diagonal vector matrix) which are learned parameters.

Figure 26:
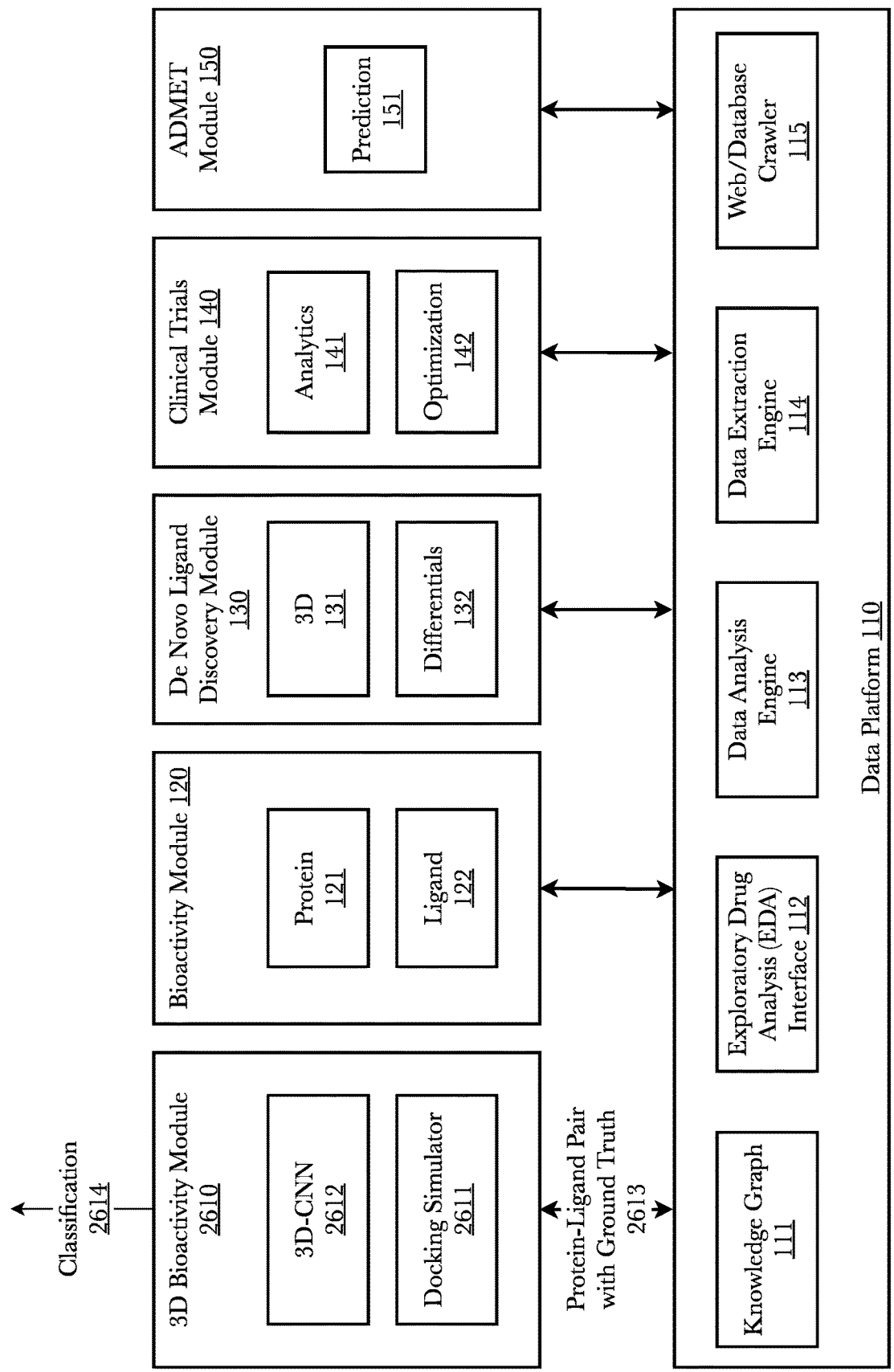
FIG. 26 is a block diagram of an exemplary system architecture for a 3D Bioactivity platform.

FIG. 26 is a block diagram of an exemplary system architecture for a 3D Bioactivity platform. According to one embodiment, a 3D bioactivity module 2610, comprising a docking simulator 2611 and a 3D-CNN 2612 may be incorporated into the system described in FIG. 1 containing elements 110-151. A data platform 110 scrapes empirical lab results in the form of protein-ligand pairs with a ground-truth state 2613 from public databases that is then used in a docking simulator 2611 to produce a data set for which to train a three-dimensional convolutional neural network (3D-CNN 2612) classifier, which as disclosed herein is a model that can classify a given input of a certain protein-ligand pair is active or inactive and whether or not the pose is correct 2614. A key feature of the 3D-CNN bioactivity module 2610 as disclosed herein, is the ability to produce visualizations of the interactions in the input that are vital to the active/inactive classifications in a more interpretable manner than a FASTA-based model currently used in the art. The output incorporates gradients relating to the binding affinity of specific atoms that a user may use to understand where the model was most attentive and would further provide an explanation why specific molecules are bioactive and why certain molecules are not and to identify the important residues of the binding site. Once the residues are identified, sequence-based similarities algorithms may identify similar motifs in other proteins from the same family or in completely novel proteins relating to that ligand interaction. Furthermore, the 3D-CNN model disclosed herein improves upon current art by penalizing the model for incorrect docking, thus leading to a three class classification 2614: active, inactive, and incorrect docking.

Figure 28:
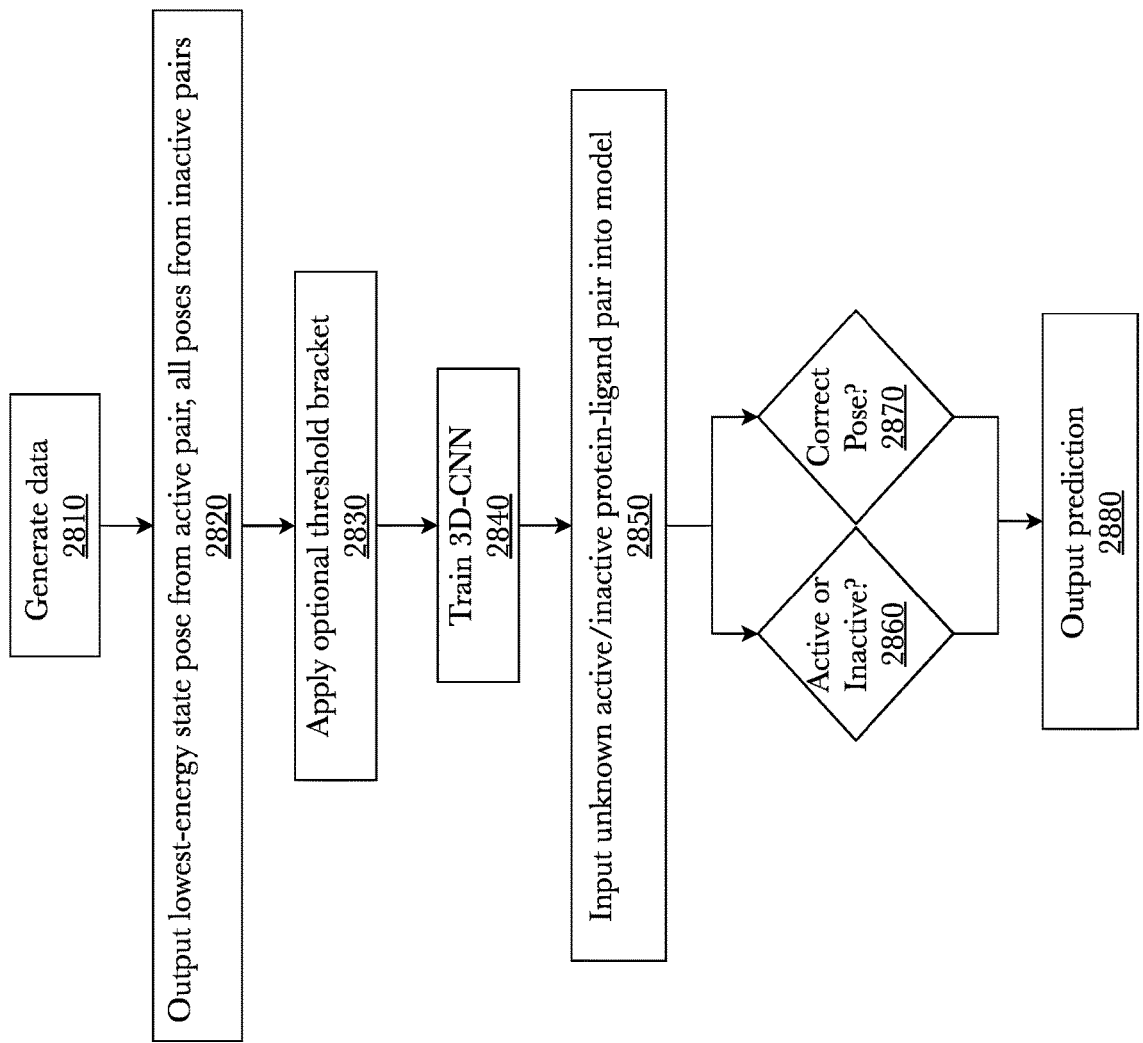
FIG. 28 is a flow diagram illustrating an exemplary method for classifying protein-ligand pairs using a 3D Bioactivity platform.

FIG. 28 is a flow diagram illustrating an exemplary method for classifying protein-ligand pairs using a 3D Bioactivity platform. Data is generated 2810 from lab-based empirical evidence which constitutes protein-ligand pairs and their ground-truth state. That data is sent to a docking simulation whereby energy states of the input poses are output along with a classification of active/inactive—from the lab data 2820. The training data presents a choice of a threshold bracket 2830. The threshold bracket is a trade-off between the average information contained in each datapoint, and the sheer quantity of data, assuming that datapoints with more extreme inactive/active $IC_{50}$ values are indeed more typical of the kind of interactions that determine whether or not a protein-ligand pair is active or inactive. In the case of the 3D-model, using the dataset with no threshold performs consistently better across most metrics. The channels used for the data set are hydrophobic, hydrogen-bond donor or acceptor, aromatic, positive or negative ionizable, metallic and total excluded volume. Regardless of the choice of threshold, the data is then used to train a 3D-CNN to know the classification of a molecule regarding activation and pose propriety 2840. The 3D bioactivity platform then receives an unknown molecule 2850 that is fed into the model to determine its classifications 2860/2870. The prediction is output 2880, and in some embodiments, may be used in backpropagation to further inform the model.

Figure 30:
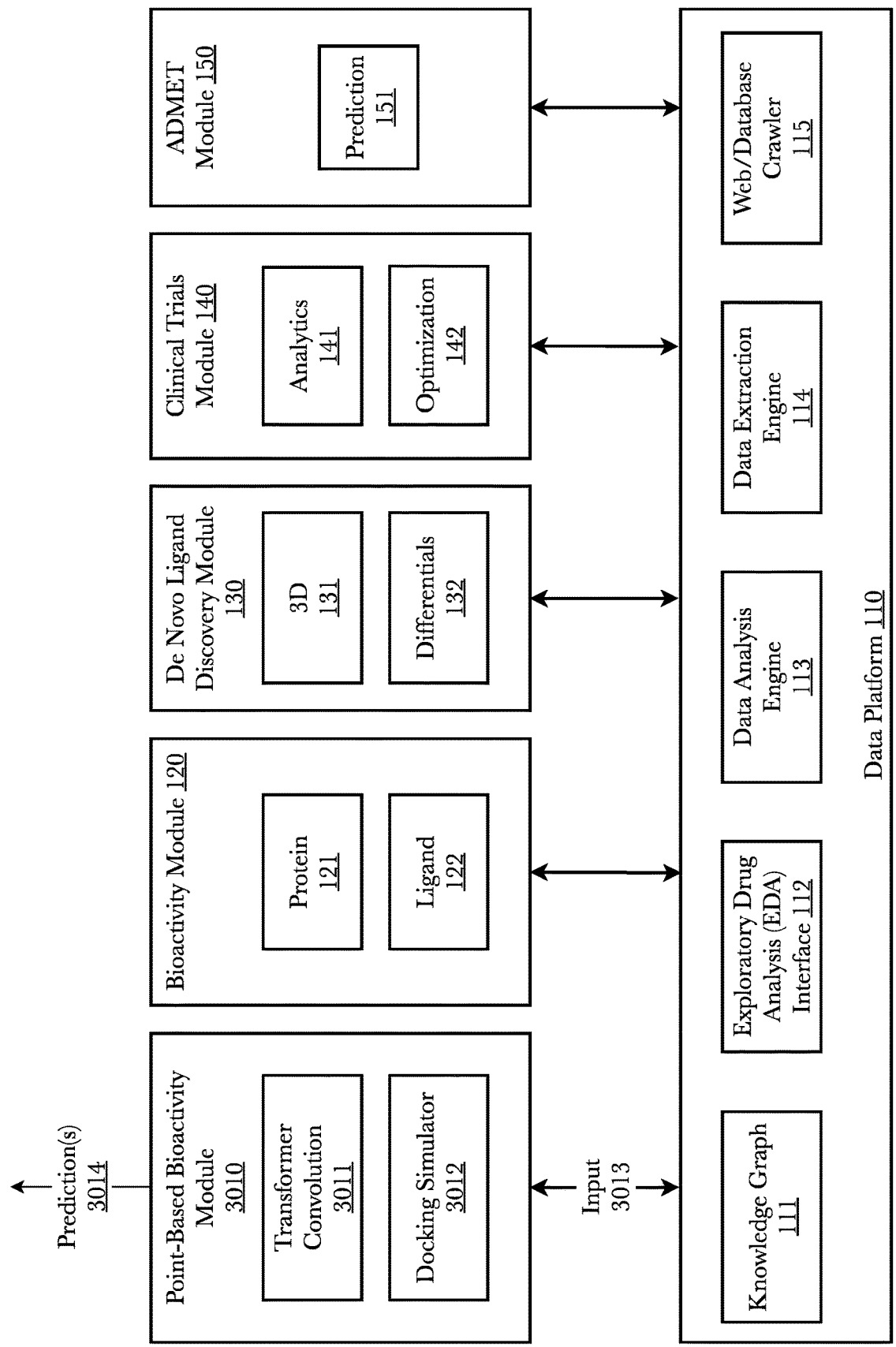
FIG. 30 is a block diagram of an exemplary system architecture for a Point-Cloud Bioactivity platform.

FIG. 30 is a block diagram of an exemplary system architecture for a Point-Cloud Bioactivity platform. Instead of representing protein-ligand complexes as voxel grids containing atom densities as in other embodiments disclosed herein, this embodiment represents protein-ligand complexes as atoms with associated coordinates, i.e., point-cloud models. Point cloud models allow for pointwise operations on these coordinates (and in some cases operations that capture spatial relationships between points), and, depending on the task, agglomerate these into either a single representation that can be used for a classification or regression task, or to perform a pointwise regression or classification task on the set of points. An exemplary pseudocode implementation 3400 is presented in FIG. 34.

According to one embodiment, a point-cloud bioactivity module 3010, comprising a docking simulator 3012 and one or more transformer convolution algorithms 3010 may be incorporated into the system described in FIG. 1 or in FIG. 26, both containing elements 110-151. The point-based bioactivity module 3010 comprises two main operating states with two more substates in each main operating state. The first main operating state is a training state from which a model for the second main operating state is produced. The second main operating state is a platform for which users may query one or more protein-ligand pairs and receive a bioactivity prediction, the prediction generated from the trained model achieved from the first main operating state. For both main operating states, there are two modes of operation: Coupled and decoupled. Whether training or querying, the point-based bioactivity module 3010 may use the docking simulator 3012 or not. In a specific coupled case, the docking simulator 3012 may be used initially but if the results are incongruent, the simulation failed, or the results are otherwise undesirable, the point-based bioactivity module 3010 will default to a decoupled operating state. The input 3013 to the point-based bioactivity module 3010, whether training or querying, are molecular structure files. These molecular structure files are either in the form of empirical lab results retrieved and scraped via the data platform 110 for the training mode of operation, or submitted by a user for the querying mode of operation. The user may submit a protein file, or a protein file with an alternative ligand file, or coordinates of the binding pocket, or other alternative protein-ligand file configurations. The option to use a decoupled or coupled state—whether the protein-ligand pose propriety is known or predicted—may be decided depending on the task at hand. Given specific time or computing constraints, the user may manually, or the point-based bioactivity module 3010 may automatically choose a decoupled operating state, bypassing the docking simulator to save time or computing resources.

During the training operating state, predictions 3014 from the transformer convolution module(s) 3011 comprise whether the protein-ligand pair generated matches closely enough the crystal structure of the ground-truth pair, and the bioactivity. Typically, but not limited to, a threshold of 2 angstroms is used to determine the crystalline structure similarity. The crystal structure similarity may also be used to decide whether to penalize the model for predicting too high a bioactivity if the crystal-structure comparison does not meet the 2-angstrom threshold.

During the querying operating mode, a bioactivity prediction is output, combined from the regression output and the classification of active/inactive-ness. Further, a 3D dimensional model of importances is generated as well. The output predictions 3014, described above are merely exemplary, and it is to be understood that in either training or querying mode, all five outputs (active, inactive, crystal-like, not crystal-like, and regression) or any combination thereof may be used.

Further, according to various embodiments, model ensembling, or the use and combination of various machine learning models is anticipated. This means, in addition to the transformer convolution system and method described in this embodiment, other machine learning models may be integrated within, replaced by other models, and otherwise combined in such a way to enhance the prediction of bioactivity.

Figure 31:
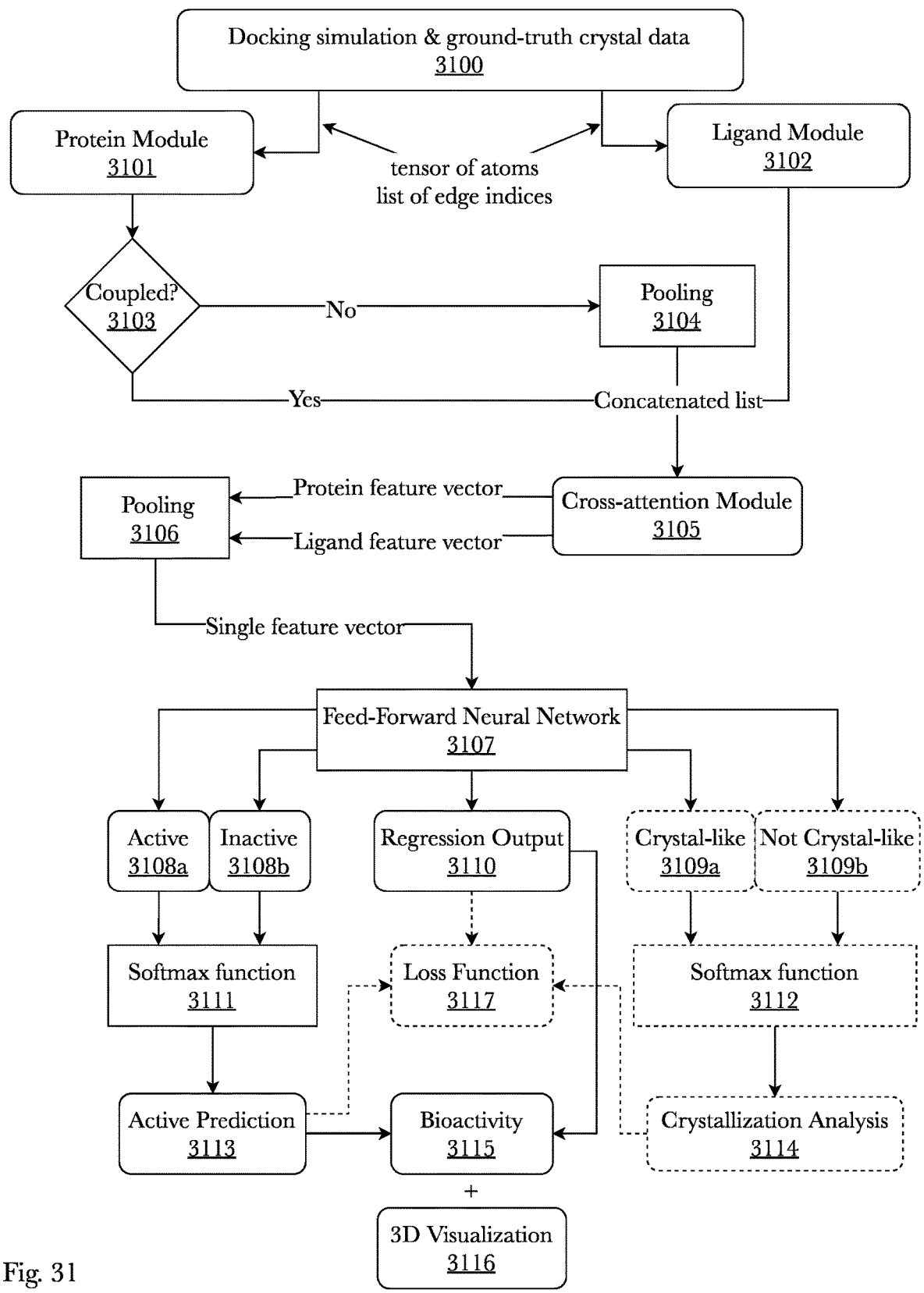
FIG. 31 is a block diagram of an exemplary model architecture for a Point-Cloud Bioactivity platform.

FIG. 31 is a block diagram of an exemplary model architecture for a Point-Cloud Bioactivity platform. The output of the model comprises one or more predictions (e.g., active or inactive, crystal structure similarity, regression output, and bioactivity). The outputs are task dependent, wherein the output may contain one or more of the classifications, regressions, a bioactivity value, or some combination thereof. The values of regression or bioactivity may take any form desirable to the user; however, a few exemplary values comprise units of $-\log_{10}(IC_{50})$, or $-\log_{10}(Ki)$, or the negative log base ten of any other bioactivity metric, which again is merely exemplary.

As described in FIG. 30, molecular structure files are used as the inputs 3100, and come from a variety of sources. As one example, a user may upload a structural file of a protein which comprises an ID from which the bioactivity platform downloads a corresponding molecular structure file. Then the user informs the system where in the pocket the ligand lies, or may upload a file of the ligand in the binding pocket, or just supply the molecular structure of a ligand. These inputs are fed as into two independent modules 3101/3102, one for the protein 3101 and a separate one for the ligand 3102. Because a point-cloud model is a graph with no edges, edges for the protein model, i.e., the protein module 3101, are generated by determining the proximity of all the atoms within a certain distance to the ligand or binding pocket. The ligand submodule 3102 creates edges for the ligand model from the information contained in the molecular structure file comprising bonds, e.g., single bonds, double bonds, aromatic bonds, etc. For decoupled protein-ligand pairs, i.e., protein-ligand pairs where docking simulations failed or are ligand-binding pocket conformations otherwise not available 3103, pooling (Max, weighted, etc.) 3104 is performed on the protein, creating a collapsed vector of protein atoms. For example, only protein atoms from the binding site are kept for decoupled pairs, while protein atoms within 4 angstroms of the ligand are kept for a coupled model.

The output of the protein and ligand modules 3105 also includes the combined protein-ligand complex of coupled molecules via docking simulations. In other words, the input to the cross attention module 3105 is a concatenated atom list of the protein and ligand, wherein the edge list contains only edges where one atom is a protein, and one atom is a ligand atom. Furthermore, the cross attention module 3105 restricts attention between protein and ligand atoms in close proximity, ergo, the model can only learn from the actual interactions, whereas without this restriction, there is no coupling between protein and ligand. The vector output of the cross-attention model 3105 is pooled 3106 into a single feature vector that feeds into a feed-forward neural network 3107.

One set of outputs is a crystal-structure similarity analysis 3114, which is comprised from two output nodes 3109a-b that are sent through a SoftMax function 3112, and predict whether the protein-ligand pair in question is similar enough to the ground truth crystal structure (typically within a 2 angstroms threshold) 3111. Typically, the crystallization analysis 3114 is only used for training, however output during a user query is anticipated. Another output comprises a SoftMax function 3111 containing two output nodes of the active/inactive prediction 3108a-b of the protein-ligand pair in question and producing a prediction 3113 of that active/inactive status. The regression output 3110 and active-ness prediction 3113 inform the bioactivity prediction value 3115. A user query may return in addition to a bioactivity prediction 3115, a 3D visualization 3116 of the queried protein-ligand pair with various information about the importances as laid out in FIG. 33.

During training of the model, a loss function 3117 is used and is configured to penalize the model if the model predicts too high a bioactivity for a non-crystal-like structured protein-ligand pair, but is not penalized for predicting too low a bioactivity, while also simultaneously trained on the classification task. At prediction time, the model may use the crystal structure probability to decide whether to take bioactivity reading or discard it as inaccurate. From there more docking poses may be generated until a likely crystal structure is found.

Detailed Description of Exemplary Aspects

Figure 10:
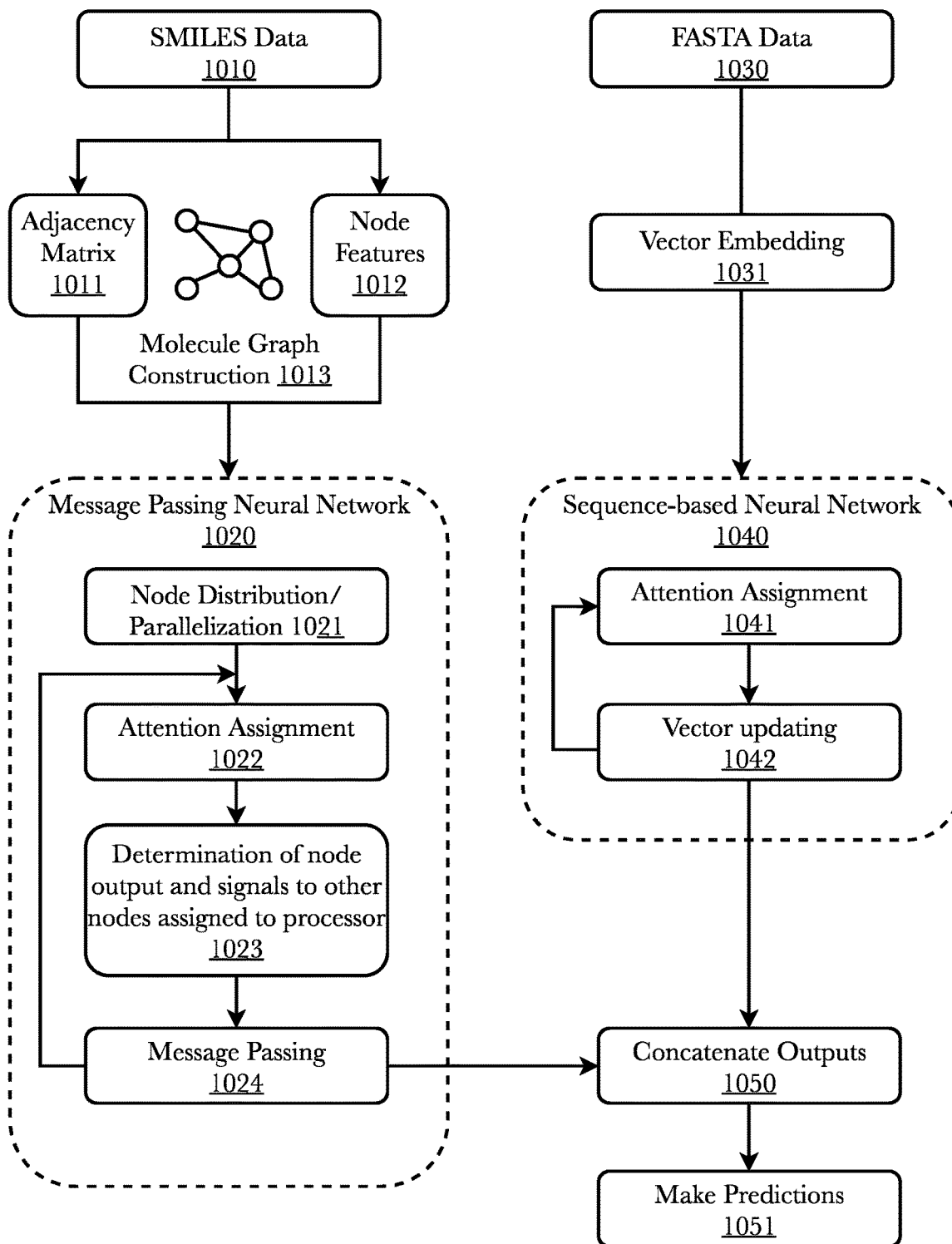
FIG. 10 is a diagram illustrating an exemplary architecture for prediction of molecule bioactivity using concatenation of outputs from a graph-based neural network which analyzes molecule structure and a sequence-based neural network which analyzes protein structure.

FIG. 10 is a diagram illustrating an exemplary architecture for prediction of molecule bioactivity using concatenation of outputs from a graph-based neural network which analyzes molecules and their known or suspected bioactivities with proteins and a sequence-based neural network which analyzes protein segments and their known or suspected bioactivities with molecules. In this architecture, in a first neural network processing stream, SMILES data 1010 for a plurality of molecules is transformed at a molecule graph construction stage 1013 into a graph-based representation wherein each molecule is represented as a graph comprising nodes and edges, wherein each node represents an atom and each edge represents a connection between atoms of the molecule. Each node represents the atom as node features comprising an atom type and a number of bonds available for that atom. The node features are represented as a node features matrix 1012. The molecule, then, is represented as nodes (atoms) connected by edges (bonds), and is specified as an adjacency matrix 1011 showing which nodes (atoms) are connected to which other nodes (atoms).

At the training stage, the adjacency matrices 1011 and node features matrices 1012 for many molecules are input into the MPNN 1020 along with vector representations of known or suspected bioactivity interactions of each molecule with certain proteins. Based on the training data, the MPNN 1020 learns the characteristics of molecules and proteins that allow interactions and what the bioactivity associated with those interactions is. At the analysis stage, a target molecule is input into the MPNN 1020, and the output of the MPNN 1020 is a vector representation of that molecule's likely interactions with proteins and the likely bioactivity of those interactions.

Once the molecule graph construction 1013 is completed, the node features matrices 1012 and adjacency matrices 1011 are passed to a message passing neural network (MPNN) 1020, wherein the processing is parallelized by distributing groups 1021 nodes of the graph amongst a plurality of processors (or threads) for processing. Each processor (or thread) performs attention assignment 1022 on each node, increasing or decreasing the strength of its relationships with other nodes, and outputs of the node and signals to other neighboring nodes 1023 (i.e., nodes connected by edges) based on those attention assignments are determined. Messages are passed 1024 between neighboring nodes based on the outputs and signals, and each node is updated with the information passed to it. Messages can be passed between processors and/or threads as necessary to update all nodes. In some embodiments, this message passing (also called aggregation) process is accomplished by performing matrix multiplication of the array of node states by the adjacency matrix to sum the value of all neighbors or divide each column in the matrix by the sum of that column to get the mean of neighboring node states. This process may be repeated an arbitrary number of times. Once processing by the MPNN is complete, its results are sent for concatenation 1050 with the results from a second neural network, in this case a long short term memory neural network 1040 which analyzes protein structure.

In a second processing stream, FASTA data 1030 is converted to high-dimensional vectors 1031 representing the amino acid structure of proteins. The vectors are processed by a long short term memory (LSTM) neural network 1040 which performs one or more iterations of attention assignment 1041 and vector updating 1042. The attention assignment 1041 of the LSTM 1040 operates in the same way as that of the MPNN 1020, although the coding implementation will be different. At the vector updating stage 1042, the vectors comprising each cell of the LSTM 1040 are updated based on the attention assignment 1041. This process may be repeated an arbitrary number of times. Once processing by the LSTM 1040 is complete, its results are sent for concatenation 1050 with the results from the first processing stream, in this case the MPNN 1020.

Concatenation of the outputs 1050 from two different types of neural networks (here an MPNN 1020 and an LSTM 1040) determines which molecule structures and protein structures are compatible, allowing for prediction of bioactivity 1051 based on known or suspected similarities with other molecules and proteins.

Figure 11A:
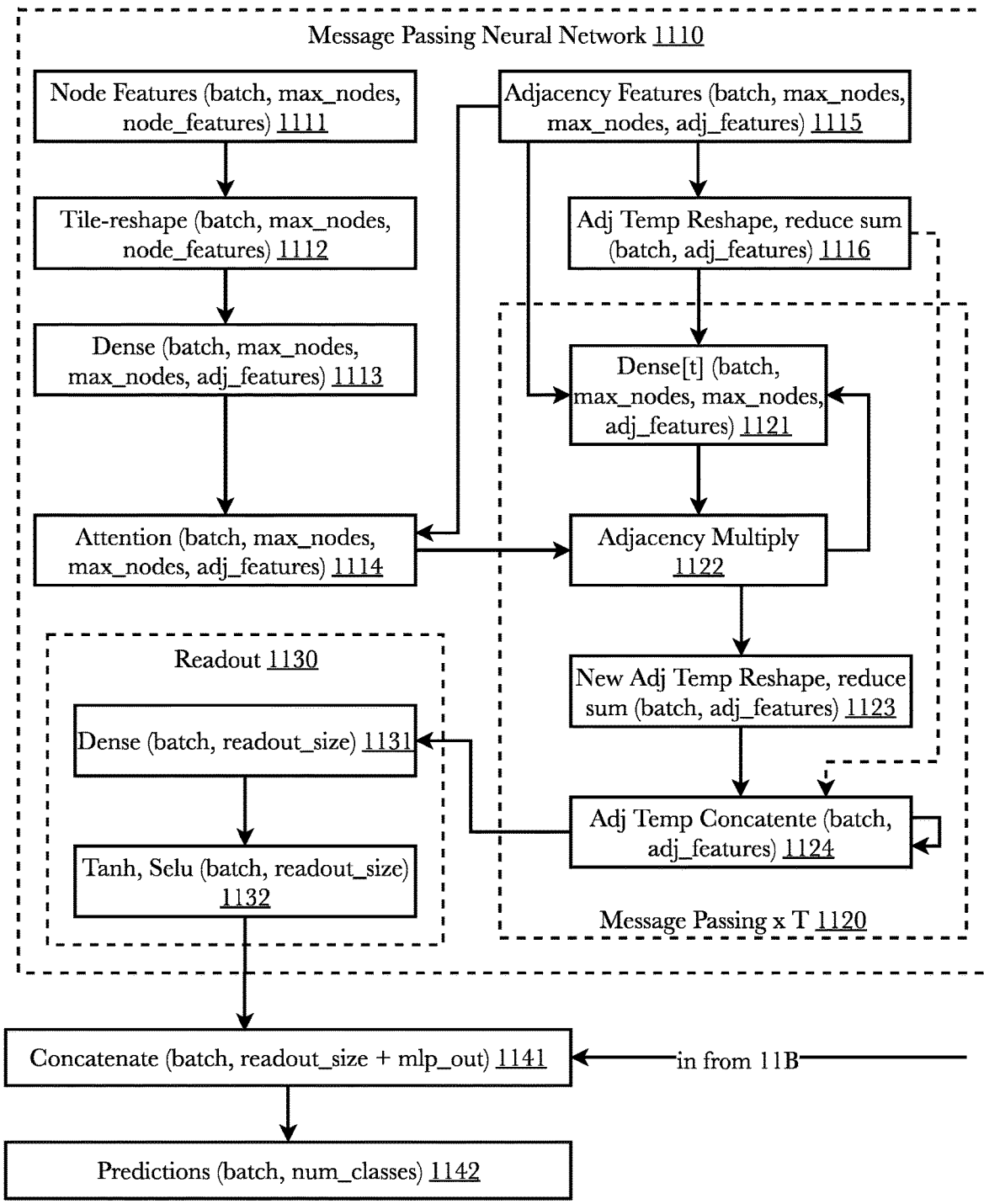
FIGS. 11A and 11B illustrates an exemplary implementation of an architecture for prediction of molecule bioactivity using concatenation of outputs from a graph-based neural network which analyzes molecule structure and a sequence-based neural network which analyzes protein structure.
Figure 11B:
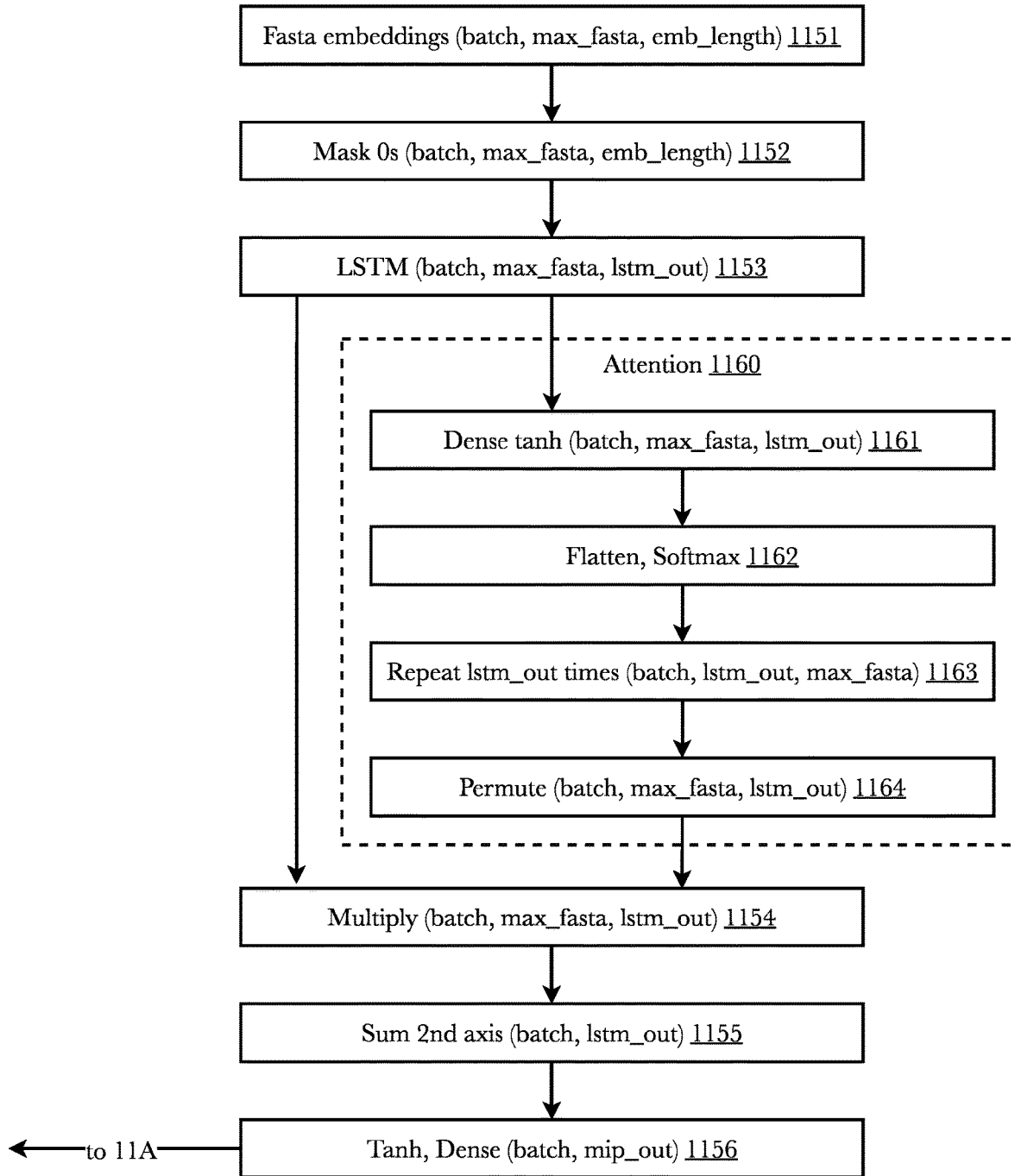

FIGS. 11A and 11B illustrate an exemplary implementation of the architecture for prediction of molecule bioactivity using concatenation of outputs from a graph-based neural network which analyzes molecule structure and a sequence-based neural network which analyzes protein structure. In this example, details regarding a particular implementation of the general architecture shown in FIG. 10 are described.

As shown in FIG. 11A, node features 1111 are received for processing. A reshaping process 1112 may be performed which to conform the dimensionality of the inputs to the dimensionality required for processing by the MPNN. A dense function 1113 is performed to map each node in the previous layer of the neural network to every node in the next layer. Attention is then assigned 1114 using the adjacency matrix contained in the node. The adjacency features (the adjacency matrix) 1115 are simultaneously reshaped 1116 to conform the dimensionality of the inputs to the dimensionality required for processing by the MPNN.

At this stage, a message passing operation 1120 is performed, comprising the steps of performing a dense function 1121 (used only on the first message pass) to map each node in the previous layer of the neural network to every node in the next layer, matrix multiplication of the adjacencies 1122, reshaping of the new adjacencies 1123, and where the message passing operation has been parallelized among multiple processors or threads, concatenating the outputs of the various processors or threads 1124.

Subsequently, a readout operation 1130 is performed comprising performance of a dense function 1131 and implementation of an activation function 1132 such as tan h, selu, etc. to normalize the outputs to a certain range. In this embodiment, the readout operation 1130 is performed only at the first message pass of the MPNN 1110.

As shown in FIG. 11B, FASTA data is converted to high-dimensional vectors 1151, which may then be masked 1152 to conform the vectors to the fixed input length required by the LSTM 1153. The LSTM 1153 then processes the vectors using an attention mechanism 1160 comprising the steps of performing a dense function 1161 to map each node in the previous layer of the neural network to every node in the next layer, performing a softmax function 1162 to assign probabilities to each node just before the output layer. The process is repeated a number of times which may be configured by a parameter 1163. Where permutation invariance is an issue (i.e., where changes in the order of inputs yield changes in the outputs), permutations may be applied to the inputs 1164 to ensure that differences in outputs due to differences in inputs are incorporated.

After attention has been assigned 1160, the vectors in the cells of the LSTM 1153 are multiplied 1154, summed 1155, and a dense function 1156 is again applied to map each node in the previous layer of the neural network to every node in the next layer, and the outputs of the LSTM 1153 are sent for concatenation 1141 with the outputs of the MPNN 1110, after which predictions can be made 1142.

Figure 12:
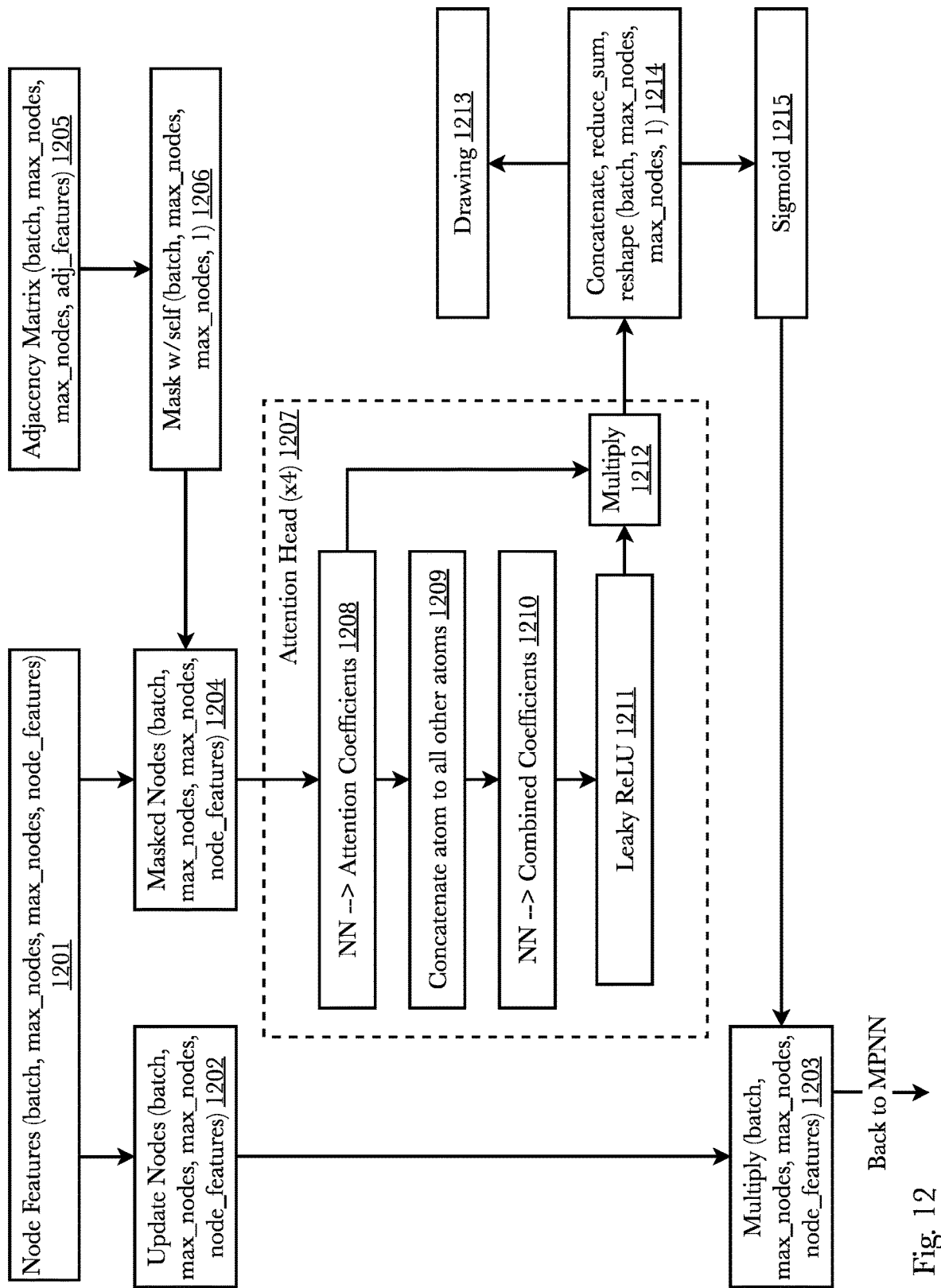
FIG. 12 illustrates an exemplary implementation of the molecule attention assignment aspect of an architecture for prediction of molecule bioactivity using concatenation of outputs from a graph-based neural network which analyzes molecule structure and a sequence-based neural network which analyzes protein structure.

FIG. 12 illustrates an exemplary implementation of an attention assignment aspect of an architecture for prediction of molecule bioactivity using concatenation of outputs from a graph-based neural network which analyzes molecule structure and a sequence-based neural network which analyzes protein structure. This is an exemplary implementation of attention and may not be representative of a preferred embodiment. In this example, details regarding a particular implementation of the attention assignment blocks shown in FIG. 10 are described. The particular implementation of this example involves a multi-head attention mechanism.

As node features 1201 are received for processing, they are updated 1202 and sent for later multiplication 1203 with the outputs of the multiple attention heads 1207. Simultaneously, the nodes are masked 1204 to conform their lengths to a fixed input length required by the attention heads 1207. The adjacency matrix 1205 associated with (or contained in) in each node is also masked 1206 to conform it to a fixed length and sent along with the node features to the multi-head attention mechanism 1207.

The multi-head attention mechanism 1207 comprises the steps of assigning attention coefficients 1208, concatenating all atoms to all other atoms 1209 (as represented in the adjacency matrix), combining the coefficients 1210, performing a Leaky ReLU 1211 function to assign probabilities to each node just before the output layer, and performing matrix multiplication 1212 on the resulting matrices.

The outputs of the multi-head attention mechanism 1207 are then concatenated 1214, and optionally sent to a drawing program for display of the outputs in graphical form 1213. A sigmoid function 1215 is performed on the concatenated outputs 1214 to normalize the outputs to a certain range. The updated node features 1202 are then multiplied 1203 with the outputs of the multi-head attention mechanism 1207, and sent back to the MPNN.

Figure 13:
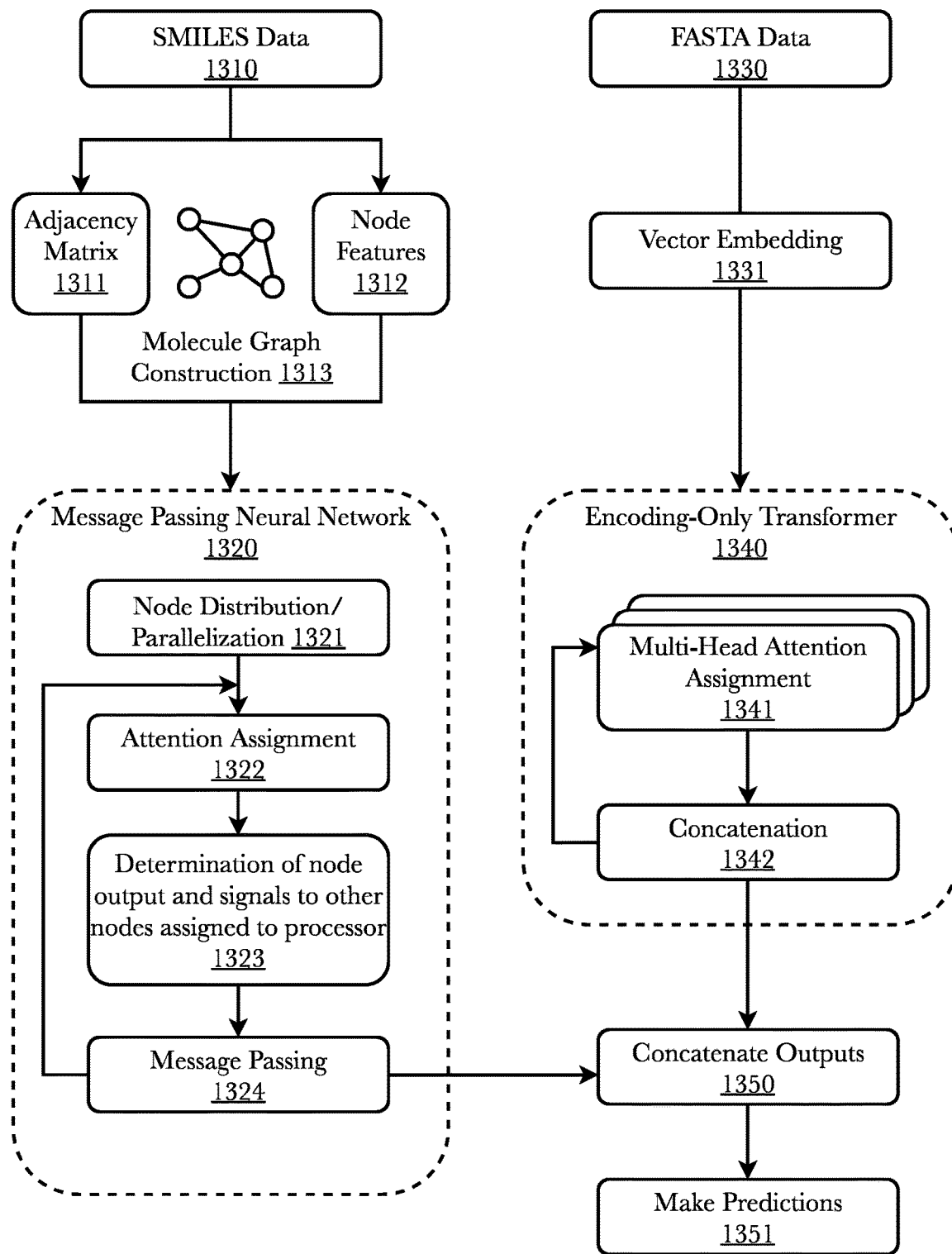
FIG. 13 is a diagram illustrating an exemplary architecture for prediction of molecule bioactivity using concatenation of outputs from a graph-based neural network and an attention-based transformer.

FIG. 13 is a diagram illustrating an exemplary architecture for prediction of molecule bioactivity using concatenation of outputs from a graph-based neural network which analyzes molecules and their known or suspected bioactivities with proteins and a sequence-based neural network which analyzes protein segments and their known or suspected bioactivities with molecules. In this architecture, in a first neural network processing stream, SMILES data 1310 for a plurality of molecules is transformed at a molecule graph construction stage 1313 into a graph-based representation wherein each molecule is represented as a graph comprising nodes and edges, wherein each node represents an atom and each edge represents a connection between atoms of the molecule. Each node represents the atom as node features comprising an atom type and a number of bonds available for that atom. The node features are represented as a node features matrix 1312. The molecule, then, is represented as nodes (atoms) connected by edges (bonds), and is specified as an adjacency matrix 1311 showing which nodes (atoms) are connected to which other nodes (atoms).

At the training stage, the adjacency matrices 1311 and node features matrices 1312 for many molecules are input into the MPNN 1320 along with vector representations of known or suspected bioactivity interactions of each molecule with certain proteins. Based on the training data, the MPNN 1320 learns the characteristics of molecules and proteins that allow interactions and what the bioactivity associated with those interactions is. At the analysis stage, a target molecule is input into the MPNN 1320, and the output of the MPNN 1320 is a vector representation of that molecule's likely interactions with proteins and the likely bioactivity of those interactions.

Once the molecule graph construction 1013 is completed, the node features matrices 1012 and adjacency matrices 1011 are passed to a message passing neural network (MPNN) 1020, wherein the processing is parallelized by distributing groups 1321 nodes of the graph amongst a plurality of processors (or threads) for processing. Each processor (or thread) performs attention assignment 1322 on each node, increasing or decreasing the strength of its relationships with other nodes, and outputs of the node and signals to other neighboring nodes 1323 (i.e., nodes connected by edges) based on those attention assignments are determined. Messages are passed between neighboring nodes based on the outputs and signals, and each node is updated with the information passed to it. Messages can be passed between 1324 processors and/or threads as necessary to update all nodes. In some embodiments, this message passing (also called aggregation) process is accomplished by performing matrix multiplication of the array of node states by the adjacency matrix to sum the value of all neighbors or divide each column in the matrix by the sum of that column to get the mean of neighboring node states. This process may be repeated an arbitrary number of times. Once processing by the MPNN is complete, its results are sent for concatenation 1350 with the results from a second machine learning algorithm, in this case an encoding-only transformer 1340.

In a second processing stream, FASTA data 1330 is converted to high-dimensional vectors 1331 representing the chemical structure of molecules. The vectors are processed by an encoding-only transformer 1340 which performs one or more iterations of multi-head attention assignment 1341 and concatenation 1342. Once processing by the encoding-only transformer 1340 is complete, its results are sent for concatenation 1350 with the results from the neural network, in this case the MPNN 1320.

Concatenation of the outputs 1350 from two different types of neural networks (here an MPNN 1320 and an LSTM 1340) determines which molecule structures and protein structures are compatible, allowing for prediction of bioactivity 1351 based the information learned by the neural networks from the training data.

Figure 19:
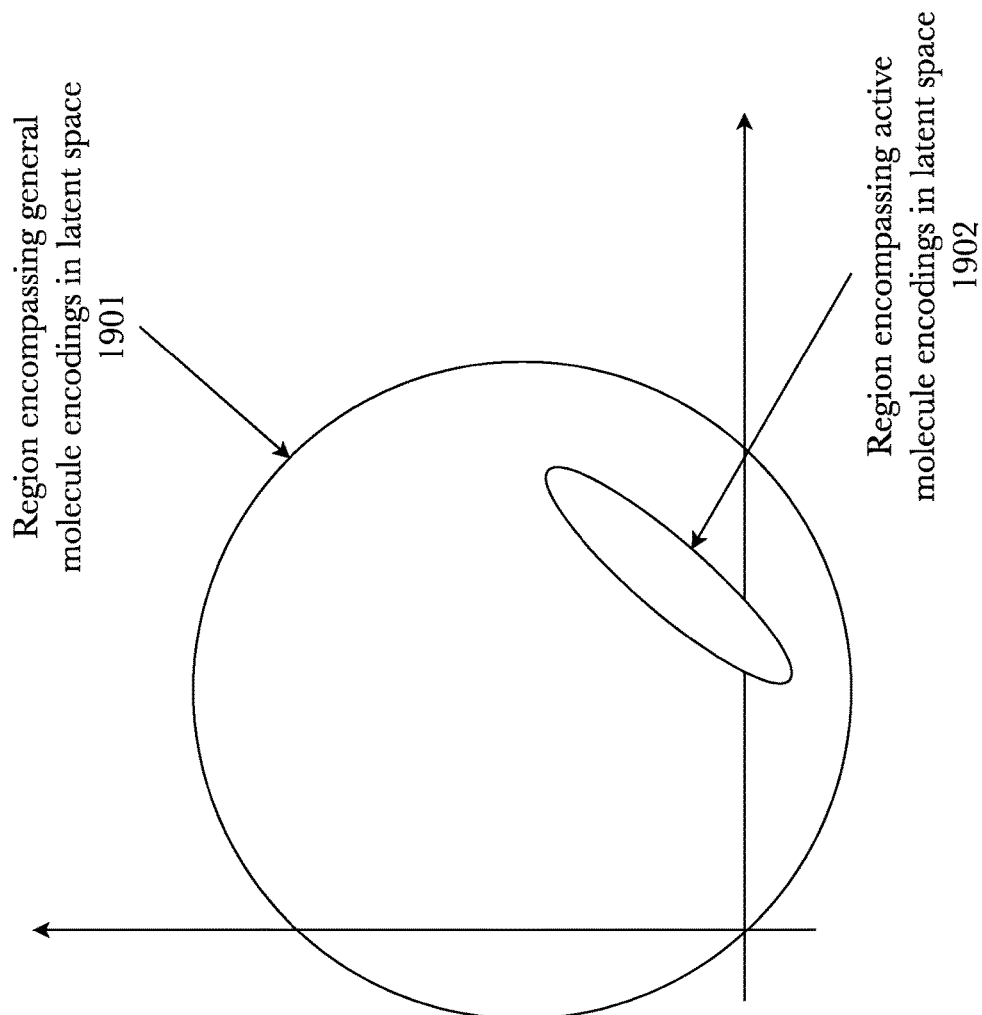
FIG. 19 is a diagram illustrating molecule encodings in latent space.

FIG. 19 is a diagram illustrating molecule encodings in latent space 1901. Once a model is trained that achieves a desirable reconstruction accuracy, a pipeline uses the model to generate molecules similar to a target dataset. Evaluating the generated molecules for chemical validity is performed using defined metrics to compare the generated data and to gauge whether the generation method is performing well. There are a few ways to compare how well the generation process works. When attempting to reconstruct the same molecule, the models sometimes produce molecules that are chemically impossible. It is therefore informative to compare the validity ratio of the generated molecules to the validity ratio of the reconstructed molecules of the active dataset. Ideally, the ratio is similar. If, on the other hand, the validity of the generated data is lower, it might mean that: (a) the exploration method of the latent space is not suitable—the explored space goes beyond the chemically meaningful regions; (b) the latent space representation is not smooth enough. A second method is by using molecular weight. The generated molecules are expected to have a similar molecular weight distribution to the active samples—a discrepancy would signal problems similar to those above. Lastly, chemical similarity. Computing and comparing the chemical similarity coefficients to estimate the molecular similarity of the generated and active molecules. This similarity should match the similarity of the active compounds amongst one another. These metrics can be used as a simple check validity (i.e., to see if the generated molecules "make sense"). Validity checking is particularly important in cases where certain properties are imposed, such as log P or molecular weight, to the generated molecules, as this is done by modifying the elements in the latent space, and allow the system to find the viable ranges of these parameters by finding where the above metrics start to deteriorate.

New molecules are generated by estimating a distribution of latent space 1902 that the active molecules are embedded into, then sampling from this distribution 1902 and running the samples through a decoder to recover new molecules. The distribution is approximated by a multivariate Gaussian, with mean and covariance matrices computed from the latent representations of the active molecules.

Figure 27:
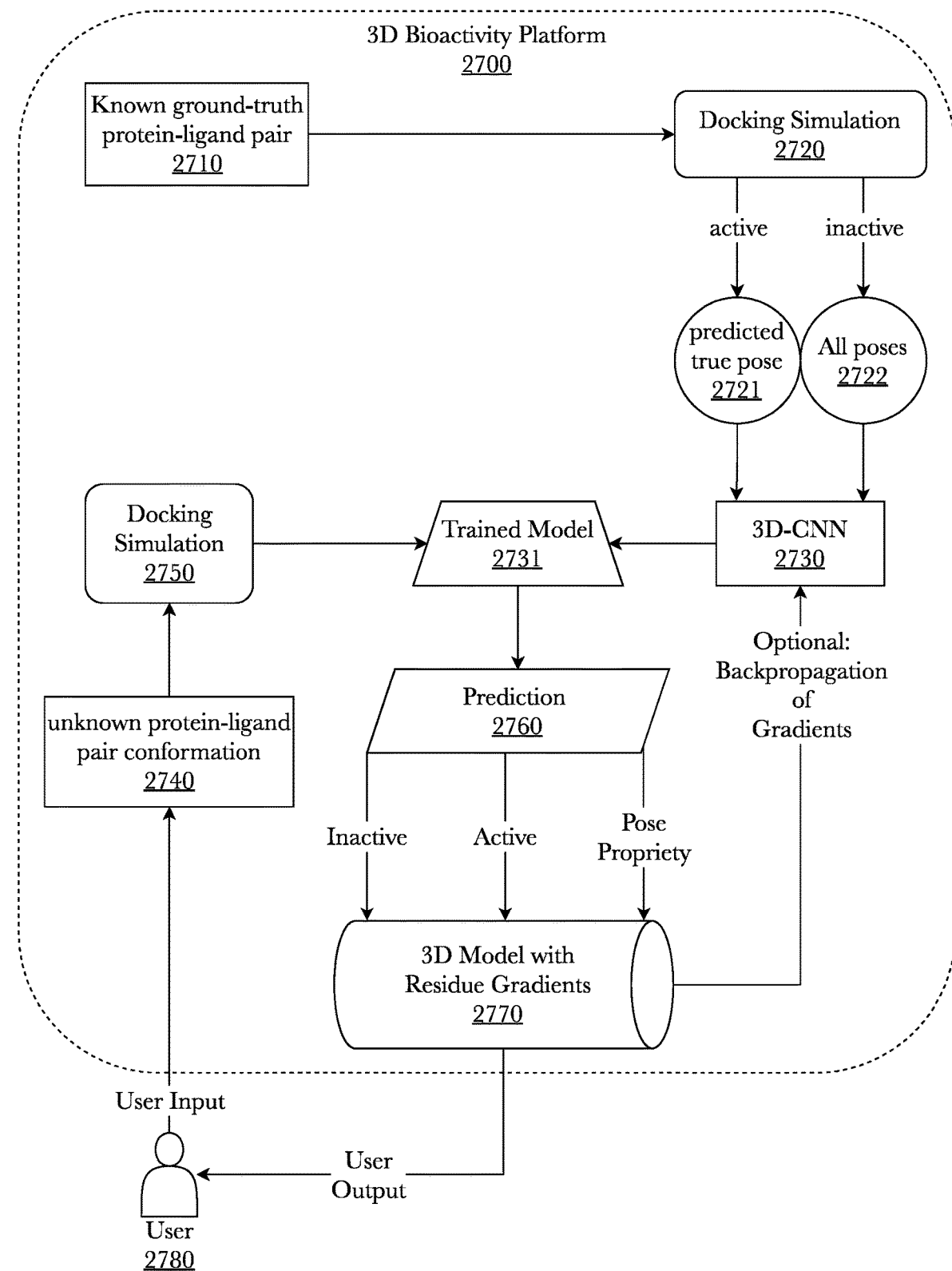
FIG. 27 is a block diagram of an exemplary model architecture for a 3D Bioactivity platform.

FIG. 27 is a block diagram of an exemplary model architecture for a 3D Bioactivity platform 2700. The model architecture used is a three-dimensional convolutional neural network (3D-CNN) 2730. Convolutional Neural Networks 2730 are widely used on tasks such as image classification. They are multi-layer perceptrons that are regularized in such a way as to take advantage of the translational invariance of the content of pictures (e.g., a gavel is a gavel whether it is in the center or corner of an image.). In a convolutional layer, each output neuron is not connected to all the input neurons, but to a spatially-localized subset. CNN architectures operate analogously in higher-dimensional spaces. Docking simulations 2720/2750 take as input the ligand and protein molecules 2710/2740 and their three-dimensional structures. Docking 2720 assigns scores to each pose 2721/2722 to be used in the model 2731 depending on the embodiment. Some embodiments may use all poses, whereas other embodiments use only the highest scored pose for active molecules and all poses for inactive molecules. After docking simulations 2720/2750 have been completed, molecules are voxelated and are used as the model 2731 input, which are used to train the model 2731 to predict 2760 or classify these voxelated representations into active/inactive and pose propriety categories.

In reality, the observed bioactivity of a ligand is not due to a single pose within the binding site, but due to the contributions from a number of possible poses. According to one embodiment, the population of a given pose is given as:

$$W_b = e^{\frac{-E}{kT}}$$

where E, k and T correspond to the free energy of binding, Boltzmann's constant, and the temperature, respectively. An estimate of E from the Force Field can be determined, and subsequently the loss may be defined as:

$$L = \frac{\sum_{poses}(W_b * (\text{Model(pose)} - \text{True\_affinity})^2)}{\sum_{poses}(W_b)}$$

This loss function corresponds to interpreting E not as the true free energy of binding, but instead as the probability of a pose being the "true" pose. This method allows for superimposing the probability-weighted atom density grids, which speeds computation up enormously. The loss function above is merely exemplary and modifications to the loss function above are anticipated.

According to an aspect of various embodiments, an additional 'Pose Score' output node to the CNN is improvised. 3D-CNNs 2730 comprise an additional output node that is trained on classifying the input poses as being "low" root-mean-square deviation (RMSD) (<2 Angstrom RMSD vs. crystal structure) and "high" RMSD (>2 Angstrom RMSD vs. crystal structure). This predicted classification is used to modulate the binding-affinity loss as follows: Affinity prediction is trained using an L2-like pseudo-Huber loss that is hinged when evaluating high RMSD poses. That is, the model is penalized for predicting both a too low and too high affinity of a low RMSD pose, but only penalized for predicting too high an affinity for a high RMSD pose. Since the PDB dataset used comprises crystal structures for each available datapoint, it is possible to generate corresponding classification labels into high/low RSMD poses for each docked complex. Two aspects of various embodiments are therefore anticipated. The first aspect comprises extracting RMSD labels for datapoints where crystal structures are available and do not contribute any "Pose Score" loss to the remaining items. The second aspect comprises using Boltzmann-averaging of pose predictions. This second aspect has the advantage of not requiring crystal structures of any complexes.

The output 2770 of the model 2731 may combine the separate poses at test-time. Actions taken on the predictions may be selected from one of the actions in the list comprising: Analogous Boltzmann-weighing of the predictions, Averaging of the predictions across all poses, simple predictions only on the best pose, or any combination thereof.

The visualizations 2770 produced by the model 2731 may use methods such as integrated gradients, which require only a single forwards/backwards pass of the models, which is an improvement over the current state of the art. According to various embodiments, integrated gradients, and other gradient visualizations are achieved by computing the voxel saliencies, and coloring a surface/molecule of its properties. If a MaxPool layer is an initial layer of the model 2731, simple smoothing (i.e., halving the resolution of the grid) may correct the visualization from the zero-average voxel-importance.

Other visualizations methods comprise assigning voxel-gradients back to the atoms of the input molecules, which are adapted to propagate whatever importances are computed for each voxel. Importances provide the user with an explanation of which parts of the protein-ligand pair the model 2731 predicts is most strongly bonded. The more important the atom, the higher the number. The number may be represented by one or more colors or shading. The importance reference system described above, i.e., the color-coordinated importances, is only one example of an importance reference system. Other methods such as coloring, shading, numbering, lettering, and the like may be used.

One use of the exemplary 3D bioactivity platform 2700 embodiment disclosed herein comprises a user 2780 that inputs unknown molecule conformations 2740 into the 3D bioactivity platform 2700 and receives back a prediction as to whether the molecule is active or inactive, a pose score (telling the propriety of the pose), and a 3D model complete with gradient representations of the significant residues 2760/2770.

Figure 29:
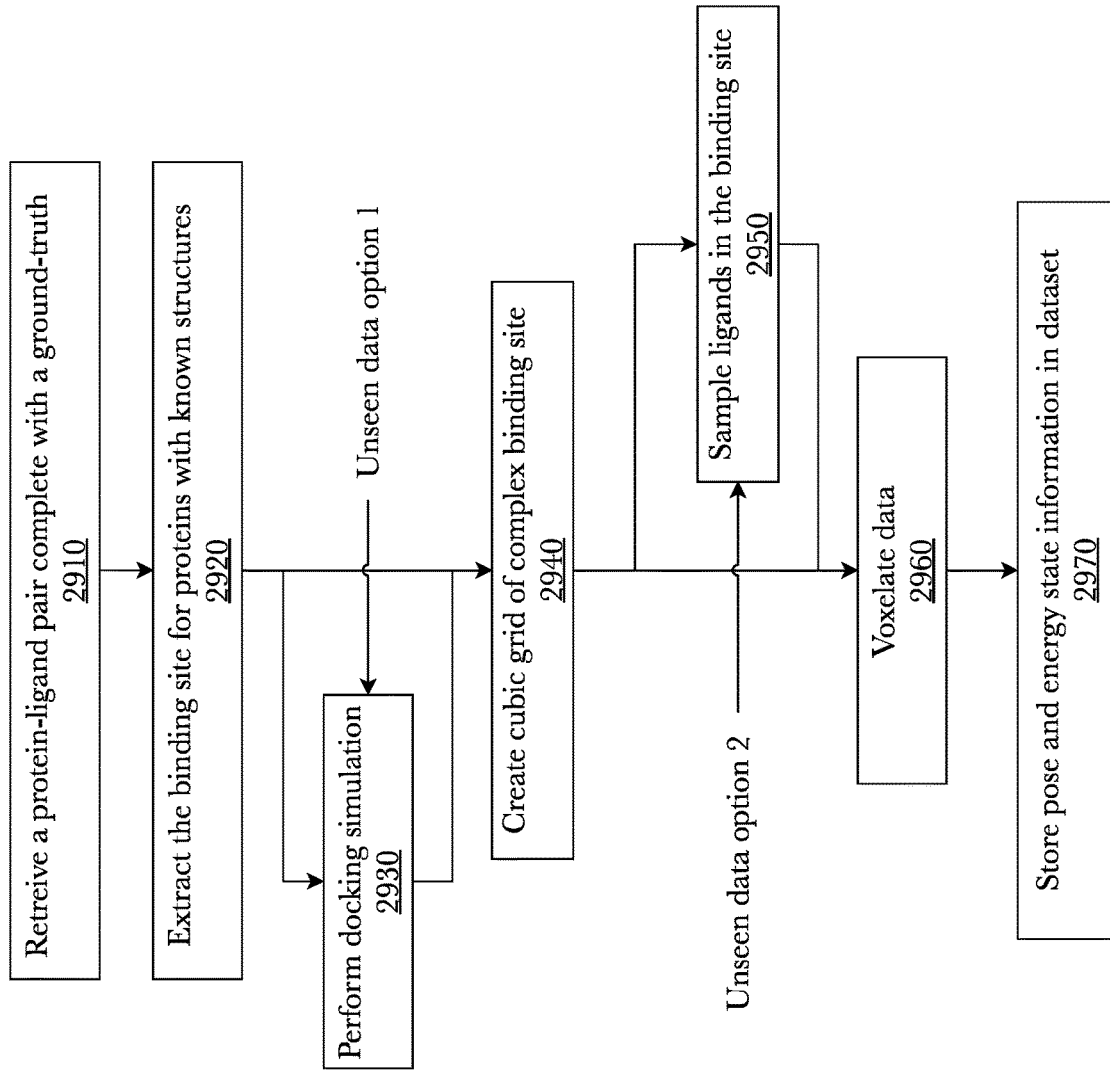
FIG. 29 is a flow diagram illustrating an exemplary method for generating data for use in training a 3D-CNN used by a 3D Bioactivity platform.

FIG. 29 is a flow diagram illustrating an exemplary method for generating data for use in training a 3D-CNN used by a 3D Bioactivity platform. Training data is generated for the training of the classifier via docking, wherein the method of docking gives the energy states of each protein-ligand pose. The lower the energy state, the stronger the binding affinity. Inputs for the docking mechanism comprise a particular protein-ligand pair and its ground-truth state (i.e., whether it is active or inactive) 2910. On such a pair, the docking simulation is performed and if the pair is labeled as inactive, all data points are kept in the training dataset, if an active label is found as the ground truth state, only the best (lowest energy) pose is kept. According to another embodiment, the top 20 (lowest energy) poses are kept for the training dataset. Further anticipated embodiments acknowledge that any number of poses may be kept for training and the examples contained herein are merely exemplary. According to aspects of various embodiments, simple force-field based optimization of a ligand pose in a binding pocket can substitute for docked poses at reduced computational expense in a binding affinity prediction task without a significant decrease in accuracy. Force-field optimization considers at least one of the constant terms selected from the list of dissociation, inhibition, and half-concentration (IC50) in order to capture the molecular interactions, e.g., hydrogen bonds, hydrophobic bonds, etc. Many databases known in the art may be used to get this information such as the Protein Data Bank (PDB) as one example. In simple terms, docking guides the machine learning (3D-CNN) to realize what poses to keep and to realize what the molecule likely looks like in the pocket.

Prior to featurization, the model input should be a cubic grid centered around the binding site of the complex, the data being the location and atom type of each atom in each the protein and ligand, flagged as to belonging either to the protein or the ligand. This is trivial for complexes with known structures, wherein the binding site is the center of the ligand. For unseen data, two exemplary options are anticipated: generate complexes using docking, or generate complexes by sampling ligand poses.

According to one embodiment, an initial step in dataset creation is to extract the binding sites from all the proteins for which have known structures (this need only be done once ever) 2920. Next, using the aforementioned docking option, complexes are created via docking simulations 2930. However, if the foregoing second option is used, then sampling the ligands in the binding site using the cropped protein structures may be done post-step three for faster data loading 2950. The next step 2940 is to crop to a 24 Angstrom box around the binding-site center (either geometric or center-of-mass). The data is then voxelated 2960 and stored in a dataset 2970. Different box sizes or centering choices is anticipated, however, in one embodiment, the data is voxelated to a certain resolution, e.g., 0.5 Angstrom. This resolution is sensible as it ensures no two atoms occupy the same voxel.

Figure 32:
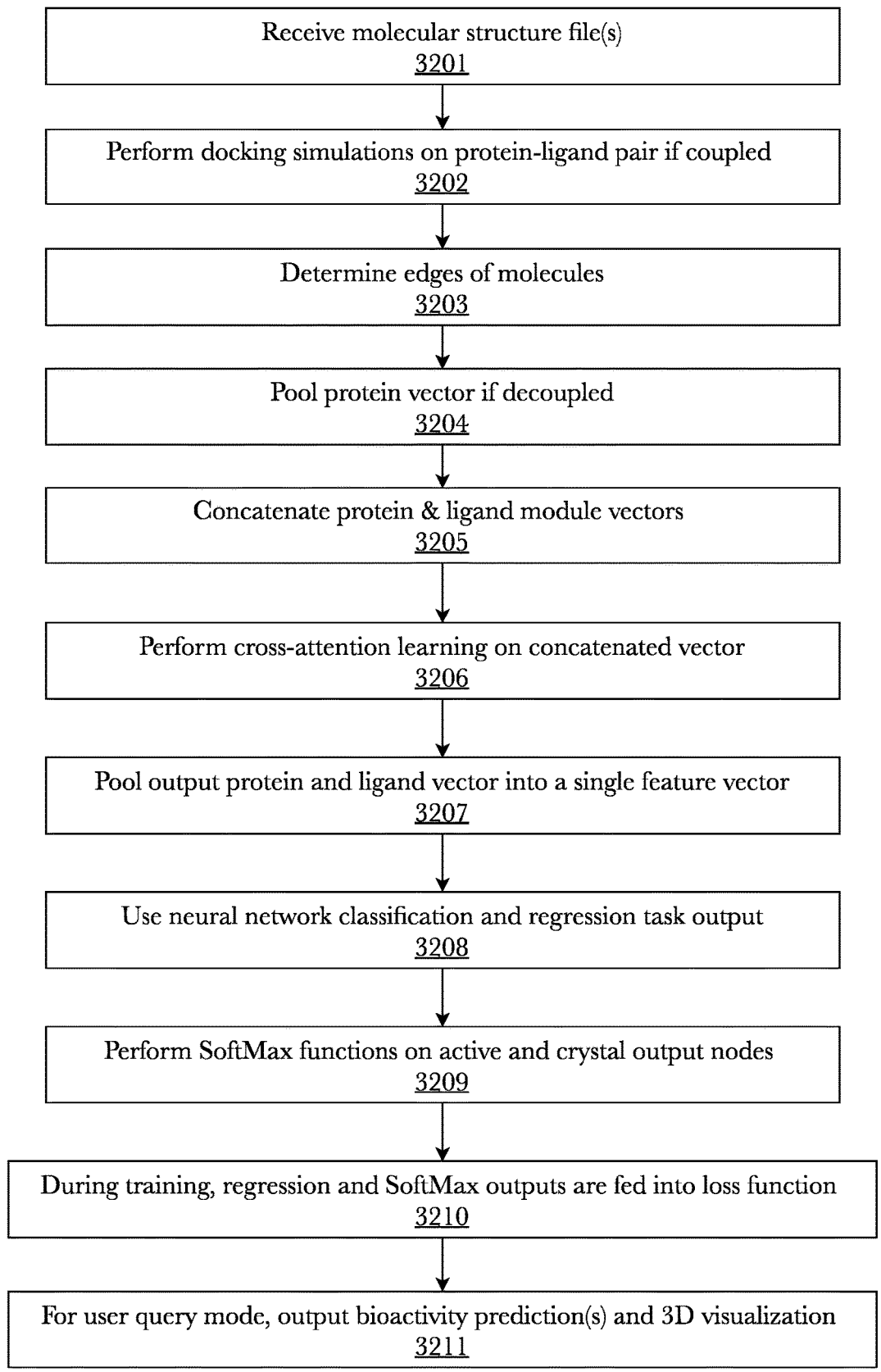
FIG. 32 is a flow diagram illustrating an exemplary method for classifying protein-ligand pairs using a Point-Cloud Bioactivity platform.

FIG. 32 is a flow diagram illustrating an exemplary method for classifying protein-ligand pairs using a Point-Cloud Bioactivity platform. A first pass through the method illustrated described is to train the model for future queries of user submitted protein-ligand pairs. In such a case, ground-truth protein-ligand pairs (in the form of molecular structure files) 3201 are used in docking simulations 3202 to determine one or more best poses of the molecular conformation. Docking simulations guide the machine learning to realize what poses to keep and to realize what the molecule likely looks like in the pocket. Next, docking simulations output molecular structure files that are used by transformer convolution classifiers to generate edges between the atomic coordinates of the proteins and ligands 3203. If the docking simulations fail, protein atoms of interest are pooled into a single vector 3204 and concatenated with the ligand feature vector 3205, otherwise the protein atoms within a spatial threshold of some amount (according to one embodiment, 4 angstroms) are kept and concatenated with the ligand vector 3205. An attention-restricted (also cross-attention) transformer convolution classifier is used to learn the importances and interactions between the protein-ligand pair 3206. The cross-attention module outputs a feature vector for each atom in each molecule which is then pooled into a single feature vector for each molecule 3207. A neural network—a feed-forward neural network in a preferred embodiment—outputs one to five outputs 3208 depending on the task, which in turn may make up to three predictions. One output is a prediction of the generated protein-ligand pair's active or inactive nature, while another is whether the crystal structure closely matches the crystal structure of the ground-truth pair, typically within 2 angstroms 3209. The regression is used to determine bioactivity which may be a numerical value generated by a regression task and based off one or more bioactivity metrics such as the pair's inhibition constant, $IC_{50}$, or another metric. During training, outputs are fed into a loss function and optimizer for backpropagation as is typical of machine learning 3210, while also using the crystalline structure similarity prediction to determine the legitimacy of the model's bioactivity prediction.

A second pass through the diagram illustrates the case of employing an already trained point-cloud based bioactivity prediction model as described above. A user may submit a query, in the form of a molecular structure file, or other format which is then turned into a molecular structure file, and receive in return one or more predictions selected from the list of active classification, crystal similarity classification, regression task, combined active/crystal classification, a bioactivity classification, or some combination thereof, as well as a three-dimensional point-cloud based visualization 3211 highlighting importances and saliences of the queried molecule. Further information on the visualization follows in the next figure.

Figure 33:
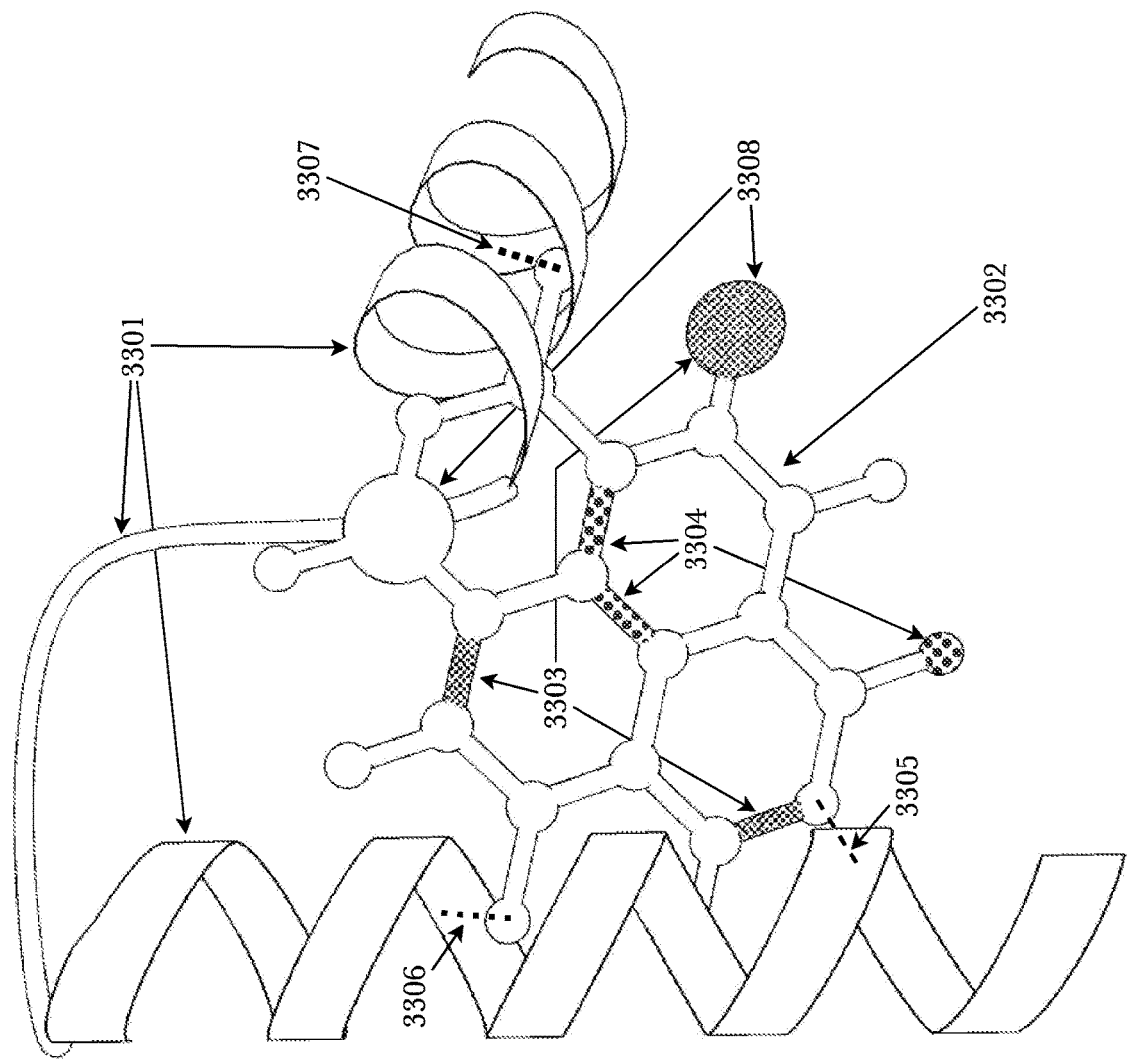
FIG. 33 is a block diagram illustrating an exemplary point-based visualization.

FIG. 33 is a block diagram illustrating an exemplary point-based visualization. This diagram is merely for illustrative purposes and is not to scale, may not reflect actual protein-ligand interactions, and may not accurately reflect the visualizations produced by the point-cloud bioactivity module. In this diagram of a point-based visualization, a protein 3301 and ligand molecule 3302 show directly the importance assigned to protein-ligand interactions represented by size 3308, shading 3303/3304, and dashed lines 3305. The point-based visualization colors atoms 3303/3304 according to the positive/negative-ness of the saliencies obtained through integrated gradients, values of attention coefficients, or any variation thereof, as well as scaling their size 3308 according to the magnitude, as can be seen by the larger atoms. Colored dashed lines 3305-3307 are used to highlight importance attributed to interactions and are typically, but not limited to be always within 4 angstroms of each other.

This visualization is based on a point-cloud model with a transformer convolution architecture. This allows specification of edge features and does not require padding, and is thus the preferred point-based model architecture according to one embodiment. This embodiment performs graph-message-passes with messages computed using attention of neighbors, whilst taking edge features into account. By computing the importance with respect to the protein-ligand edge features (which are embeddings of the distance into a series of sinusoids of various frequencies, analogous to the positional embedding used in transformer models), and considering all protein-ligand atom-pairs within 4 Angstrom of one another to be connected by edges, model attributions to certain interactions may be directly highlighted.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 35:
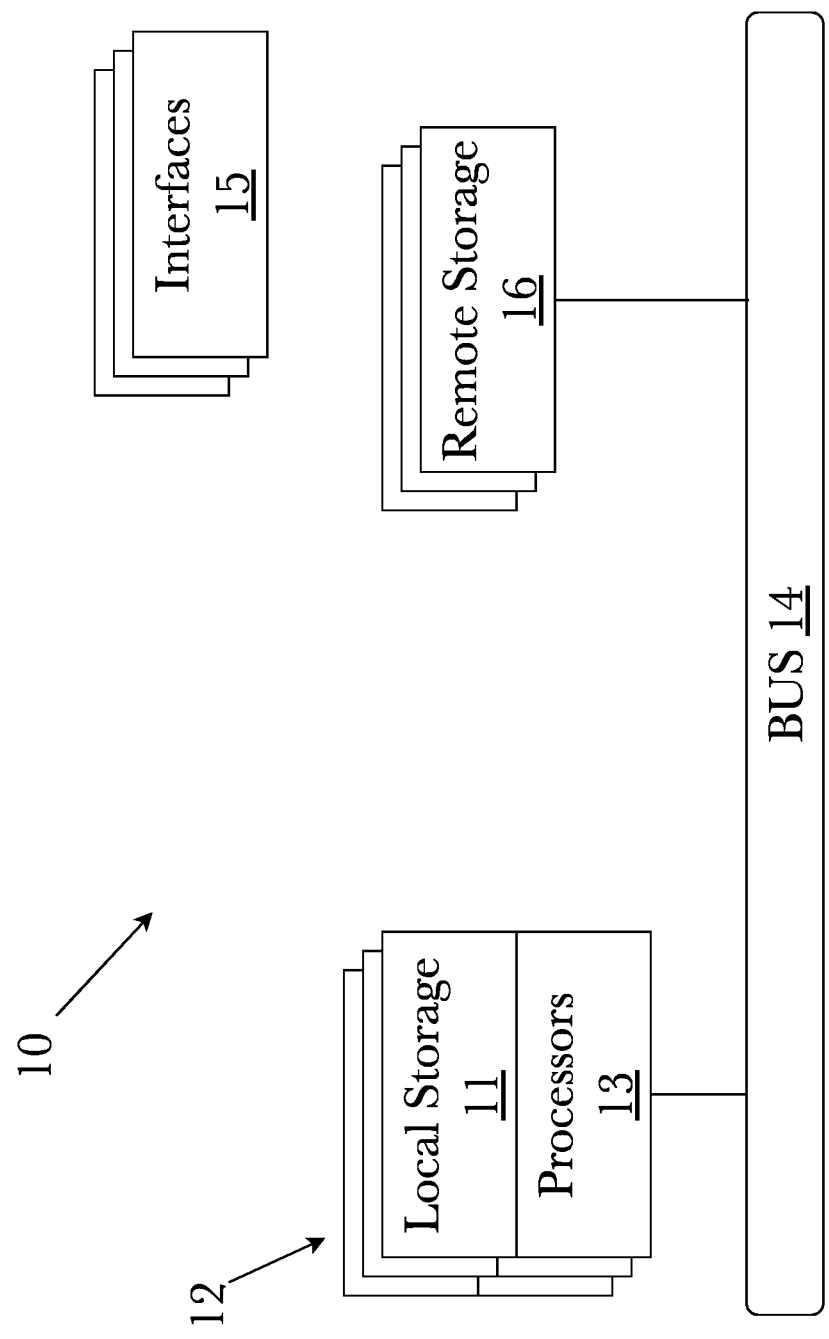
FIG. 35 is a block diagram illustrating an exemplary hardware architecture of a computing device.

Referring now to FIG. 35, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 35 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 36:
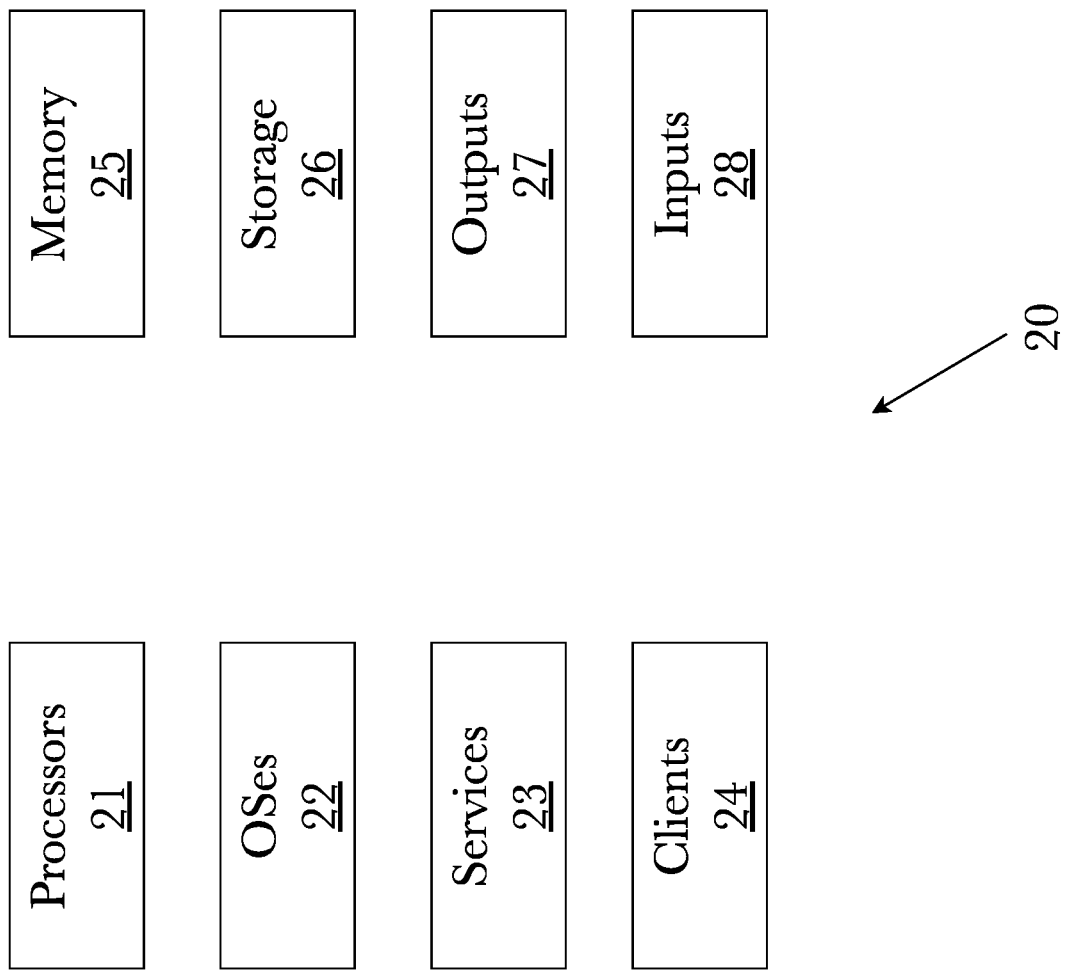
FIG. 36 is a block diagram illustrating an exemplary logical architecture for a client device.

In some aspects, systems may be implemented on a standalone computing system. Referring now to FIG. 36, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 35). Examples of storage devices 26 include flash memory, magnetic hard drive, CD-ROM, and/or the like.

Figure 37:
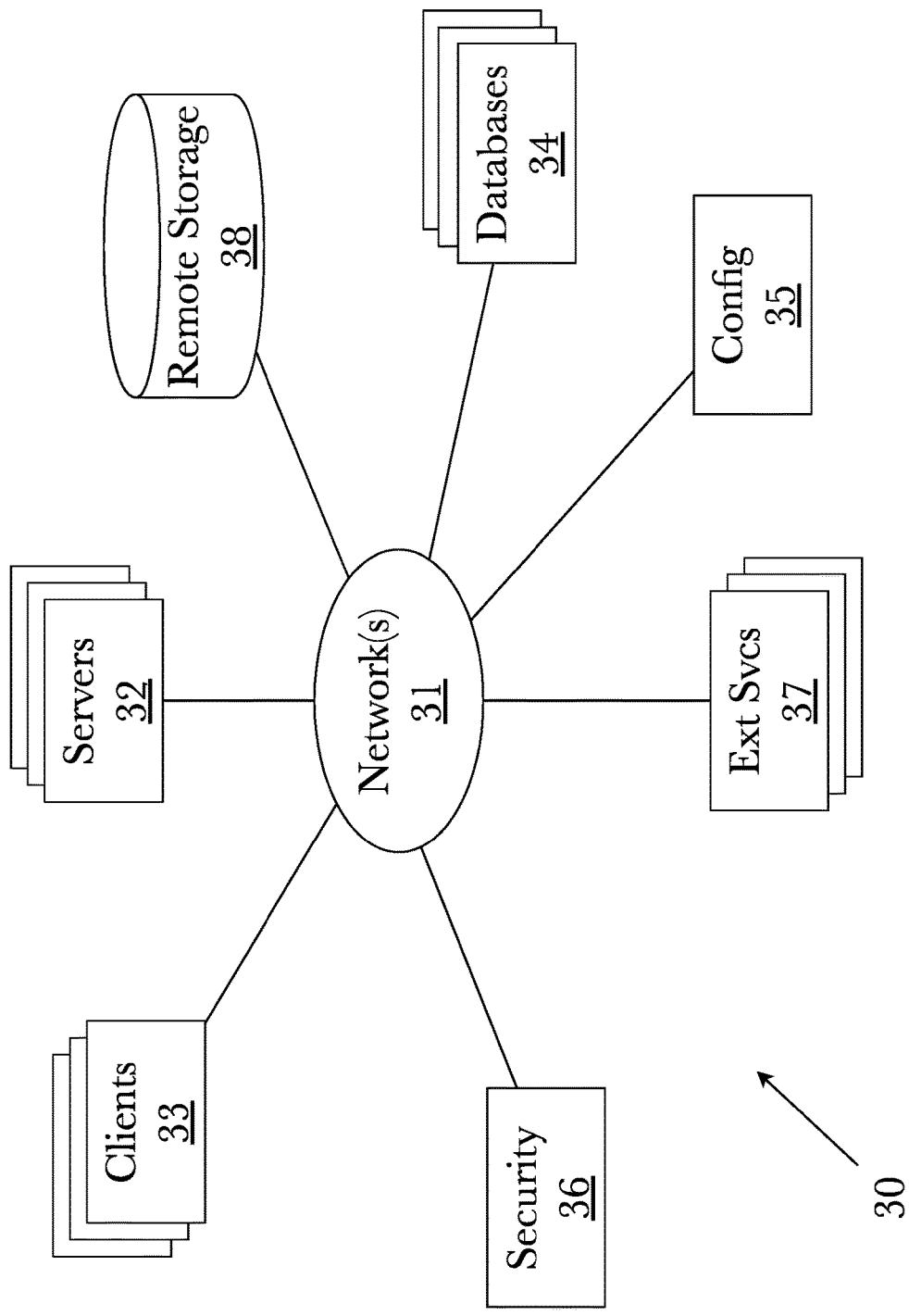
FIG. 37 is a block diagram showing an exemplary architectural arrangement of clients, servers, and external services.

In some aspects, systems may be implemented on a distributed computing network, such as one having any number of clients and/or servers. Referring now to FIG. 37, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 36. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 38:
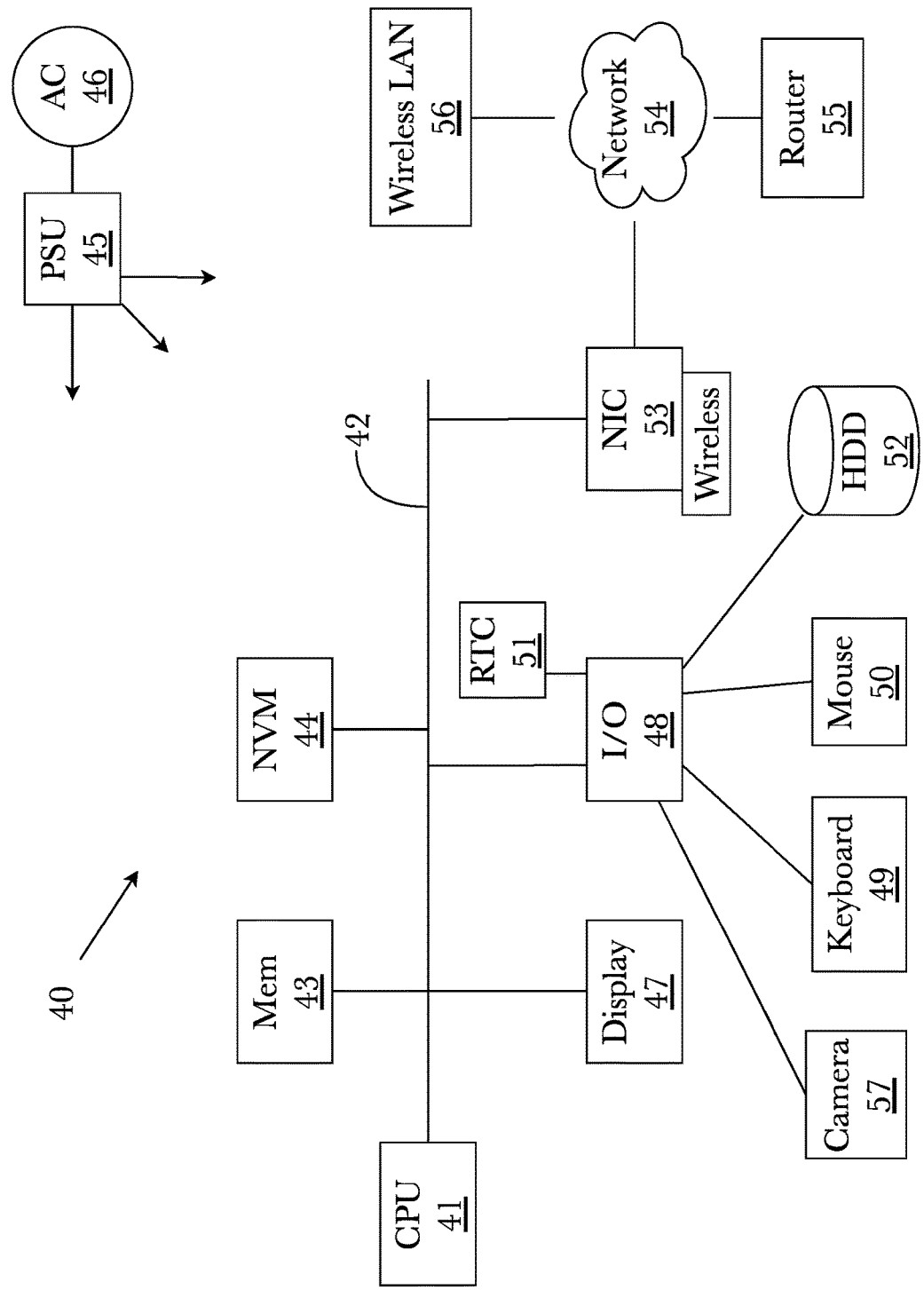
FIG. 38 is another block diagram illustrating an exemplary hardware architecture of a computing device.

FIG. 38 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC)

supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for prediction of protein-ligand bioactivity comprising:
    a computing device comprising a memory and a processor;
    a point-cloud based bioactivity module comprising a first plurality of programming instructions stored in the memory and operating on the processor, wherein the first plurality of programming instructions causes the computing device to:
        receive a molecular structure file, wherein the molecular structure file comprises molecular and structural information about at least one protein and one ligand;
        generate a graph-based neural network of the protein, wherein edges of the graph-based neural network of the protein are determined using the molecular structure file;
        generate a graph-based neural network of the ligand, wherein edges of the graph-based neural network of the ligand are determined using the molecular structure file;
        concatenate a set of vectors from both the graph-based neural network of the protein and the graph-based neural network of the ligand;
        perform restricted-cross-attention learning on the concatenated vectors;
        generate a single feature vector from the restricted-cross-attention learning;
        use the single feature vector in a feed-forward neural network to produce one or more outputs selected from the group consisting of active or inactive classification, crystalline-structure similarity, and regression analysis; and
        use the one or more outputs to produce one or more bioactivity predictions about one or more protein-ligand pairs.

2. The system of claim 1, wherein docking simulations are performed on the protein and the ligand from the molecular structure file if the protein and the ligand are coupled.

3. The system of claim 1, wherein the vector from the graph-based neural network of the protein comprises atoms within 4 angstroms of the ligand if the protein and the ligand are coupled.

4. The system of claim 1, wherein the vector from the graph-based neural network of the protein comprises atoms of a binding pocket if the protein and the ligand are decoupled.

5. The system of claim 1, wherein the crystalline-structure similarity prediction is used to determine the legitimacy of the one or more bioactivity predictions.

6. The system of claim 1, wherein the graph-based neural network of the protein and the graph-based neural network of the ligand are based on one or more transformer convolution classifiers.

7. The system of claim 1, wherein the one or more outputs are used with a loss function to produce a trained model for bioactivity prediction.

8. The system of claim 1, wherein the machine learning model is a transformer convolution classifier.

9. The system of claim 1, further comprising an output of a three-dimensional visualization of the one or more protein-ligand pairs.

10. The system of claim 9, wherein the three-dimensional visualization comprises features of molecular interaction properties.

11. A method for prediction of protein-ligand bioactivity comprising the steps of:
    receiving a molecular structure file, wherein the molecular structure file comprises molecular and structural information about at least one protein and one ligand;
    generating a graph-based neural network of the protein, wherein edges of the graph-based neural network of the protein are determined using the molecular structure file;
    generating a graph-based neural network of the ligand, wherein edges of the graph-based neural network of the ligand are determined using the molecular structure file;
    concatenating a set of vectors from both the graph-based neural network of the protein and the graph-based neural network of the ligand;
    performing restricted-cross-attention learning on the concatenated vectors;
    generating a single feature vector from the restricted-cross-attention learning;
    using the single feature vector in a feed-forward neural network to produce one or more outputs selected from the group consisting of active or inactive classification, crystalline-structure similarity, and regression analysis; and
    using the one or more outputs to produce one or more bioactivity predictions about one or more protein-ligand pairs.

12. The method of claim 11, wherein docking simulations are performed on the protein and the ligand from the molecular structure file if the protein and the ligand are coupled.

13. The method of claim 11, wherein the vector from the graph-based neural network of the protein comprises atoms within 4 angstroms of the ligand if the protein and the ligand are coupled.

14. The method of claim 11, wherein the vector from the graph-based neural network of the protein comprises atoms of a binding pocket if the protein and the ligand are decoupled.

15. The method of claim 11, wherein the crystalline-structure similarity prediction is used to determine the legitimacy of the one or more bioactivity predictions.

16. The method of claim 11, wherein the graph-based neural network of the protein and the graph-based neural network of the ligand are based on one or more transformer convolution classifiers.

17. The method of claim 11, wherein the one or more outputs are used with a loss function to produce a trained model for bioactivity prediction.

18. The method of claim 11, wherein the machine learning model is a transformer convolution classifier.

19. The method of claim 11, further comprising an output of a three-dimensional visualization of the one or more protein-ligand pairs.

20. The method of claim 19, wherein the three-dimensional visualization comprises features of molecular interaction properties.

* * * * *